United States Patent
Carfi et al.

(10) Patent No.: US 10,414,802 B2
(45) Date of Patent: Sep. 17, 2019

(54) MAMMALIAN CELLS EXPRESSING CYTOMEGALOVIRUS ANTIGENS

(71) Applicant: GLAXOSMITHKLINE BIOLOGICALS S.A., Rixensart (BE)

(72) Inventors: Andrea Carfi, Cambridge, MA (US); Claudio Ciferri, Oakland, CA (US); Irmgard Hofmann, Vienna (AT); Holger Laux, Basel (CH); Anders Lilja, Vienna (AT); Yingxia Wen, Acton, MA (US)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

(21) Appl. No.: 15/522,455

(22) PCT Filed: Oct. 29, 2015

(86) PCT No.: PCT/IB2015/058349
§ 371 (c)(1),
(2) Date: Apr. 27, 2017

(87) PCT Pub. No.: WO2016/067239
PCT Pub. Date: May 6, 2016

(65) Prior Publication Data
US 2017/0362278 A1    Dec. 21, 2017

(30) Foreign Application Priority Data
Oct. 31, 2014   (EP) ..................................... 14191385

(51) Int. Cl.
| | | |
|---|---|---|
| *C07K 14/045* | (2006.01) | |
| *C07K 14/005* | (2006.01) | |
| *A61K 39/00* | (2006.01) | |
| *C12N 5/071* | (2010.01) | |
| *C07K 14/05* | (2006.01) | |

(52) U.S. Cl.
CPC ............ *C07K 14/005* (2013.01); *A61K 39/00* (2013.01); *C12N 5/0682* (2013.01); *C12N 2510/02* (2013.01); *C12N 2710/16122* (2013.01); *C12N 2710/16134* (2013.01); *C12N 2710/16151* (2013.01)

(58) Field of Classification Search
CPC .......... C12N 2710/16734; C12N 15/86; C12N 2510/02; A61K 39/25; A61K 35/763; C07K 16/088; G01N 33/56994; Y02A 50/388; Y02A 50/412
See application file for complete search history.

(56) References Cited

U.S. PATENT DOCUMENTS
7,704,510 B2    4/2010  Shenk et al.

FOREIGN PATENT DOCUMENTS
| WO | 2014/005959 | 1/2014 |
|---|---|---|
| WO | 2014/097113 | 6/2014 |
| WO | 2015/092735 | 6/2015 |
| WO | 2015/092737 | 6/2015 |
| WO | 2015/165480 | 11/2015 |
| WO | 2015/166427 | 11/2015 |

OTHER PUBLICATIONS

Uchida et al. Journal of Virology, 2013, vol. 87 (3), pp. 1430-1442.*
Rycknnan et al. (A) Proc Natl Acad Sci U S A. Sep. 16, 2008; 105(37): 14118-14123.*
Ryckman et al., Characterization of the Human Cytomegalovirus gH/gL/UL128-131 Complex that Mediates Entry into Epithelial and Endothelial Cells, 2008 J. Virol. 82(1):60-70.
Wen et al., Human Cytomegalovirus gH/gL/UL128/UL130/UL131A complex elicits Potently Neutralizing Antibodies in Mice, 2014 Vaccine 32(30):3796-3804.
Hofmann et al., Expression of the Human Cytomegalovirus Pentamer Complex for Vaccine Use in a CHO system, 2015 Biotech. Bioeng. 112(12):2505-2515.
European Patent Office as International Searching Authority, International Search Report and Written Opinion for Int'l. Appl. No. PCT/IB2015/058349, dated Jan. 27, 2016, 14 total pages.
Kim et al., CHO Cells in Biotechnology for Production of Recombinant Proteins: Current State and Further Potential, 2011 Applied Microb. and Biotech. 93(3):917-930.

* cited by examiner

*Primary Examiner* — Bao Q Li
(74) *Attorney, Agent, or Firm* — Rebecca J. Stephens; Virginia G. Campen

(57) ABSTRACT

This invention relates to cytomegalovirus (CMV) proteins suitable for vaccine uses. Provided herein are mammalian host cells, in particular CHO cells, in which the sequence(s) encoding CMV proteins gH, gL, pUL128, pUL130, pUL131 (or a complex-forming fragment thereof) are stably integrated into the genome.

18 Claims, 5 Drawing Sheets

Specification includes a Sequence Listing.

SEQUENCE LISTING

<160> NUMBER OF SEQ ID NOS: 39

<210> SEQ ID NO 1
<211> LENGTH: 742
<212> TYPE: PRT
<213> ORGANISM: Human herpesvirus 5
<220> FEATURE:
<221> NAME/KEY: MISC_FEATURE
<222> LOCATION: (1)..(742)
<223> OTHER INFORMATION: /note="Strain Merlin"

<400> SEQUENCE: 1

```
Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350
```

-continued

Arg Gln Glu Glu Ala Gly Ala Gln Val Ser Val Pro Arg Ala Leu Asp
    355                 360                 365

Arg Gln Ala Ala Leu Leu Gln Ile Gln Glu Phe Met Ile Thr Cys Leu
370                 375                 380

Ser Gln Thr Pro Pro Arg Thr Thr Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
                420                 425                 430

His Leu Ile Pro Gln Trp Ala Leu Arg Gln Ile Ala Asp Phe Ala Leu
                435                 440                 445

Lys Leu His Lys Thr His Leu Ala Ser Phe Leu Ser Ala Phe Ala Arg
                450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
                500                 505                 510

Glu Tyr Leu Ser Asp Leu Tyr Thr Pro Cys Ser Ser Ser Gly Arg Arg
                515                 520                 525

Asp His Ser Leu Glu Arg Leu Thr Arg Leu Phe Pro Asp Ala Thr Val
                530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Ile Val Thr
                580                 585                 590

Asn Gln Tyr Leu Ile Lys Gly Ile Ser Tyr Pro Val Ser Thr Thr Val
                595                 600                 605

Val Gly Gln Ser Leu Ile Ile Thr Gln Thr Asp Ser Gln Thr Lys Cys
                610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
                660                 665                 670

Asp Asp Val Leu Phe Ala Leu Asp Pro Tyr Asn Glu Val Val Val Ser
                675                 680                 685

Ser Pro Arg Thr His Tyr Leu Met Leu Leu Lys Asn Gly Thr Val Leu
                690                 695                 700

Glu Val Thr Asp Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
                740

<210> SEQ ID NO 2
<211> LENGTH: 742

```
<212> TYPE: PRT
<213> ORGANISM: Human herpesvirus 5
<220> FEATURE:
<221> NAME/KEY: MISC_FEATURE
<222> LOCATION: (1)..(742)
<223> OTHER INFORMATION: /note="Strain Towne"

<400> SEQUENCE: 2
```

Met Arg Pro Gly Leu Pro Ser Tyr Leu Ile Val Leu Ala Val Cys Leu
1               5                   10                  15

Leu Ser His Leu Leu Ser Ser Arg Tyr Gly Ala Glu Ala Ile Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu

```
                    370                 375                 380
Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
                420                 425                 430

His Leu Ile Pro Gln Trp Ala Leu Arg Gln Ile Ala Asp Phe Ala Leu
            435                 440                 445

Lys Leu His Lys Thr His Leu Ala Ser Phe Leu Ser Ala Phe Ala Arg
        450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
                500                 505                 510

Glu Tyr Leu Ser Asp Leu Tyr Thr Pro Cys Ser Ser Gly Arg Arg
            515                 520                 525

Asp His Ser Leu Glu Arg Leu Thr Arg Leu Phe Pro Asp Ala Thr Val
        530                 535                 540

Pro Thr Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Val Val Thr
                580                 585                 590

Asn Gln Tyr Leu Ile Lys Gly Ile Ser Tyr Pro Val Ser Thr Thr Val
            595                 600                 605

Val Gly Gln Ser Leu Ile Ile Thr Gln Thr Asp Ser Gln Thr Lys Cys
        610                 615                 620

Glu Leu Thr Arg Asn Met His Thr Thr His Ser Ile Thr Ala Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
                660                 665                 670

Asp Asp Val Leu Phe Ala Leu Asp Pro Tyr Asn Glu Val Val Ser
            675                 680                 685

Ser Pro Arg Thr His Tyr Leu Met Leu Leu Lys Asn Gly Thr Val Leu
        690                 695                 700

Glu Val Thr Asp Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
            740
```

<210> SEQ ID NO 3
<211> LENGTH: 743
<212> TYPE: PRT
<213> ORGANISM: Human herpesvirus 5
<220> FEATURE:
<221> NAME/KEY: MISC_FEATURE
<222> LOCATION: (1)..(743)

<223> OTHER INFORMATION: /note="Strain AD169"

<400> SEQUENCE: 3

```
Met Arg Pro Gly Leu Pro Pro Tyr Leu Thr Val Phe Thr Val Tyr Leu
1               5                   10                  15
Leu Ser His Leu Pro Ser Gln Arg Tyr Gly Ala Asp Ala Ala Ser Glu
            20                  25                  30
Ala Leu Asp Pro His Ala Phe His Leu Leu Asn Thr Tyr Gly Arg
        35                  40                  45
Pro Ile Arg Phe Leu Arg Glu Asn Thr Thr Gln Cys Thr Tyr Asn Ser
    50                  55                  60
Ser Leu Arg Asn Ser Thr Val Val Arg Glu Asn Ala Ile Ser Phe Asn
65                  70                  75                  80
Phe Phe Gln Ser Tyr Asn Gln Tyr Tyr Val Phe His Met Pro Arg Cys
                85                  90                  95
Leu Phe Ala Gly Pro Leu Ala Glu Gln Phe Leu Asn Gln Val Asp Leu
            100                 105                 110
Thr Glu Thr Leu Glu Arg Tyr Gln Gln Arg Leu Asn Thr Tyr Ala Leu
        115                 120                 125
Val Ser Lys Asp Leu Ala Ser Tyr Arg Ser Phe Ser Gln Gln Leu Lys
    130                 135                 140
Ala Gln Asp Ser Leu Gly Gln Gln Pro Thr Thr Val Pro Pro Pro Ile
145                 150                 155                 160
Asp Leu Ser Ile Pro His Val Trp Met Pro Pro Gln Thr Thr Pro His
                165                 170                 175
Asp Trp Lys Gly Ser His Thr Thr Ser Gly Leu His Arg Pro His Phe
            180                 185                 190
Asn Gln Thr Cys Ile Leu Phe Asp Gly His Asp Leu Leu Phe Ser Thr
        195                 200                 205
Val Thr Pro Cys Leu His Gln Gly Phe Tyr Leu Met Asp Glu Leu Arg
    210                 215                 220
Tyr Val Lys Ile Thr Leu Thr Glu Asp Phe Phe Val Val Thr Val Ser
225                 230                 235                 240
Ile Asp Asp Asp Thr Pro Met Leu Leu Ile Phe Gly His Leu Pro Arg
                245                 250                 255
Val Leu Phe Lys Ala Pro Tyr Gln Arg Asp Asn Phe Ile Leu Arg Gln
            260                 265                 270
Thr Glu Lys His Glu Leu Leu Val Leu Val Lys Lys Ala Gln Leu Asn
        275                 280                 285
Arg His Ser Tyr Leu Lys Asp Ser Asp Phe Leu Asp Ala Ala Leu Asp
    290                 295                 300
Phe Asn Tyr Leu Asp Leu Ser Ala Leu Leu Arg Asn Ser Phe His Arg
305                 310                 315                 320
Tyr Ala Val Asp Val Leu Lys Ser Gly Arg Cys Gln Met Leu Asp Arg
                325                 330                 335
Arg Thr Val Glu Met Ala Phe Ala Tyr Ala Leu Ala Leu Phe Ala Ala
            340                 345                 350
Ala Arg Gln Glu Glu Ala Gly Thr Glu Ile Ser Ile Pro Arg Ala Leu
        355                 360                 365
Asp Arg Gln Ala Ala Leu Leu Gln Ile Gln Glu Phe Met Ile Thr Cys
    370                 375                 380
Leu Ser Gln Thr Pro Pro Arg Thr Thr Leu Leu Leu Tyr Pro Thr Ala
385                 390                 395                 400
```

```
Val Asp Leu Ala Lys Arg Ala Leu Trp Thr Pro Asp Gln Ile Thr Asp
                405                 410                 415

Ile Thr Ser Leu Val Arg Leu Val Tyr Ile Leu Ser Lys Gln Asn Gln
            420                 425                 430

Gln His Leu Ile Pro Gln Trp Ala Leu Arg Gln Ile Ala Asp Phe Ala
        435                 440                 445

Leu Gln Leu His Lys Thr His Leu Ala Ser Phe Leu Ser Ala Phe Ala
    450                 455                 460

Arg Gln Glu Leu Tyr Leu Met Gly Ser Leu Val His Ser Met Leu Val
465                 470                 475                 480

His Thr Thr Glu Arg Arg Glu Ile Phe Ile Val Glu Thr Gly Leu Cys
                485                 490                 495

Ser Leu Ala Glu Leu Ser His Phe Thr Gln Leu Leu Ala His Pro His
            500                 505                 510

His Glu Tyr Leu Ser Asp Leu Tyr Thr Pro Cys Ser Ser Gly Arg
        515                 520                 525

Arg Asp His Ser Leu Glu Arg Leu Thr Arg Leu Phe Pro Asp Ala Thr
    530                 535                 540

Val Pro Ala Thr Val Pro Ala Ala Leu Ser Ile Leu Ser Thr Met Gln
545                 550                 555                 560

Pro Ser Thr Leu Glu Thr Phe Pro Asp Leu Phe Cys Leu Pro Leu Gly
                565                 570                 575

Glu Ser Phe Ser Ala Leu Thr Val Ser Glu His Val Ser Tyr Val Val
            580                 585                 590

Thr Asn Gln Tyr Leu Ile Lys Gly Ile Ser Tyr Pro Val Ser Thr Thr
        595                 600                 605

Val Val Gly Gln Ser Leu Ile Ile Thr Gln Thr Asp Ser Gln Thr Lys
    610                 615                 620

Cys Glu Leu Thr Arg Asn Met His Thr Thr His Ser Ile Thr Ala Ala
625                 630                 635                 640

Leu Asn Ile Ser Leu Glu Asn Cys Ala Phe Cys Gln Ser Ala Leu Leu
                645                 650                 655

Glu Tyr Asp Asp Thr Gln Gly Val Ile Asn Ile Met Tyr Met His Asp
            660                 665                 670

Ser Asp Asp Val Leu Phe Ala Leu Asp Pro Tyr Asn Glu Val Val Val
        675                 680                 685

Ser Ser Pro Arg Thr His Tyr Leu Met Leu Leu Lys Asn Gly Thr Val
    690                 695                 700

Leu Glu Val Thr Asp Val Val Asp Ala Thr Asp Ser Arg Leu Leu
705                 710                 715                 720

Met Met Ser Val Tyr Ala Leu Ser Ala Ile Ile Gly Ile Tyr Leu Leu
                725                 730                 735

Tyr Arg Met Leu Lys Thr Cys
            740

<210> SEQ ID NO 4
<211> LENGTH: 715
<212> TYPE: PRT
<213> ORGANISM: Human herpesvirus 5
<220> FEATURE:
<221> NAME/KEY: MISC_FEATURE
<222> LOCATION: (1)..(715)
<223> OTHER INFORMATION: /note="Strain Merlin"

<400> SEQUENCE: 4

Met Arg Pro Gly Leu Pro Ser Tyr Leu Ile Ile Leu Ala Val Cys Leu
```

```
  1               5                    10                   15
Phe Ser His Leu Leu Ser Ser Arg Tyr Gly Ala Glu Ala Val Ser Glu
             20                  25                  30

Pro Leu Asp Lys Ala Phe His Leu Leu Asn Thr Tyr Gly Arg Pro
             35                  40                  45

Ile Arg Phe Leu Arg Glu Asn Thr Thr Gln Cys Thr Tyr Asn Ser Ser
 50                  55                  60

Leu Arg Asn Ser Thr Val Val Arg Glu Asn Ala Ile Ser Phe Asn Phe
 65                  70                  75                  80

Phe Gln Ser Tyr Asn Gln Tyr Val Phe His Met Pro Arg Cys Leu
             85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
            115                 120                 125

Ser Lys Asp Leu Ala Ser Tyr Arg Ser Phe Ser Gln Gln Leu Lys Ala
130                 135                 140

Gln Asp Ser Leu Gly Glu Gln Pro Thr Thr Val Pro Pro Ile Asp
145                 150                 155                 160

Leu Ser Ile Pro His Val Trp Met Pro Pro Gln Thr Pro His Gly
            165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
            195                 200                 205

Thr Pro Cys Leu His Gln Gly Phe Tyr Leu Ile Asp Glu Leu Arg Tyr
210                 215                 220

Val Lys Ile Thr Leu Thr Glu Asp Phe Val Val Thr Val Ser Ile
225                 230                 235                 240

Asp Asp Asp Thr Pro Met Leu Leu Ile Phe Gly His Leu Pro Arg Val
            245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
            275                 280                 285

His Ser Tyr Leu Lys Asp Pro Asp Phe Leu Asp Ala Ala Leu Asp Phe
            290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
            325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
            355                 360                 365

Arg Gln Ala Ala Leu Leu Gln Ile Gln Glu Phe Met Ile Thr Cys Leu
            370                 375                 380

Ser Gln Thr Pro Pro Arg Thr Thr Leu Leu Tyr Pro Thr Ala Val
385                 390                 395                 400

Asp Leu Ala Lys Arg Ala Leu Trp Thr Pro Asn Gln Ile Thr Asp Ile
            405                 410                 415

Thr Ser Leu Val Arg Leu Val Tyr Ile Leu Ser Lys Gln Asn Gln Gln
            420                 425                 430
```

```
His Leu Ile Pro Gln Trp Ala Leu Arg Gln Ile Ala Asp Phe Ala Leu
            435                 440                 445
Lys Leu His Lys Thr His Leu Ala Ser Phe Leu Ser Ala Phe Ala Arg
        450                 455                 460
Gln Glu Leu Tyr Leu Met Gly Ser Leu Val His Ser Met Leu Val His
465                 470                 475                 480
Thr Thr Glu Arg Arg Glu Ile Phe Ile Val Glu Thr Gly Leu Cys Ser
                485                 490                 495
Leu Ala Glu Leu Ser His Phe Thr Gln Leu Leu Ala His Pro His His
            500                 505                 510
Glu Tyr Leu Ser Asp Leu Tyr Thr Pro Cys Ser Ser Gly Arg Arg
        515                 520                 525
Asp His Ser Leu Glu Arg Leu Thr Arg Leu Phe Pro Asp Ala Thr Val
    530                 535                 540
Pro Ala Thr Val Pro Ala Ala Leu Ser Ile Leu Ser Thr Met Gln Pro
545                 550                 555                 560
Ser Thr Leu Glu Thr Phe Pro Asp Leu Phe Cys Leu Pro Leu Gly Glu
                565                 570                 575
Ser Phe Ser Ala Leu Thr Val Ser Glu His Val Ser Tyr Ile Val Thr
            580                 585                 590
Asn Gln Tyr Leu Ile Lys Gly Ile Ser Tyr Pro Val Ser Thr Thr Val
        595                 600                 605
Val Gly Gln Ser Leu Ile Ile Thr Gln Thr Asp Ser Gln Thr Lys Cys
    610                 615                 620
Glu Leu Thr Arg Asn Met His Thr Thr His Ser Ile Thr Val Ala Leu
625                 630                 635                 640
Asn Ile Ser Leu Glu Asn Cys Ala Phe Cys Gln Ser Ala Leu Leu Glu
                645                 650                 655
Tyr Asp Asp Thr Gln Gly Val Ile Asn Ile Met Tyr Met His Asp Ser
            660                 665                 670
Asp Asp Val Leu Phe Ala Leu Asp Pro Tyr Asn Glu Val Val Val Ser
        675                 680                 685
Ser Pro Arg Thr His Tyr Leu Met Leu Leu Lys Asn Gly Thr Val Leu
    690                 695                 700
Glu Val Thr Asp Val Val Val Asp Ala Thr Asp
705                 710                 715

<210> SEQ ID NO 5
<211> LENGTH: 692
<212> TYPE: PRT
<213> ORGANISM: Human herpesvirus 5
<220> FEATURE:
<221> NAME/KEY: MISC_FEATURE
<222> LOCATION: (1)..(692)
<223> OTHER INFORMATION: /note="Strain Merlin"

<400> SEQUENCE: 5

Arg Tyr Gly Ala Glu Ala Val Ser Glu Pro Leu Asp Lys Ala Phe His
1               5                   10                  15
Leu Leu Leu Asn Thr Tyr Gly Arg Pro Ile Arg Phe Leu Arg Glu Asn
            20                  25                  30
Thr Thr Gln Cys Thr Tyr Asn Ser Ser Leu Arg Asn Ser Thr Val Val
        35                  40                  45
Arg Glu Asn Ala Ile Ser Phe Asn Phe Phe Gln Ser Tyr Asn Gln Tyr
    50                  55                  60
```

Tyr Val Phe His Met Pro Arg Cys Leu Phe Ala Gly Pro Leu Ala Glu
65                  70                  75                  80

Gln Phe Leu Asn Gln Val Asp Leu Thr Glu Thr Leu Glu Arg Tyr Gln
                85                  90                  95

Gln Arg Leu Asn Thr Tyr Ala Leu Val Ser Lys Asp Leu Ala Ser Tyr
            100                 105                 110

Arg Ser Phe Ser Gln Gln Leu Lys Ala Gln Asp Ser Leu Gly Glu Gln
        115                 120                 125

Pro Thr Val Pro Pro Ile Asp Leu Ser Ile Pro His Val Trp
    130                 135                 140

Met Pro Pro Gln Thr Thr Pro His Gly Trp Thr Glu Ser His Thr Thr
145                 150                 155                 160

Ser Gly Leu His Arg Pro His Phe Asn Gln Thr Cys Ile Leu Phe Asp
                165                 170                 175

Gly His Asp Leu Leu Phe Ser Thr Val Thr Pro Cys Leu His Gln Gly
            180                 185                 190

Phe Tyr Leu Ile Asp Glu Leu Arg Tyr Val Lys Ile Thr Leu Thr Glu
        195                 200                 205

Asp Phe Phe Val Thr Val Ser Ile Asp Asp Thr Pro Met Leu
    210                 215                 220

Leu Ile Phe Gly His Leu Pro Arg Val Leu Phe Lys Ala Pro Tyr Gln
225                 230                 235                 240

Arg Asp Asn Phe Ile Leu Arg Gln Thr Glu Lys His Glu Leu Leu Val
                245                 250                 255

Leu Val Lys Lys Asp Gln Leu Asn Arg His Ser Tyr Leu Lys Asp Pro
            260                 265                 270

Asp Phe Leu Asp Ala Ala Leu Asp Phe Asn Tyr Leu Asp Leu Ser Ala
        275                 280                 285

Leu Leu Arg Asn Ser Phe His Arg Tyr Ala Val Asp Val Leu Lys Ser
    290                 295                 300

Gly Arg Cys Gln Met Leu Asp Arg Arg Thr Val Glu Met Ala Phe Ala
305                 310                 315                 320

Tyr Ala Leu Ala Leu Phe Ala Ala Ala Arg Gln Glu Glu Ala Gly Ala
                325                 330                 335

Gln Val Ser Val Pro Arg Ala Leu Asp Arg Gln Ala Ala Leu Leu Gln
            340                 345                 350

Ile Gln Glu Phe Met Ile Thr Cys Leu Ser Gln Thr Pro Arg Thr
        355                 360                 365

Thr Leu Leu Leu Tyr Pro Thr Ala Val Asp Leu Ala Lys Arg Ala Leu
    370                 375                 380

Trp Thr Pro Asn Gln Ile Thr Asp Ile Thr Ser Leu Val Arg Leu Val
385                 390                 395                 400

Tyr Ile Leu Ser Lys Gln Asn Gln Gln His Leu Ile Pro Gln Trp Ala
                405                 410                 415

Leu Arg Gln Ile Ala Asp Phe Ala Leu Lys Leu His Lys Thr His Leu
            420                 425                 430

Ala Ser Phe Leu Ser Ala Phe Ala Arg Gln Glu Leu Tyr Leu Met Gly
        435                 440                 445

Ser Leu Val His Ser Met Leu Val His Thr Thr Glu Arg Arg Glu Ile
    450                 455                 460

Phe Ile Val Glu Thr Gly Leu Cys Ser Leu Ala Glu Leu Ser His Phe
465                 470                 475                 480

Thr Gln Leu Leu Ala His Pro His His Glu Tyr Leu Ser Asp Leu Tyr

```
                    485                 490                 495

Thr Pro Cys Ser Ser Gly Arg Arg Asp His Ser Leu Glu Arg Leu
            500                 505                 510

Thr Arg Leu Phe Pro Asp Ala Thr Val Pro Ala Thr Val Pro Ala Ala
        515                 520                 525

Leu Ser Ile Leu Ser Thr Met Gln Pro Ser Thr Leu Glu Thr Phe Pro
    530                 535                 540

Asp Leu Phe Cys Leu Pro Leu Gly Glu Ser Phe Ser Ala Leu Thr Val
545                 550                 555                 560

Ser Glu His Val Ser Tyr Ile Val Thr Asn Gln Tyr Leu Ile Lys Gly
                565                 570                 575

Ile Ser Tyr Pro Val Ser Thr Val Val Gly Gln Ser Leu Ile Ile
                580                 585                 590

Thr Gln Thr Asp Ser Gln Thr Lys Cys Glu Leu Thr Arg Asn Met His
            595                 600                 605

Thr Thr His Ser Ile Thr Val Ala Leu Asn Ile Ser Leu Glu Asn Cys
        610                 615                 620

Ala Phe Cys Gln Ser Ala Leu Leu Glu Tyr Asp Asp Thr Gln Gly Val
625                 630                 635                 640

Ile Asn Ile Met Tyr Met His Asp Ser Asp Val Leu Phe Ala Leu
                645                 650                 655

Asp Pro Tyr Asn Glu Val Val Val Ser Ser Pro Arg Thr His Tyr Leu
                660                 665                 670

Met Leu Leu Lys Asn Gly Thr Val Leu Glu Val Thr Asp Val Val Val
            675                 680                 685

Asp Ala Thr Asp
        690

<210> SEQ ID NO 6
<211> LENGTH: 278
<212> TYPE: PRT
<213> ORGANISM: Human herpesvirus 5
<220> FEATURE:
<221> NAME/KEY: MISC_FEATURE
<222> LOCATION: (1)..(278)
<223> OTHER INFORMATION: /note="Strain Merlin"

<400> SEQUENCE: 6

Met Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
                20                  25                  30

Val Ser Val Ala Pro Thr Ala Ala Glu Lys Val Pro Ala Glu Cys Pro
            35                  40                  45

Glu Leu Thr Arg Arg Cys Leu Leu Gly Glu Val Phe Glu Gly Asp Lys
        50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140
```

Gly Asp Gly Ser Pro Ala Val Tyr Thr Cys Val Asp Leu Cys Arg
145                 150                 155                 160

Gly Tyr Asp Leu Thr Arg Leu Ser Tyr Gly Arg Ser Ile Phe Thr Glu
            165                 170                 175

His Val Leu Gly Phe Glu Leu Val Pro Pro Ser Leu Phe Asn Val Val
        180                 185                 190

Val Ala Ile Arg Asn Glu Ala Thr Arg Thr Asn Arg Ala Val Arg Leu
            195                 200                 205

Pro Val Ser Thr Ala Ala Pro Glu Gly Ile Thr Leu Phe Tyr Gly
210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
            245                 250                 255

Leu Lys Gln Thr Arg Val Asn Leu Pro Ala His Ser Arg Tyr Gly Pro
            260                 265                 270

Gln Ala Val Asp Ala Arg
            275

<210> SEQ ID NO 7
<211> LENGTH: 278
<212> TYPE: PRT
<213> ORGANISM: Human herpesvirus 5
<220> FEATURE:
<221> NAME/KEY: MISC_FEATURE
<222> LOCATION: (1)..(278)
<223> OTHER INFORMATION: /note="Strain Towne"

<400> SEQUENCE: 7

Met Cys Arg Arg Pro Asp Cys Gly Phe Ser Phe Ser Pro Gly Pro Val
1               5                   10                  15

Ala Leu Leu Trp Cys Cys Leu Leu Pro Ile Val Ser Ser Ala Thr
            20                  25                  30

Val Ser Val Ala Pro Thr Val Ala Glu Lys Val Pro Ala Glu Cys Pro
            35                  40                  45

Glu Leu Thr Arg Arg Cys Leu Leu Gly Glu Val Phe Gln Gly Asp Lys
50                  55                  60

Tyr Glu Ser Trp Leu Arg Pro Leu Val Asn Val Thr Arg Arg Asp Gly
65                  70                  75                  80

Pro Leu Ser Gln Leu Ile Arg Tyr Arg Pro Val Thr Pro Glu Ala Ala
            85                  90                  95

Asn Ser Val Leu Leu Asp Asp Ala Phe Leu Asp Thr Leu Ala Leu Leu
            100                 105                 110

Tyr Asn Asn Pro Asp Gln Leu Arg Ala Leu Leu Thr Leu Leu Ser Ser
            115                 120                 125

Asp Thr Ala Pro Arg Trp Met Thr Val Met Arg Gly Tyr Ser Glu Cys
130                 135                 140

Gly Asp Gly Ser Pro Ala Val Tyr Thr Cys Val Asp Leu Cys Arg
145                 150                 155                 160

Gly Tyr Asp Leu Thr Arg Leu Ser Tyr Gly Arg Ser Ile Phe Thr Glu
            165                 170                 175

His Val Leu Gly Phe Glu Leu Val Pro Pro Ser Leu Phe Asn Val Val
        180                 185                 190

Val Ala Ile Arg Asn Glu Ala Thr Arg Thr Asn Arg Ala Val Arg Leu
            195                 200                 205

Pro Val Ser Thr Ala Ala Ala Pro Glu Gly Ile Thr Leu Phe Tyr Gly
            210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
            275

<210> SEQ ID NO 8
<211> LENGTH: 278
<212> TYPE: PRT
<213> ORGANISM: Human herpesvirus 5
<220> FEATURE:
<221> NAME/KEY: MISC_FEATURE
<222> LOCATION: (1)..(278)
<223> OTHER INFORMATION: /note="Strain AD169"

<400> SEQUENCE: 8

Met Cys Arg Arg Pro Asp Cys Gly Phe Ser Phe Ser Pro Gly Pro Val
1               5                   10                  15

Val Leu Leu Trp Cys Cys Leu Leu Pro Ile Val Ser Ser Val Ala
            20                  25                  30

Val Ser Val Ala Pro Thr Ala Ala Glu Lys Val Pro Ala Glu Cys Pro
            35                  40                  45

Glu Leu Thr Arg Arg Cys Leu Leu Gly Glu Val Phe Gln Gly Asp Lys
50                  55                  60

Tyr Glu Ser Trp Leu Arg Pro Leu Val Asn Val Thr Arg Arg Asp Gly
65                  70                  75                  80

Pro Leu Ser Gln Leu Ile Arg Tyr Arg Pro Val Thr Pro Glu Ala Ala
            85                  90                  95

Asn Ser Val Leu Leu Asp Asp Ala Phe Leu Asp Thr Leu Ala Leu Leu
            100                 105                 110

Tyr Asn Asn Pro Asp Gln Leu Arg Ala Leu Leu Thr Leu Leu Ser Ser
            115                 120                 125

Asp Thr Ala Pro Arg Trp Met Thr Val Met Arg Gly Tyr Ser Glu Cys
130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
            195                 200                 205

Pro Val Ser Thr Ala Ala Ala Pro Glu Gly Ile Thr Leu Phe Tyr Gly
            210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg

```
                                    275

<210> SEQ ID NO 9
<211> LENGTH: 248
<212> TYPE: PRT
<213> ORGANISM: Human herpesvirus 5
<220> FEATURE:
<221> NAME/KEY: MISC_FEATURE
<222> LOCATION: (1)..(248)
<223> OTHER INFORMATION: /note="Strain Merlin"

<400> SEQUENCE: 9

Ala Ala Val Ser Val Ala Pro Thr Ala Ala Glu Lys Val Pro Ala Glu
1               5                   10                  15

Cys Pro Glu Leu Thr Arg Arg Cys Leu Leu Gly Glu Val Phe Glu Gly
                20                  25                  30

Asp Lys Tyr Glu Ser Trp Leu Arg Pro Leu Val Asn Val Thr Gly Arg
            35                  40                  45

Asp Gly Pro Leu Ser Gln Leu Ile Arg Tyr Arg Pro Val Thr Pro Glu
        50                  55                  60

Ala Ala Asn Ser Val Leu Leu Asp Glu Ala Phe Leu Asp Thr Leu Ala
65                  70                  75                  80

Leu Leu Tyr Asn Asn Pro Asp Gln Leu Arg Ala Leu Leu Thr Leu Leu
                85                  90                  95

Ser Ser Asp Thr Ala Pro Arg Trp Met Thr Val Met Arg Gly Tyr Ser
                100                 105                 110

Glu Cys Gly Asp Gly Ser Pro Ala Val Tyr Thr Cys Val Asp Asp Leu
            115                 120                 125

Cys Arg Gly Tyr Asp Leu Thr Arg Leu Ser Tyr Gly Arg Ser Ile Phe
        130                 135                 140

Thr Glu His Val Leu Gly Phe Glu Leu Val Pro Pro Ser Leu Phe Asn
145                 150                 155                 160

Val Val Val Ala Ile Arg Asn Glu Ala Thr Arg Thr Asn Arg Ala Val
                165                 170                 175

Arg Leu Pro Val Ser Thr Ala Ala Pro Glu Gly Ile Thr Leu Phe
                180                 185                 190

Tyr Gly Leu Tyr Asn Ala Val Lys Glu Phe Cys Leu Arg His Gln Leu
            195                 200                 205

Asp Pro Pro Leu Leu Arg His Leu Asp Lys Tyr Tyr Ala Gly Leu Pro
        210                 215                 220

Pro Glu Leu Lys Gln Thr Arg Val Asn Leu Pro Ala His Ser Arg Tyr
225                 230                 235                 240

Gly Pro Gln Ala Val Asp Ala Arg
                245

<210> SEQ ID NO 10
<211> LENGTH: 130
<212> TYPE: PRT
<213> ORGANISM: Human herpesvirus 5
<220> FEATURE:
<221> NAME/KEY: MISC_FEATURE
<222> LOCATION: (1)..(130)
<223> OTHER INFORMATION: /note="Strain Merlin"

<400> SEQUENCE: 10

Met Ser Pro Lys Asp Leu Thr Pro Phe Leu Thr Ala Leu Trp Leu Leu
1               5                   10                  15

Leu Gly His Ser Arg Val Pro Arg Val Arg Ala Glu Glu Cys Cys Glu
                20                  25                  30
```

Phe Ile Asn Val Asn His Pro Pro Glu Arg Cys Tyr Asp Phe Lys Met
                35                  40                  45

Cys Asn Arg Phe Thr Val Ala Leu Arg Cys Pro Asp Gly Glu Val Cys
 50                  55                  60

Tyr Ser Pro Glu Lys Thr Ala Glu Ile Arg Gly Ile Val Thr Thr Met
 65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
                100                 105                 110

Lys Val Asn Asp Lys Ala Gln Tyr Leu Leu Gly Ala Ala Gly Ser Val
                115                 120                 125

Pro Tyr
   130

<210> SEQ ID NO 11
<211> LENGTH: 171
<212> TYPE: PRT
<213> ORGANISM: Human herpesvirus 5
<220> FEATURE:
<221> NAME/KEY: MISC_FEATURE
<222> LOCATION: (1)..(171)
<223> OTHER INFORMATION: /note="Strain Towne"

<400> SEQUENCE: 11

Met Ser Pro Lys Asn Leu Thr Pro Phe Leu Thr Ala Leu Trp Leu Leu
 1               5                  10                  15

Leu Gly His Ser Arg Val Pro Arg Val Arg Ala Glu Glu Cys Cys Glu
                20                  25                  30

Phe Ile Asn Val Asn His Pro Pro Glu Arg Cys Tyr Asp Phe Lys Met
                35                  40                  45

Cys Asn Arg Phe Thr Val Ala Leu Arg Cys Pro Asp Gly Glu Val Cys
 50                  55                  60

Tyr Ser Pro Glu Lys Thr Ala Glu Ile Arg Gly Ile Val Thr Thr Met
 65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
                100                 105                 110

Lys Val Asn Asp Lys Ala Gln Tyr Leu Leu Gly Ala Ala Gly Ser Val
                115                 120                 125

Pro Tyr Arg Trp Ile Asn Leu Glu Tyr Asp Lys Ile Thr Arg Ile Val
                130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170

<210> SEQ ID NO 12
<211> LENGTH: 171
<212> TYPE: PRT
<213> ORGANISM: Human herpesvirus 5
<220> FEATURE:
<221> NAME/KEY: MISC_FEATURE
<222> LOCATION: (1)..(171)
<223> OTHER INFORMATION: /note="Strain AD169"

<400> SEQUENCE: 12

```
Met Ser Pro Lys Asp Leu Thr Pro Phe Leu Thr Thr Leu Trp Leu Leu
 1               5                  10                  15

Leu Gly His Ser Arg Val Pro Arg Val Arg Ala Glu Glu Cys Cys Glu
             20                  25                  30

Phe Ile Asn Val Asn His Pro Pro Glu Arg Cys Tyr Asp Phe Lys Met
         35                  40                  45

Cys Asn Arg Phe Thr Val Ala Leu Arg Cys Pro Asp Gly Glu Val Cys
 50                  55                  60

Tyr Ser Pro Glu Lys Thr Ala Glu Ile Arg Gly Ile Val Thr Thr Met
 65                  70                  75                  80

Thr His Ser Leu Thr Arg Gln Val Val His Asn Lys Leu Thr Ser Cys
                 85                  90                  95

Asn Tyr Asn Pro Leu Tyr Leu Glu Ala Asp Gly Arg Ile Arg Cys Gly
             100                 105                 110

Lys Val Asn Asp Lys Ala Gln Tyr Leu Leu Gly Ala Ala Gly Ser Val
             115                 120                 125

Pro Tyr Arg Trp Ile Asn Leu Glu Tyr Asp Lys Ile Thr Arg Ile Val
         130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                 165                 170

<210> SEQ ID NO 13
<211> LENGTH: 144
<212> TYPE: PRT
<213> ORGANISM: Human herpesvirus 5

<400> SEQUENCE: 13

Glu Glu Cys Cys Glu Phe Ile Asn Val Asn His Pro Pro Glu Arg Cys
 1               5                  10                  15

Tyr Asp Phe Lys Met Cys Asn Arg Phe Thr Val Ala Leu Arg Cys Pro
             20                  25                  30

Asp Gly Glu Val Cys Tyr Ser Pro Glu Lys Thr Ala Glu Ile Arg Gly
         35                  40                  45

Ile Val Thr Thr Met Thr His Ser Leu Thr Arg Gln Val Val His Asn
 50                  55                  60

Lys Leu Thr Ser Cys Asn Tyr Asn Pro Leu Tyr Leu Glu Ala Asp Gly
 65                  70                  75                  80

Arg Ile Arg Cys Gly Lys Val Asn Asp Lys Ala Gln Tyr Leu Leu Gly
                 85                  90                  95

Ala Ala Gly Ser Val Pro Tyr Arg Trp Ile Asn Leu Glu Tyr Asp Lys
             100                 105                 110

Ile Thr Arg Ile Val Gly Leu Asp Gln Tyr Leu Glu Ser Val Lys Lys
             115                 120                 125

His Lys Arg Leu Asp Val Cys Arg Ala Lys Met Gly Tyr Met Leu Gln
         130                 135                 140

<210> SEQ ID NO 14
<211> LENGTH: 214
<212> TYPE: PRT
<213> ORGANISM: Human herpesvirus 5
<220> FEATURE:
<221> NAME/KEY: MISC_FEATURE
<222> LOCATION: (1)..(214)
<223> OTHER INFORMATION: /note="Strain Merlin"

<400> SEQUENCE: 14
```

```
Met Leu Arg Leu Leu Arg His His Phe His Cys Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
            35                  40                  45

Pro His Asp Ala Ala Thr Phe Tyr Cys Pro Phe Leu Tyr Pro Ser Pro
50                      55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
                100                 105                 110

Tyr Leu Ser Gly Arg Asn Gln Thr Ile Leu Gln Arg Met Pro Arg Thr
            115                 120                 125

Ala Ser Lys Pro Ser Asp Gly Asn Val Gln Ile Ser Val Glu Asp Ala
130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
            195                 200                 205

His Pro Asn Leu Ile Val
            210
```

<210> SEQ ID NO 15
<211> LENGTH: 229
<212> TYPE: PRT
<213> ORGANISM: Human herpesvirus 5
<220> FEATURE:
<221> NAME/KEY: MISC_FEATURE
<222> LOCATION: (1)..(229)
<223> OTHER INFORMATION: /note="Strain Towne"

<400> SEQUENCE: 15

```
Met Leu Arg Leu Leu Arg His His Phe His Cys Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
            35                  40                  45

Pro His Asp Ala Ala Thr Phe Tyr Cys Pro Phe Leu Tyr Pro Ser Pro
50                      55                  60

Pro Arg Ser Pro Leu Gln Phe Ser Gly Phe Gln Arg Val Leu Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
                100                 105                 110

Tyr Leu Ser Gly Arg Asn Gln Thr Ile Leu Gln Arg Met Pro Arg Thr
            115                 120                 125
```

```
Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Phe Thr Pro Ser Ala
        195                 200                 205

Pro Ile Pro Ile Ser Ser Phe Glu Pro Val Ala Arg Ala Gly Asn Phe
    210                 215                 220

Glu Asn Arg Ala Ser
225

<210> SEQ ID NO 16
<211> LENGTH: 189
<212> TYPE: PRT
<213> ORGANISM: Human herpesvirus 5
<220> FEATURE:
<221> NAME/KEY: MISC_FEATURE
<222> LOCATION: (1)..(189)
<223> OTHER INFORMATION: /note="Strain Merlin"

<400> SEQUENCE: 16

Ser Pro Trp Ser Thr Leu Thr Ala Asn Gln Asn Pro Ser Pro Trp
1               5                   10                  15

Ser Lys Leu Thr Tyr Ser Lys Pro His Asp Ala Ala Thr Phe Tyr Cys
                20                  25                  30

Pro Phe Leu Tyr Pro Ser Pro Arg Ser Pro Leu Gln Phe Ser Gly
            35                  40                  45

Phe Gln Arg Val Ser Thr Gly Pro Glu Cys Arg Asn Glu Thr Leu Tyr
        50                  55                  60

Leu Leu Tyr Asn Arg Glu Gly Gln Thr Leu Val Glu Arg Ser Ser Thr
65                  70                  75                  80

Trp Val Lys Lys Val Ile Trp Tyr Leu Ser Gly Arg Asn Gln Thr Ile
                85                  90                  95

Leu Gln Arg Met Pro Arg Thr Ala Ser Lys Pro Ser Asp Gly Asn Val
                100                 105                 110

Gln Ile Ser Val Glu Asp Ala Lys Ile Phe Gly Ala His Met Val Pro
            115                 120                 125

Lys Gln Thr Lys Leu Leu Arg Phe Val Val Asn Asp Gly Thr Arg Tyr
130                 135                 140

Gln Met Cys Val Met Lys Leu Glu Ser Trp Ala His Val Phe Arg Asp
145                 150                 155                 160

Tyr Ser Val Ser Phe Gln Val Arg Leu Thr Phe Thr Glu Ala Asn Asn
                165                 170                 175

Gln Thr Tyr Thr Phe Cys Thr His Pro Asn Leu Ile Val
            180                 185

<210> SEQ ID NO 17
<211> LENGTH: 129
<212> TYPE: PRT
<213> ORGANISM: Human herpesvirus 5
<220> FEATURE:
<221> NAME/KEY: MISC_FEATURE
<222> LOCATION: (1)..(129)
<223> OTHER INFORMATION: /note="Strain Merlin"
```

<400> SEQUENCE: 17

```
Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn
```

<210> SEQ ID NO 18
<211> LENGTH: 129
<212> TYPE: PRT
<213> ORGANISM: Human herpesvirus 5
<220> FEATURE:
<221> NAME/KEY: MISC_FEATURE
<222> LOCATION: (1)..(129)
<223> OTHER INFORMATION: /note="Strain Towne"

<400> SEQUENCE: 18

```
Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn
```

<210> SEQ ID NO 19
<211> LENGTH: 74
<212> TYPE: PRT
<213> ORGANISM: Human herpesvirus 5
<220> FEATURE:
<221> NAME/KEY: MISC_FEATURE
<222> LOCATION: (1)..(74)
<223> OTHER INFORMATION: /note="Strain AD169"

<400> SEQUENCE: 19

Met Arg Leu Cys Arg Val Trp Leu Ser Val Cys Leu Cys Ala Val Val

```
                1               5              10              15
            Leu Gly Gln Cys Gln Arg Glu Thr Ala Glu Lys Lys Arg Leu Leu Pro
                           20                  25                  30

Ser Thr Ala Leu Leu Gly Arg Val Leu Ser Arg Ala Ala Arg Pro Asn
                           35                  40                  45

Pro Leu Gln Val Cys Gly Thr Ala Arg Gly Pro His Val Glu Leu Pro
                           50                  55                  60

Leu Arg Cys Glu Pro Arg Leu Gly Gln Leu
            65                  70

<210> SEQ ID NO 20
            <211> LENGTH: 111
            <212> TYPE: PRT
            <213> ORGANISM: Human herpesvirus 5

<400> SEQUENCE: 20

Gln Cys Gln Arg Glu Thr Ala Glu Lys Asn Asp Tyr Tyr Arg Val Pro
            1               5                  10                  15

His Tyr Trp Asp Ala Cys Ser Arg Ala Leu Pro Asp Gln Thr Arg Tyr
                           20                  25                  30

Lys Tyr Val Glu Gln Leu Val Asp Leu Thr Leu Asn Tyr His Tyr Asp
                           35                  40                  45

Ala Ser His Gly Leu Asp Asn Phe Asp Val Leu Lys Arg Ile Asn Val
                           50                  55                  60

Thr Glu Val Ser Leu Leu Ile Ser Asp Phe Arg Arg Gln Asn Arg Arg
            65                  70                  75                  80

Gly Gly Thr Asn Lys Arg Thr Thr Phe Asn Ala Ala Gly Ser Leu Ala
                           85                  90                  95

Pro His Ala Arg Ser Leu Glu Phe Ser Val Arg Leu Phe Ala Asn
                          100                 105                 110

<210> SEQ ID NO 21
            <211> LENGTH: 1547
            <212> TYPE: PRT
            <213> ORGANISM: Cricetulus griseus

<400> SEQUENCE: 21

Met Asn Trp Asn Ala Lys Pro Glu Asn Ala Ala Pro Asn Pro Pro Tyr
            1               5                  10                  15

Ser Lys Ser Gln Ser Ser Leu Leu Gln Gln Phe Leu Met Pro Ser Thr
                           20                  25                  30

Thr Ser Gln Ser Ser Phe Ser Cys Leu Pro His Asn Gln Glu Ala Cys
                           35                  40                  45

Ile Tyr Pro Thr Asn Ser Asn Ser Val Ser Gln Pro Leu Leu Asn Val
                           50                  55                  60

Arg Ser Phe Ile Asn Pro Pro Ile Ser Val Ser Asn Val His Asn Arg
            65                  70                  75                  80

Thr Val Val Ala Ser Gln Thr Ser Val Glu Arg Val Thr Tyr Thr Asn
                           85                  90                  95

Val Lys Gly Ala Gln Gln Pro Asn His Asn Leu Gln Thr Val Ser Ser
                          100                 105                 110

Gly Val Val Gln Asn Ala Trp Met Asn Ser Thr Met Arg Asn Phe Met
                          115                 120                 125

Pro Ser Leu Thr Glu Ala Thr Ile Ser His Lys Pro Asp Gly Gly Pro
                          130                 135                 140

Ser Met Pro Tyr Met His Ala Pro Gln Ser His Leu Val Thr Ser Asp
```

```
            145                 150                 155                 160
        Thr Tyr Ser Val Gln Leu Gln Met Thr Pro Ser Asn Ser Val Arg Gly
                        165                 170                 175
        Pro Val Thr Tyr Gln Gly Asn Tyr Gln Gly Asn Pro Gly Leu Asn His
                        180                 185                 190
        Ser Met Ala Gly Glu Leu Gly Trp Val Gln Cys Ala Ser Ser Glu Leu
                        195                 200                 205
        Thr Tyr Pro Asp Tyr Arg Pro Pro Lys Gln Tyr Pro Tyr Leu Pro
                210                 215                 220
        Gln Ser Phe Val Gln Asp Thr Ser Val Gln Lys Gln Asn Phe Val Ser
        225                 230                 235                 240
        Ser Thr Ser Leu Gln Val Lys Asn Asn Gln Leu Pro Pro Ser Thr Gln
                        245                 250                 255
        Thr Leu Pro Ser Lys Arg Pro Val Pro Val Ser Ser Tyr Gln Tyr Ala
                        260                 265                 270
        Ala Glu Thr Ser Lys Arg Leu Pro Pro Pro Tyr Ser Cys Arg Tyr
                    275                 280                 285
        Gly Ser Gln His Val Gln Asn Ser Gln Ser Val Ser Arg His Leu Pro
                    290                 295                 300
        Val Glu Val Pro Gln Ser Ser Glu Met His Ser Ser Glu Lys Lys Lys
        305                 310                 315                 320
        Asp Ala Tyr Lys Val Phe Gln Gln Gln Trp Gln Ser Thr Ser Lys Asn
                        325                 330                 335
        Val Ser Thr Ile Gly Lys Phe Cys Glu Leu Lys Ile Asn Thr Lys Gln
                        340                 345                 350
        Ser Tyr Asn Asp Ser Ala Gly Ser Ser Gly Asp Gly Val His Thr Leu
                    355                 360                 365
        Val Gln Asn Asn Gln Glu Glu Arg Lys Tyr Ser Tyr Asn Pro Ser Thr
                    370                 375                 380
        Asn Gln Ile Leu Asp Thr Asn Val Thr Lys Glu Lys Leu Val Arg Asp
        385                 390                 395                 400
        Ile Lys Ser Leu Val Glu Ile Lys Lys Phe Ser Glu Leu Ala Arg
                        405                 410                 415
        Lys Ile Lys Ile Asn Lys Lys Leu Leu Met Ala Ala Gly Cys Ser Lys
                        420                 425                 430
        Thr Ala Asn Thr Ser Tyr Thr Glu Pro Thr Arg His Ser Glu Phe Ser
                        435                 440                 445
        Ala Lys Glu Met Ser Ala Lys Arg Asp Asn Gln Cys Ser Met Glu Leu
                    450                 455                 460
        Leu Ala Thr Cys Leu Ser Leu Trp Lys Asn Gln Pro Pro Lys Thr Thr
        465                 470                 475                 480
        Glu Glu Asn Val Ser Lys Pro Leu Glu Glu Lys Gln Tyr Asn Ala Ser
                        485                 490                 495
        Arg Thr Ser Thr Thr Ala Val Gly Pro Ser Asn Pro Met Asn Glu Val
                    500                 505                 510
        His Val Lys Asn Phe Cys Ser Gly Val Arg Asn Ser Gln Lys Ile Thr
                    515                 520                 525
        Thr Ser Ser Gln Thr Val Leu Ser Val Leu Thr Pro Val Tyr Asp Ser
                    530                 535                 540
        Ser Asp Val Ala Val Gly Lys Gly Thr Glu Leu Gln Ile Ala Val Val
        545                 550                 555                 560
        Ser Pro Leu Ile Leu Ser Asp Val Ser Thr Val Pro Gly Lys Glu Leu
                        565                 570                 575
```

```
Ala Pro Glu Val Val Ser Glu Thr Val Tyr Pro Val Lys Glu Gly
            580                 585                 590

Ser Val Cys Ser Leu Gln Asn Gln Gln Ala Glu Asn Ala Thr Val Thr
595                 600                 605

Ala Gly Leu Pro Phe Asp Val Ile Arg Ala Val Ala Ser Ala Thr Val
        610                 615                 620

Ser Ala Glu Leu Ser Leu Pro Gly His Lys Glu Lys Gln His Lys Pro
625                 630                 635                 640

Thr Gln Ser Asp Leu Asp Ile Ala Asp Gly Ser Leu Gly Lys His Ser
                645                 650                 655

Pro Gln Gly Ala Glu Ala Leu Pro Asn Pro Arg Asp Ser Thr Ile Val
            660                 665                 670

Ser Gly Pro Ile Leu Gln Ile Glu Ser Ile Cys Ser Leu Ala Glu Gly
        675                 680                 685

Asp Val Ser Tyr Asn Ser Gln Ile Ala Glu Ile Phe Asn Ser Val Gln
    690                 695                 700

Asn Glu Pro Gln Lys Pro Ser Pro Asp Gln Gln Val Ile Asn Ser Gln
705                 710                 715                 720

Gln Glu Glu Gln Val Asp Lys Val Ala Glu Asn Lys Asp Leu Ser Phe
                725                 730                 735

Leu Lys Asp Lys Cys Met Gln Cys Thr Asp Val Pro His Glu Val Thr
            740                 745                 750

Glu Gln Pro Glu Pro Leu Gln Pro Leu Glu Thr Thr Ser Asp Glu Tyr
        755                 760                 765

Val Glu Ala Asn Gly Glu Ile Leu Glu Glu Ser Ser Lys Glu Asn Pro
    770                 775                 780

Gly Glu Lys Glu Met Thr Lys Asp Ile Leu Cys Ser Pro Ala Ala Val
785                 790                 795                 800

Gln Gln Asp Pro Gln Pro Gln Glu Ile Asp Thr Ala Ser Ser Lys Ser
                805                 810                 815

Gly His Ser Phe Ser Thr Val Asn Glu Ile Asn Asp Glu Asn Glu Pro
            820                 825                 830

Val Ser Tyr Leu His Asp Gln Leu Leu Glu Leu Leu Lys Glu Phe Pro
        835                 840                 845

Tyr Gly Ile Glu Thr Ile Ala Arg Pro Glu Val Tyr Val Gly Gln Gln
    850                 855                 860

Lys Thr His Glu Ile Leu Glu Asn Gln Thr Gly Ser Lys Thr Gly Asn
865                 870                 875                 880

Val Ser Gly Asp Asn Thr Asp Gln Ile Lys Ile Thr Val Leu Asn Ser
                885                 890                 895

Glu Gln Ile Lys Glu Leu Phe Pro Glu Asp Gln Pro Cys Asp Val
            900                 905                 910

Asp Lys Leu Ala Glu Pro Glu Asn Thr Lys Ile Ile Ala Glu Val Lys
        915                 920                 925

Ser Leu Cys Asp Ser Gln Val Pro Arg Glu Glu Ser His Asn Pro Gly
    930                 935                 940

Met Leu Asp Leu Glu Lys Asp Lys Ile His Cys Cys Ala Leu Gly Trp
945                 950                 955                 960

Leu Ser Met Val Tyr Glu Gly Val Pro Gln Cys Gln Cys Ser Ser Met
                965                 970                 975

Glu Glu Lys Glu Lys Asp Gln Cys Ser Leu Glu Ile Ser Asn Cys Lys
            980                 985                 990
```

-continued

Gln Gly Glu Gln Ala Cys Asn Ser Gly Ile Thr Ile Phe Glu Ile Asn
          995                 1000                1005

Pro Ile Ser Asn Asn Ser Lys Ser Pro Leu Ile Gln Glu Ser Glu
    1010                1015                1020

Lys Gly His Phe Ser Asp Ile His Gly Glu Lys Ile Lys Thr Ser
    1025                1030                1035

Glu Thr Lys Asn Ser Ser Ser Pro Arg Val Glu Gln Glu Leu Thr
    1040                1045                1050

Gly His Phe Ser Met Lys Cys Tyr Gln Lys Asp Lys Ser Thr Thr
    1055                1060                1065

Lys Gln Asp Ser Ser Leu Lys Thr Glu Gln Lys Ile Lys Asn Leu
    1070                1075                1080

Ser Ser Lys Cys Asp Lys Pro Asn Pro Leu Lys Ser Ser Lys Ile
    1085                1090                1095

Pro Thr Pro Glu Thr Phe Asn Val Val Thr Ser Asn Ser Asp Lys
    1100                1105                1110

Asn Met Pro Ala Phe Ser Lys Gln Asp Ser Gln Gly Ser Leu Gln
    1115                1120                1125

Lys Lys His Leu Phe Gln Asp Ser Asp Pro Val Lys Gly His Val
    1130                1135                1140

Trp Leu Leu Pro Asn Lys Asp Pro Arg Arg Arg Asn Thr Phe Leu
    1145                1150                1155

Val Gln Ser Val Ser Pro Glu Lys Lys Lys Leu Lys Phe Lys Ser
    1160                1165                1170

Gly Ser Ser Lys Leu Lys Tyr Phe Glu Lys Arg Lys Met Asp His
    1175                1180                1185

Leu Leu Ile Ser Asp Val Glu Ile Lys Lys Lys Tyr Glu Lys
    1190                1195                1200

Gln Glu Gln Asn Lys Asn Ala Gly Gly Thr Leu Lys Leu Cys Ser
    1205                1210                1215

Thr Leu Thr Glu Pro Asn Glu Arg Ala Cys Ala Lys Glu Lys Ile
    1220                1225                1230

Val Thr Asn Ser Glu Pro Ser Asp Ser Lys Gly Ser Ser Ser Lys
    1235                1240                1245

Ser Thr Arg Val Ile Thr Val Gln Glu Tyr Leu Gln Arg Lys Lys
    1250                1255                1260

Asp Lys His Val Ile Gly Asn Asn Ala Ser Lys Asn Ile Cys Val
    1265                1270                1275

Glu Asn Val Pro Cys Asp Ser Glu Pro Met Lys Ser Ser Lys His
    1280                1285                1290

Ser Ala Ser Pro Ser Leu Gly Lys Leu Ile Glu Gly Gln Gly Val
    1295                1300                1305

Ser Ala Glu Thr Leu Lys Glu Val Glu His Asn Ser Thr Ser His
    1310                1315                1320

Gly Lys Asn Leu Lys Thr His Arg Ser Glu Glu Thr Arg Pro Tyr
    1325                1330                1335

Ser Val Ser Asn Ser Lys Glu Lys Phe Tyr Arg Thr His Pro Asp
    1340                1345                1350

Lys Ser Tyr Ile Asp Lys Ala Lys Leu Glu Arg Leu Thr Ser Met
    1355                1360                1365

Ser Ser Lys Ser Ser Gln Leu Gln Val Lys Glu Lys Arg Lys Gln
    1370                1375                1380

Tyr Leu Asn Arg Val Ala Phe Lys Cys Thr Glu Gln Glu Ser Ile

```
            1385                1390                1395

Cys Leu Thr Lys Leu Asp Ser Ala Ser Lys Lys Leu Ser Lys Glu
    1400                1405                1410

Lys Glu Lys Ser Thr Ala Cys Ala Pro Met Thr Lys Asp Tyr Thr
    1415                1420                1425

His Lys Pro Met Leu Glu Phe Lys Leu Cys Pro Asp Val Leu Leu
    1430                1435                1440

Lys Asn Thr Ser Ser Ile Asp Lys Gly Asp Asp Pro Arg Pro Gly
    1445                1450                1455

Pro Glu Lys Glu Arg Ala Pro Val Gln Val Ser Gly Ile Lys Thr
    1460                1465                1470

Thr Lys Glu Asp Trp Leu Lys Cys Ile Pro Thr Arg Thr Lys Met
    1475                1480                1485

Pro Glu Ser Ser Glu Gln Thr Asp Arg Ala Asp Ser Arg Leu Ser
    1490                1495                1500

Lys Arg Ser Phe Ser Ala Asp Glu Phe Glu Thr Leu Gln Asn Pro
    1505                1510                1515

Val Lys Asp Ser Asn Val Met Phe Arg Thr Phe Lys Lys Met Tyr
    1520                1525                1530

Leu Glu Lys Arg Ser Arg Ser Leu Gly Ser Ser Pro Val Lys
    1535                1540                1545
```

<210> SEQ ID NO 22
<211> LENGTH: 1515
<212> TYPE: PRT
<213> ORGANISM: Cricetinae sp.
<220> FEATURE:
<221> NAME/KEY: MOD_RES
<222> LOCATION: (879)..(879)
<223> OTHER INFORMATION: Any amino acid

<400> SEQUENCE: 22

```
Met Asn Trp Asn Ala Lys Pro Glu Asn Ala Ala Pro Asn Pro Tyr
1               5                   10                  15

Ser Lys Ser Gln Ser Ser Leu Leu Gln Gln Phe Leu Met Pro Ser Thr
                20                  25                  30

Thr Ser Gln Ser Ser Phe Ser Cys Leu Pro His Asn Gln Glu Ala Cys
        35                  40                  45

Ile Tyr Pro Thr Asn Ser Asn Ser Val Ser Gln Pro Leu Leu Asn Val
    50                  55                  60

Arg Ser Phe Ile Asn Pro Pro Ile Ser Val Ser Asn Val His Asn Arg
65                  70                  75                  80

Thr Val Val Ala Ser Gln Thr Ser Val Glu Arg Val Thr Tyr Thr Asn
                85                  90                  95

Val Lys Gly Ala Gln Gln Pro Asn His Asn Leu Gln Thr Val Ser Ser
                100                 105                 110

Gly Val Val Gln Asn Ala Trp Met Asn Ser Thr Met Arg Asn Phe Met
            115                 120                 125

Pro Ser Leu Thr Glu Ala Thr Ile Ser His Lys Pro Asp Gly Gly Pro
    130                 135                 140

Ser Met Pro Tyr Met His Ala Pro Gln Ser His Leu Val Thr Ser Asp
145                 150                 155                 160

Thr Tyr Ser Val Gln Leu Gln Met Thr Pro Ser Asn Ser Val Arg Gly
                165                 170                 175

Pro Val Thr Tyr Gln Gly Asn Tyr Gln Gly Asn Pro Gly Leu Asn His
                180                 185                 190
```

```
Ser Met Ala Gly Glu Leu Gly Trp Val Gln Cys Ala Ser Ser Glu Leu
        195                 200                 205
Thr Tyr Pro Asp Tyr Arg Pro Pro Lys Gln Tyr Pro Tyr Leu Pro
210                 215                 220
Gln Ser Phe Val Gln Asp Thr Ser Val Gln Lys Gln Asn Phe Val Ser
225                 230                 235                 240
Ser Thr Ser Leu Gln Val Lys Asn Asn Gln Leu Pro Pro Ser Thr Gln
            245                 250                 255
Thr Leu Pro Ser Lys Arg Pro Val Pro Val Ser Ser Tyr Gln Tyr Ala
                260                 265                 270
Ala Glu Thr Ser Lys Arg Leu Pro Pro Pro Tyr Ser Cys Arg Tyr
            275                 280                 285
Gly Ser Gln His Val Gln Asn Ser Gln Ser Val Ser Arg His Leu Pro
        290                 295                 300
Val Glu Val Pro Gln Ser Ser Glu Met His Ser Ser Glu Lys Lys Lys
305                 310                 315                 320
Asp Ala Tyr Lys Val Phe Gln Gln Gln Trp Gln Ser Thr Ser Lys Asn
                325                 330                 335
Val Ser Thr Ile Gly Lys Phe Cys Glu Leu Lys Ile Asn Thr Lys Gln
            340                 345                 350
Ser Tyr Asn Asp Ser Ala Gly Ser Ser Asp Gly Val His Thr Leu
                355                 360                 365
Val Gln Asn Asn Gln Glu Glu Arg Lys Tyr Ser Tyr Asn Pro Ser Thr
        370                 375                 380
Asn Gln Ile Leu Asp Thr Asn Val Thr Lys Glu Lys Leu Val Arg Asp
385                 390                 395                 400
Ile Lys Ser Leu Val Glu Ile Ser Trp Ala Met Val Ala His Ser Glu
                405                 410                 415
Phe Ser Ala Lys Glu Met Ser Ala Lys Arg Asp Asn Gln Cys Ser Met
                420                 425                 430
Glu Leu Leu Ala Thr Cys Leu Ser Leu Trp Lys Asn Gln Pro Pro Lys
            435                 440                 445
Thr Thr Glu Glu Asn Val Ser Lys Pro Leu Glu Glu Lys Gln Tyr Asn
        450                 455                 460
Ala Ser Arg Thr Ser Thr Thr Ala Val Gly Pro Ser Asn Pro Met Asn
465                 470                 475                 480
Glu Val His Val Lys Asn Phe Cys Ser Gly Val Arg Asn Ser Gln Lys
                485                 490                 495
Ile Thr Thr Ser Ser Gln Thr Val Leu Ser Val Leu Thr Pro Val Tyr
            500                 505                 510
Asp Ser Ser Asp Val Ala Val Gly Lys Gly Thr Glu Leu Gln Ile Ala
                515                 520                 525
Val Val Ser Pro Leu Ile Leu Ser Asp Val Ser Thr Val Pro Gly Lys
        530                 535                 540
Glu Leu Ala Pro Glu Val Val Ser Glu Thr Val Tyr Pro Val Val Lys
545                 550                 555                 560
Glu Gly Ser Val Cys Ser Leu Gln Asn Gln Gln Ala Glu Asn Ala Thr
                565                 570                 575
Val Thr Ala Gly Leu Pro Phe Asp Val Ile Arg Ala Val Ala Ser Ala
            580                 585                 590
Thr Val Ser Ala Glu Leu Ser Leu Pro Gly His Lys Glu Lys Gln His
        595                 600                 605
```

```
Lys Pro Thr Gln Thr Asp Leu Asp Thr Ala Asp Gly Ser Leu Gly Lys
610                 615                 620

His Ser Pro Gln Gly Ala Glu Ala Leu Pro Asn Pro Arg Asp Ser Thr
625                 630                 635                 640

Ile Val Ser Gly Pro Ile Leu Gln Ile Glu Ser Ile Cys Ser Leu Ala
            645                 650                 655

Glu Gly Asp Val Ser Tyr Asn Ser Gln Ile Ala Glu Ile Phe Asn Ser
            660                 665                 670

Val Gln Asn Glu Pro Gln Lys Pro Ser Pro Asp Gln Val Ile Asn
            675                 680                 685

Ser Gln Gln Glu Gln Val Asp Lys Val Ala Glu Asn Lys Asp Leu
690                 695                 700

Ser Phe Leu Lys Asp Lys Cys Met Gln Cys Thr Asp Val Pro His Glu
705                 710                 715                 720

Val Thr Glu Gln Pro Glu Pro Leu Gln Pro Leu Glu Thr Thr Ser Asp
                725                 730                 735

Glu Tyr Val Glu Ala Asn Gly Glu Ile Leu Glu Ser Ser Lys Glu
            740                 745                 750

Asn Pro Gly Glu Lys Glu Met Thr Lys Asp Ile Leu Cys Ser Pro Ala
            755                 760                 765

Ala Val Gln Gln Asp Pro Gln Pro Gln Glu Ile Asp Thr Ala Ser Ser
770                 775                 780

Lys Ser Gly His Ser Phe Ser Thr Val Asn Glu Ile Asn Asp Glu Asn
785                 790                 795                 800

Glu Pro Val Ser Tyr Leu His Asp Gln Leu Leu Glu Leu Leu Lys Glu
                805                 810                 815

Phe Pro Tyr Gly Ile Glu Thr Ile Ala Arg Pro Glu Val Tyr Val Gly
            820                 825                 830

Gln Gln Lys Thr His Glu Ile Leu Glu Asn Gln Thr Gly Ser Lys Thr
            835                 840                 845

Gly Asn Val Ser Gly Asp Asn Thr Asp Gln Ile Lys Ile Thr Val Leu
            850                 855                 860

Asn Ser Glu Gln Ile Lys Glu Leu Phe Pro Glu Glu Asp Gln Xaa Val
865                 870                 875                 880

Asp Lys Leu Ala Glu Pro Glu Asn Thr Lys Ile Ile Ala Glu Val Lys
                885                 890                 895

Ser Leu Cys Asp Ser Gln Val Pro Arg Glu Glu Ser His Asn Pro Gly
            900                 905                 910

Met Leu Asp Leu Glu Lys Asp Lys Ile His Cys Cys Ala Leu Gly Trp
            915                 920                 925

Leu Ser Met Val Tyr Glu Gly Val Pro Gln Cys Gln Cys Ser Ser Met
930                 935                 940

Glu Glu Lys Glu Lys Asp Gln Cys Ser Leu Glu Ile Ser Asn Cys Lys
945                 950                 955                 960

Gln Gly Glu Gln Ala Cys Asn Ser Gly Ile Thr Ile Phe Glu Ile Asn
                965                 970                 975

Pro Ile Ser Asn Asn Ser Lys Ser Pro Leu Ile Gln Glu Ser Glu Lys
            980                 985                 990

Gly His Phe Ser Asp Ile His Gly Glu Lys Ile Lys Thr Ser Glu Thr
            995                 1000                1005

Lys Asn Ser Ser Ser Pro Arg Val Glu Gln Glu Leu Thr Gly His
        1010                1015                1020

Phe Ser Met Lys Cys Tyr Gln Lys Asp Lys Ser Thr Thr Lys Gln
```

-continued

```
              1025                1030                1035

Asp Ser Ser Leu Lys Thr Glu Gln Lys Ile Lys Asn Leu Ser Ser
        1040                1045                1050

Lys Cys Asp Lys Pro Asn Pro Leu Lys Ser Ser Lys Ile Pro Thr
        1055                1060                1065

Pro Glu Thr Phe Asn Val Val Thr Ser Asn Ser Asp Lys Asn Met
        1070                1075                1080

Pro Ala Phe Ser Lys Gln Asp Ser Gln Gly Ser Leu Gln Lys Lys
        1085                1090                1095

His Leu Phe Gln Asp Ser Asp Pro Val Lys Gly His Val Trp Leu
        1100                1105                1110

Leu Pro Asn Lys Asp Pro Arg Arg Arg Asn Thr Phe Leu Val Gln
        1115                1120                1125

Ser Val Ser Pro Glu Lys Lys Lys Leu Lys Phe Lys Ser Gly Ser
        1130                1135                1140

Ser Lys Leu Lys Tyr Phe Glu Lys Arg Lys Met Asp His Leu Leu
        1145                1150                1155

Ile Ser Asp Val Glu Ile Lys Lys Lys Tyr Glu Lys Gln Glu
        1160                1165                1170

Gln Asn Lys Asn Ala Gly Gly Thr Leu Lys Leu Cys Ser Thr Leu
        1175                1180                1185

Thr Glu Pro Asn Glu Arg Ala Cys Ala Lys Glu Lys Ile Val Thr
        1190                1195                1200

Asn Ser Glu Pro Ser Asp Ser Lys Gly Ser Ser Ser Lys Ser Thr
        1205                1210                1215

Arg Val Ile Thr Val Gln Glu Tyr Leu Gln Arg Lys Lys Asp Lys
        1220                1225                1230

His Val Ile Gly Asn Asn Ala Ser Lys Asn Ile Cys Val Glu Asn
        1235                1240                1245

Val Pro Cys Asp Ser Glu Pro Met Lys Ser Ser Lys His Ser Ala
        1250                1255                1260

Ser Pro Ser Leu Gly Lys Leu Ile Glu Gly Gln Gly Val Ser Ala
        1265                1270                1275

Glu Thr Leu Lys Glu Val Glu His Asn Ser Ser Ser His Gly Lys
        1280                1285                1290

Asn Leu Lys Thr His Arg Ser Glu Glu Thr Arg Pro Tyr Ser Val
        1295                1300                1305

Ser Asn Ser Lys Glu Lys Phe Tyr Arg Thr His Pro Asp Lys Ser
        1310                1315                1320

Tyr Ile Asp Lys Ala Lys Leu Glu Arg Leu Thr Ser Met Ser Ser
        1325                1330                1335

Lys Ser Ser Gln Leu Gln Val Lys Glu Lys Arg Lys Gln Tyr Leu
        1340                1345                1350

Asn Arg Val Ala Phe Lys Cys Thr Glu Gln Glu Ser Ile Cys Leu
        1355                1360                1365

Thr Lys Leu Asp Ser Ala Ser Lys Lys Leu Ser Lys Glu Lys Glu
        1370                1375                1380

Lys Ser Thr Ala Cys Ala Pro Met Thr Lys Asp Tyr Thr His Lys
        1385                1390                1395

Pro Met Leu Glu Phe Lys Leu Cys Pro Asp Val Leu Leu Lys Asn
        1400                1405                1410

Thr Ser Ser Ile Asp Lys Gly Asp Asp Pro Arg Pro Gly Pro Glu
        1415                1420                1425
```

-continued

Lys Glu Arg Ala Pro Val Gln Val Ser Gly Ile Lys Thr Thr Lys
1430                1435                1440

Glu Asp Trp Leu Lys Cys Ile Pro Thr Arg Thr Lys Met Pro Glu
1445                1450                1455

Ser Ser Glu Gln Thr Asp Arg Ala Asp Ser Arg Leu Ser Lys Arg
1460                1465                1470

Ser Phe Ser Ala Asp Glu Phe Glu Thr Leu Gln Asn Pro Val Lys
1475                1480                1485

Asp Ser Asn Val Met Phe Arg Thr Phe Lys Lys Met Tyr Leu Glu
1490                1495                1500

Lys Arg Ser Arg Ser Leu Gly Ser Ser Pro Val Lys
1505                1510                1515

<210> SEQ ID NO 23
<211> LENGTH: 1747
<212> TYPE: PRT
<213> ORGANISM: Homo sapiens

<400> SEQUENCE: 23

Met Asn Trp Asn Glu Lys Pro Lys Ser Ala Thr Leu Pro Pro Leu Tyr
1               5                   10                  15

Pro Lys Ser Gln Pro Pro Phe Leu His Gln Ser Leu Ile Asn Gln Ile
                20                  25                  30

Thr Thr Thr Ser Gln Ser Ser Phe Ser Tyr Pro Gly Ser Asn Gln Glu
            35                  40                  45

Ala Cys Met Tyr Pro Gly Asn Ser Asn Pro Ile Ser Gln Pro Leu Leu
        50                  55                  60

Asn Ile Gln Asn Tyr Pro Gln Gln Ile Ser Val Ser Asp Met His Asn
65                  70                  75                  80

Gly Thr Val Val Ala Ser His Thr Ser Val Glu Arg Ile Thr Tyr Ala
                85                  90                  95

Asn Val Asn Gly Pro Lys Gln Leu Thr His Asn Leu Gln Met Ser Ser
            100                 105                 110

Gly Val Thr Gln Asn Val Trp Leu Asn Ser Pro Met Arg Asn Pro Val
        115                 120                 125

His Ser His Ile Gly Ala Thr Val Ser His Gln Thr Asp Phe Gly Ala
130                 135                 140

Asn Val Pro Asn Met Pro Ala Leu Gln Ser Gln Leu Ile Thr Ser Asp
145                 150                 155                 160

Thr Tyr Ser Met Gln Met Gln Met Ile Pro Ser Asn Ser Thr Arg Leu
                165                 170                 175

Pro Val Ala Tyr Gln Gly Asn Gln Gly Leu Asn Gln Ser Phe Ser Glu
            180                 185                 190

Gln Gln Val Asp Trp Thr Gln Gln Cys Ile Ser Lys Gly Leu Thr Tyr
        195                 200                 205

Pro Asp Tyr Arg Pro Pro Lys Leu Tyr Arg Tyr Ser Pro Gln Ser
        210                 215                 220

Phe Leu Pro Asp Ser Thr Ile Gln Lys Gln Asn Phe Ile Pro His Thr
225                 230                 235                 240

Ser Leu Gln Val Lys Asn Ser Gln Leu Leu Asn Ser Val Leu Thr Leu
                245                 250                 255

Pro Ser Arg Gln Thr Ser Ala Val Pro Ser Gln Gln Tyr Ala Thr Gln
            260                 265                 270

Thr Asp Lys Arg Pro Pro Pro Pro Tyr Asn Cys Arg Tyr Gly Ser

```
            275                 280                 285
Gln Pro Leu Gln Ser Thr Gln His Ile Thr Lys His Leu Ser Met Glu
290                 295                 300

Val Pro Gln Ser Arg Glu Met Leu Ser Ser Glu Ile Arg Thr Ser Phe
305                 310                 315                 320

Gln Gln Gln Trp Gln Asn Pro Asn Glu Asn Val Ser Thr Ile Gly Asn
                325                 330                 335

Phe Thr Asn Leu Lys Val Asn Thr Asn Ser Lys Gln Pro Phe Asn Ser
            340                 345                 350

Pro Ile Arg Ser Ser Val Asp Gly Val Gln Thr Leu Ala Gln Thr Asn
        355                 360                 365

Glu Glu Lys Ile Met Asp Ser Cys Asn Pro Thr Ser Asn Gln Val Leu
    370                 375                 380

Asp Thr Ser Val Ala Lys Glu Lys Leu Val Arg Asp Ile Lys Thr Leu
385                 390                 395                 400

Val Glu Ile Lys Gln Lys Phe Ser Glu Leu Ala Arg Lys Ile Lys Ile
                405                 410                 415

Asn Lys Asp Leu Leu Met Ala Ala Gly Cys Ile Lys Met Thr Asn Thr
            420                 425                 430

Ser Tyr Ser Glu Pro Ala Gln Asn Ser Lys Leu Ser Leu Lys Gln Thr
        435                 440                 445

Ala Lys Ile Gln Ser Gly Pro Gln Ile Thr Pro Val Met Pro Glu Asn
    450                 455                 460

Ala Glu Arg Gln Thr Pro Thr Val Val Glu Ser Ala Glu Thr Asn Lys
465                 470                 475                 480

Thr Gln Cys Met Leu Asn Ser Asp Ile Gln Glu Val Asn Cys Arg Arg
                485                 490                 495

Phe Asn Gln Val Asp Ser Val Leu Pro Asn Pro Val Tyr Ser Glu Lys
            500                 505                 510

Arg Pro Met Pro Asp Ser Ser His Asp Val Lys Val Leu Thr Ser Lys
        515                 520                 525

Thr Ser Ala Val Glu Met Thr Gln Ala Val Leu Asn Thr Gln Leu Ser
    530                 535                 540

Ser Glu Asn Val Thr Lys Val Glu Gln Asn Ser Pro Ala Val Cys Glu
545                 550                 555                 560

Thr Ile Ser Val Pro Lys Ser Met Ser Thr Glu Glu Tyr Lys Ser Lys
                565                 570                 575

Ile Gln Asn Glu Asn Met Leu Leu Leu Ala Leu Leu Ser Gln Ala Arg
            580                 585                 590

Lys Thr Gln Lys Thr Val Leu Lys Asp Ala Asn Gln Thr Ile Gln Asp
        595                 600                 605

Ser Lys Pro Asp Ser Cys Glu Met Asn Pro Asn Thr Gln Met Thr Gly
    610                 615                 620

Asn Gln Leu Asn Leu Lys Asn Met Glu Thr Pro Ser Thr Ser Asn Val
625                 630                 635                 640

Ser Gly Arg Val Leu Asp Asn Ser Phe Cys Ser Gly Gln Glu Ser Ser
                645                 650                 655

Thr Lys Gly Met Pro Ala Lys Ser Asp Ser Ser Cys Ser Met Glu Val
            660                 665                 670

Leu Ala Thr Cys Leu Ser Leu Trp Lys Lys Gln Pro Ser Asp Thr Ala
        675                 680                 685

Lys Glu Lys Glu Cys Asp Lys Leu Arg Thr Asn Thr Thr Ala Val Gly
    690                 695                 700
```

```
Ile Ser Lys Pro Ala Asn Ile His Val Lys Ser Pro Cys Ser Val Val
705                 710                 715                 720

Gly Asn Ser Asn Ser Gln Asn Lys Ile Ser Asn Pro Ser Gln Gln Thr
            725                 730                 735

Ala Leu Ser Met Val Met His Asn Tyr Glu Ser Ser Gly Ile Asn Ile
        740                 745                 750

Thr Lys Gly Thr Glu Leu Gln Ile Ala Val Val Ser Pro Leu Val Leu
            755                 760                 765

Ser Glu Val Lys Thr Leu Ser Val Lys Gly Ile Thr Pro Ala Val Leu
770                 775                 780

Pro Glu Thr Val Tyr Pro Val Ile Lys Glu Gly Ser Val Cys Ser Leu
785                 790                 795                 800

Gln Asn Gln Leu Ala Glu Asn Ala Lys Ala Thr Ala Ala Leu Lys Val
            805                 810                 815

Asp Val Ser Gly Pro Val Ala Ser Thr Ala Thr Ser Thr Lys Ile Phe
            820                 825                 830

Pro Leu Thr Gln Lys Glu Lys Gln Asn Glu Ser Thr Asn Gly Asn Ser
            835                 840                 845

Glu Val Thr Pro Asn Val Asn Gln Gly Lys His Asn Lys Leu Glu Ser
850                 855                 860

Ala Ile His Ser Pro Met Asn Asp Gln Gln Ile Ser Gln Glu Ser Arg
865                 870                 875                 880

Asn Ser Thr Val Val Ser Ser Asp Thr Leu Gln Ile Asp Asn Ile Cys
            885                 890                 895

Ser Leu Val Glu Gly Asp Thr Ser Tyr Asn Ser Gln Ile Ala Lys Ile
            900                 905                 910

Phe Ser Ser Leu Pro Leu Lys Met Val Glu Pro Gln Lys Pro Ser Leu
            915                 920                 925

Pro Asn Gln Gln Gly Ile Gly Ser Arg Glu Pro Glu Lys Gln Leu Asp
    930                 935                 940

Asn Thr Thr Glu Asn Lys Asp Phe Gly Phe Gln Lys Asp Lys Pro Val
945                 950                 955                 960

Gln Cys Thr Asp Val Ser His Lys Ile Cys Asp Gln Ser Lys Ser Glu
            965                 970                 975

Pro Pro Leu Glu Ser Ser Phe Asn Asn Leu Glu Thr Asn Arg Val Ile
            980                 985                 990

Leu Glu Lys Ser Ser Leu Glu His Ala Thr Glu Lys Ser Thr Ala Asn
            995                1000                1005

Asp Thr Cys Ser Ser Ala Ala Ile Gln Glu Asp Ile Tyr Pro Gln
        1010                1015                1020

Glu Ile Asp Ala Ser Ser Asn Tyr Thr Pro Gln Asp Pro Ala Arg
        1025                1030                1035

Asn Glu Ile His Ser Asp Lys Ala Pro Val Leu Tyr Leu His Asp
        1040                1045                1050

Gln Leu Ser Glu Leu Leu Lys Glu Phe Pro Tyr Gly Ile Glu Ala
        1055                1060                1065

Val Asn Thr Arg Glu Gly Ser Val Gly Gln Gln Thr Thr Tyr Gln
        1070                1075                1080

Thr Ser Glu Asp Gln Thr Ala Asp Lys Thr Ser Ser Asp Ser Lys
        1085                1090                1095

Asp Pro Ala Asp Gln Ile Gln Ile Thr Ile Leu Ser Ser Glu Gln
        1100                1105                1110
```

Met Lys Glu Ile Phe Pro Glu Gln Asp Asp Gln Pro Tyr Val Val
1115                1120                1125

Asp Lys Leu Ala Glu Pro Gln Lys Glu Pro Ile Thr Glu Val
1130                1135                1140

Val Ser Gln Cys Asp Leu Gln Ala Pro Ala Ala Gly Gln Ser Arg
1145                1150                1155

Asp Ser Val Ile Leu Asp Ser Glu Lys Asp Asp Ile His Cys Cys
1160                1165                1170

Ala Leu Gly Trp Leu Ser Met Val Tyr Glu Gly Val Pro Gln Cys
1175                1180                1185

Gln Cys Asn Ser Ile Lys Asn Ser Ser Ser Glu Glu Glu Lys Gln
1190                1195                1200

Lys Glu Gln Cys Ser Pro Leu Asp Thr Asn Ser Cys Lys Gln Gly
1205                1210                1215

Glu Arg Thr Ser Asp Arg Asp Val Thr Val Val Gln Phe Lys Ser
1220                1225                1230

Leu Val Asn Asn Pro Lys Thr Pro Pro Asp Gly Lys Ser His Phe
1235                1240                1245

Pro Glu Leu Gln Asp Asp Ser Arg Lys Asp Thr Pro Lys Thr Lys
1250                1255                1260

His Lys Ser Leu Pro Arg Thr Glu Gln Glu Leu Val Ala Gly Gln
1265                1270                1275

Phe Ser Ser Lys Cys Asp Lys Leu Asn Pro Leu Gln Asn His Lys
1280                1285                1290

Arg Lys Lys Leu Arg Phe His Glu Val Thr Phe His Ser Ser Asn
1295                1300                1305

Lys Met Thr Ala Ser Tyr Glu Gln Ala Ser Gln Glu Thr Arg Gln
1310                1315                1320

Lys Lys His Val Thr Gln Asn Ser Arg Pro Leu Lys Thr Lys Thr
1325                1330                1335

Ala Phe Leu Pro Asn Lys Asp Val Tyr Lys Lys His Ser Ser Leu
1340                1345                1350

Gly Gln Ser Leu Ser Pro Glu Lys Ile Lys Leu Lys Leu Lys Ser
1355                1360                1365

Val Ser Phe Lys Gln Lys Arg Lys Leu Asp Gln Gly Asn Val Leu
1370                1375                1380

Asp Met Glu Val Lys Lys Lys His Asp Lys Gln Glu Gln Lys
1385                1390                1395

Gly Ser Val Gly Ala Thr Phe Lys Leu Gly Asp Ser Leu Ser Asn
1400                1405                1410

Pro Asn Glu Arg Ala Ile Val Lys Glu Lys Met Val Ser Asn Thr
1415                1420                1425

Lys Ser Val Asp Thr Lys Ala Ser Ser Ser Lys Phe Ser Arg Ile
1430                1435                1440

Leu Thr Pro Lys Glu Tyr Leu Gln Arg Gln Lys His Lys Glu Ala
1445                1450                1455

Leu Ser Asn Lys Ala Ser Lys Ile Cys Val Lys Asn Val Pro
1460                1465                1470

Cys Asp Ser Glu His Met Arg Pro Ser Lys Leu Ala Val Gln Val
1475                1480                1485

Glu Ser Cys Gly Lys Ser Asn Glu Lys His Ser Ser Gly Val Gln
1490                1495                1500

Thr Ser Lys Glu Ser Leu Asn Gly Leu Thr Ser His Gly Lys Asn

```
                    1505                1510                1515

Leu Lys Ile His His Ser Gln Glu Ser Lys Thr Tyr Asn Ile Leu
    1520                1525                1530

Arg Asn Val Lys Glu Lys Val Gly Gly Lys Gln Pro Asp Lys Ile
    1535                1540                1545

Trp Ile Asp Lys Thr Lys Leu Asp Lys Leu Thr Asn Ile Ser Asn
    1550                1555                1560

Glu Ala Gln Phe Ser Gln Met Pro Pro Gln Val Lys Asp Gln Lys
    1565                1570                1575

Lys Leu Tyr Leu Asn Arg Val Gly Phe Lys Cys Thr Glu Arg Glu
    1580                1585                1590

Ser Ile Ser Leu Thr Lys Leu Glu Ser Ser Pro Arg Lys Leu His
    1595                1600                1605

Lys Asp Lys Arg Gln Glu Asn Lys His Lys Thr Phe Leu Pro Val
    1610                1615                1620

Lys Gly Asn Thr Glu Lys Ser Asn Met Leu Glu Phe Lys Leu Cys
    1625                1630                1635

Pro Asp Ile Leu Leu Lys Asn Thr Asn Ser Val Glu Glu Arg Lys
    1640                1645                1650

Asp Val Lys Pro His Pro Arg Lys Glu Gln Ala Pro Leu Gln Val
    1655                1660                1665

Ser Gly Ile Lys Ser Thr Lys Glu Asp Trp Leu Lys Phe Val Ala
    1670                1675                1680

Thr Lys Lys Arg Thr Gln Lys Asp Ser Gln Glu Arg Asp Asn Val
    1685                1690                1695

Asn Ser Arg Leu Ser Lys Arg Ser Phe Ser Ala Asp Gly Phe Glu
    1700                1705                1710

Met Leu Gln Asn Pro Val Lys Asp Ser Lys Glu Met Phe Gln Thr
    1715                1720                1725

Tyr Lys Gln Met Tyr Leu Glu Lys Arg Ser Arg Ser Leu Gly Ser
    1730                1735                1740

Ser Pro Val Lys
    1745

<210> SEQ ID NO 24
<211> LENGTH: 1747
<212> TYPE: PRT
<213> ORGANISM: Homo sapiens

<400> SEQUENCE: 24

Met Asn Trp Asn Glu Lys Pro Lys Ser Ala Thr Leu Pro Pro Leu Tyr
1               5                   10                  15

Pro Lys Ser Gln Pro Pro Phe Leu His Gln Ser Leu Ile Asn Gln Ile
                20                  25                  30

Thr Thr Thr Ser Gln Ser Ser Phe Ser Tyr Pro Gly Ser Asn Gln Glu
            35                  40                  45

Ala Cys Met Tyr Pro Gly Asn Ser Asn Pro Ile Ser Gln Pro Leu Leu
        50                  55                  60

Asn Ile Gln Asn Tyr Pro Gln Gln Ile Ser Val Ser Asp Met His Asn
65                  70                  75                  80

Gly Thr Val Val Ala Ser His Thr Ser Val Glu Arg Ile Thr Tyr Ala
                85                  90                  95

Asn Val Asn Gly Pro Lys Gln Leu Thr His Asn Leu Gln Met Ser Ser
                100                 105                 110
```

-continued

```
Gly Val Thr Gln Asn Val Trp Leu Asn Ser Pro Met Arg Asn Pro Val
            115                 120                 125

His Ser His Ile Gly Ala Thr Val Ser His Gln Thr Asp Phe Gly Ala
            130                 135                 140

Asn Val Pro Asn Met Pro Ala Leu Gln Ser Gln Leu Ile Thr Ser Asp
145                 150                 155                 160

Thr Tyr Ser Met Gln Met Gln Met Ile Pro Ser Asn Ser Thr Arg Leu
                165                 170                 175

Pro Val Ala Tyr Gln Gly Asn Gln Gly Leu Asn Gln Ser Phe Ser Glu
            180                 185                 190

Gln Gln Val Asp Trp Thr Gln Gln Cys Ile Ser Lys Gly Leu Thr Tyr
            195                 200                 205

Pro Asp Tyr Arg Pro Pro Lys Leu Tyr Arg Tyr Ser Pro Gln Ser
210                 215                 220

Phe Leu Pro Asp Ser Thr Ile Gln Lys Gln Asn Phe Ile Pro His Thr
225                 230                 235                 240

Ser Leu Gln Val Lys Asn Ser Gln Leu Leu Asn Ser Val Leu Thr Leu
                245                 250                 255

Pro Ser Arg Gln Thr Ser Ala Val Pro Ser Gln Gln Tyr Ala Thr Gln
            260                 265                 270

Thr Asp Lys Arg Pro Pro Pro Tyr Asn Cys Arg Tyr Gly Ser
            275                 280                 285

Gln Pro Leu Gln Ser Thr Gln His Ile Thr Lys His Leu Ser Met Glu
            290                 295                 300

Val Pro Gln Ser Arg Glu Met Leu Ser Ser Glu Ile Arg Thr Ser Phe
305                 310                 315                 320

Gln Gln Gln Trp Gln Asn Pro Asn Glu Asn Val Ser Thr Ile Gly Asn
                325                 330                 335

Phe Thr Asn Leu Lys Val Asn Thr Asn Ser Lys Gln Pro Phe Asn Ser
                340                 345                 350

Pro Ile Arg Ser Ser Val Asp Gly Val Gln Thr Leu Ala Gln Thr Asn
            355                 360                 365

Glu Glu Lys Ile Met Asp Ser Cys Asn Pro Thr Ser Asn Gln Val Leu
            370                 375                 380

Asp Thr Ser Val Ala Lys Glu Lys Leu Val Arg Asp Ile Lys Thr Leu
385                 390                 395                 400

Val Glu Ile Lys Gln Lys Phe Ser Glu Leu Ala Arg Lys Ile Lys Ile
                405                 410                 415

Asn Lys Asp Leu Leu Met Ala Ala Gly Cys Ile Lys Met Thr Asn Thr
            420                 425                 430

Ser Tyr Ser Glu Pro Ala Gln Asn Ser Lys Leu Ser Leu Lys Gln Thr
            435                 440                 445

Ala Lys Ile Gln Ser Gly Pro Gln Ile Thr Pro Val Met Pro Glu Asn
            450                 455                 460

Ala Glu Arg Gln Thr Pro Thr Val Val Glu Ser Ala Glu Thr Asn Lys
465                 470                 475                 480

Thr Gln Cys Met Leu Asn Ser Asp Ile Gln Glu Val Asn Cys Arg Arg
                485                 490                 495

Phe Asn Gln Val Asp Ser Val Leu Pro Asn Pro Val Tyr Ser Glu Lys
            500                 505                 510

Arg Pro Met Pro Asp Pro Ser His Asp Val Lys Val Leu Thr Ser Lys
            515                 520                 525

Thr Ser Ala Val Glu Met Thr Gln Ala Val Leu Asn Thr Gln Leu Ser
```

```
                530                  535                 540
Ser Glu Asn Val Thr Lys Val Glu Gln Asn Ser Pro Ala Val Cys Glu
545                 550                 555                 560

Thr Ile Ser Val Pro Lys Ser Met Ser Thr Glu Glu Tyr Lys Ser Lys
                565                 570                 575

Ile Gln Asn Glu Asn Met Leu Leu Leu Ala Leu Leu Ser Gln Ala Arg
                580                 585                 590

Lys Thr Gln Lys Thr Val Leu Lys Asp Ala Asn Gln Thr Ile Gln Asp
                595                 600                 605

Ser Lys Pro Asp Ser Cys Glu Met Asn Pro Asn Thr Gln Met Thr Gly
610                 615                 620

Asn Gln Leu Asn Leu Lys Asn Met Glu Thr Pro Ser Thr Ser Asn Val
625                 630                 635                 640

Ser Gly Arg Val Leu Asp Asn Ser Phe Cys Ser Gly Gln Glu Ser Ser
                645                 650                 655

Thr Lys Gly Met Pro Ala Lys Ser Asp Ser Ser Cys Ser Met Glu Val
                660                 665                 670

Leu Ala Thr Cys Leu Ser Leu Trp Lys Lys Gln Pro Ser Asp Thr Ala
                675                 680                 685

Lys Glu Lys Glu Cys Asp Lys Leu Arg Thr Asn Thr Thr Ala Val Gly
690                 695                 700

Ile Ser Lys Pro Ala Asn Ile His Val Lys Ser Pro Cys Ser Val Val
705                 710                 715                 720

Gly Asn Ser Asn Ser Gln Asn Lys Ile Ser Asn Pro Ser Gln Gln Thr
                725                 730                 735

Ala Leu Ser Met Val Met His Asn Tyr Glu Ser Ser Gly Ile Asn Ile
                740                 745                 750

Thr Lys Gly Thr Glu Leu Gln Ile Ala Val Val Ser Pro Leu Val Leu
                755                 760                 765

Ser Glu Val Lys Thr Leu Ser Val Lys Gly Ile Thr Pro Ala Val Leu
                770                 775                 780

Pro Glu Thr Val Tyr Pro Val Ile Lys Glu Gly Ser Val Cys Ser Leu
785                 790                 795                 800

Gln Asn Gln Leu Ala Glu Asn Ala Lys Ala Thr Ala Ala Leu Lys Val
                805                 810                 815

Asp Val Ser Gly Pro Val Ala Ser Thr Ala Thr Ser Thr Lys Ile Phe
                820                 825                 830

Pro Leu Thr Gln Lys Glu Lys Gln Asn Glu Ser Thr Asn Gly Asn Ser
                835                 840                 845

Glu Val Thr Pro Asn Val Asn Gln Gly Lys His Asn Lys Leu Glu Ser
                850                 855                 860

Ala Ile His Ser Pro Met Asn Asp Gln Gln Ile Ser Gln Glu Ser Arg
865                 870                 875                 880

Asn Ser Thr Val Val Ser Ser Asp Thr Leu Gln Ile Asp Asn Ile Cys
                885                 890                 895

Ser Leu Val Glu Gly Asp Thr Ser Tyr Asn Ser Gln Ile Ala Lys Ile
                900                 905                 910

Phe Ser Ser Leu Pro Leu Lys Met Val Glu Pro Gln Lys Pro Ser Leu
                915                 920                 925

Pro Asn Gln Gln Gly Ile Gly Ser Arg Glu Pro Glu Lys Gln Leu Asp
                930                 935                 940

Asn Thr Thr Glu Asn Lys Asp Phe Gly Phe Gln Lys Asp Lys Pro Val
945                 950                 955                 960
```

-continued

```
Gln Cys Thr Asp Val Ser His Lys Ile Cys Asp Gln Ser Lys Ser Glu
            965                 970                 975
Pro Pro Leu Glu Ser Ser Phe Asn Asn Leu Glu Thr Asn Arg Val Ile
            980                 985                 990
Leu Glu Lys Ser Ser Leu Glu His Ala Thr Glu Lys Ser Thr Ala Asn
            995                 1000                1005
Asp Thr Cys Ser Ser Ala Ala Ile Gln Glu Asp Ile Tyr Pro Gln
        1010                1015                1020
Glu Ile Asp Ala Ser Ser Asn Tyr Thr Pro Gln Asp Pro Ala Arg
        1025                1030                1035
Asn Glu Ile His Ser Asp Lys Ala Pro Val Leu Tyr Leu His Asp
        1040                1045                1050
Gln Leu Ser Glu Leu Leu Lys Glu Phe Pro Tyr Gly Ile Glu Ala
        1055                1060                1065
Val Asn Thr Arg Glu Gly Ser Val Gly Gln Gln Thr Thr Tyr Gln
        1070                1075                1080
Thr Ser Glu Asp Gln Thr Ala Asp Lys Thr Ser Ser Asp Ser Lys
        1085                1090                1095
Asp Pro Ala Asp Gln Ile Gln Ile Thr Ile Leu Ser Ser Glu Gln
        1100                1105                1110
Met Lys Glu Ile Phe Pro Glu Gln Asp Asp Gln Pro Tyr Val Val
        1115                1120                1125
Asp Lys Leu Ala Glu Pro Gln Lys Glu Pro Ile Thr Glu Val
        1130                1135                1140
Val Ser Gln Cys Asp Leu Gln Ala Pro Ala Ala Gly Gln Ser Arg
        1145                1150                1155
Asp Ser Val Ile Leu Asp Ser Glu Lys Asp Ile His Cys Cys
        1160                1165                1170
Ala Leu Gly Trp Leu Ser Met Val Tyr Glu Gly Val Pro Gln Cys
        1175                1180                1185
Gln Cys Asn Ser Ile Lys Asn Ser Ser Ser Glu Glu Glu Lys Gln
        1190                1195                1200
Lys Glu Gln Cys Ser Pro Leu Asp Thr Asn Ser Cys Lys Gln Gly
        1205                1210                1215
Glu Arg Thr Ser Asp Arg Asp Val Thr Val Val Gln Phe Lys Ser
        1220                1225                1230
Leu Val Asn Asn Pro Lys Thr Pro Pro Asp Gly Lys Ser His Phe
        1235                1240                1245
Pro Glu Leu Gln Asp Asp Ser Arg Lys Asp Thr Pro Lys Thr Lys
        1250                1255                1260
His Lys Ser Leu Pro Arg Thr Glu Gln Glu Leu Val Ala Gly Gln
        1265                1270                1275
Phe Ser Ser Lys Cys Asp Lys Leu Asn Pro Leu Gln Asn His Lys
        1280                1285                1290
Arg Lys Lys Leu Arg Phe His Glu Val Thr Phe His Ser Ser Asn
        1295                1300                1305
Lys Met Thr Ala Ser Tyr Glu Gln Ala Ser Gln Glu Thr Arg Gln
        1310                1315                1320
Lys Lys His Val Thr Gln Asn Ser Arg Pro Leu Lys Thr Lys Thr
        1325                1330                1335
Ala Phe Leu Pro Asn Lys Asp Val Tyr Lys Lys His Ser Ser Leu
        1340                1345                1350
```

```
Gly Gln Ser Leu Ser Pro Glu Lys Ile Lys Leu Lys Leu Lys Ser
    1355                1360                1365

Val Ser Phe Lys Gln Lys Arg Lys Leu Asp Gln Gly Asn Val Leu
    1370                1375                1380

Asp Met Glu Val Lys Lys Lys His Asp Lys Gln Glu Gln Lys
    1385                1390                1395

Gly Ser Val Gly Ala Thr Phe Lys Leu Gly Asp Ser Leu Ser Asn
    1400                1405                1410

Pro Asn Glu Arg Ala Ile Val Lys Glu Lys Met Val Ser Asn Thr
    1415                1420                1425

Lys Ser Val Asp Thr Lys Ala Ser Ser Ser Lys Phe Ser Arg Ile
    1430                1435                1440

Leu Thr Pro Lys Glu Tyr Leu Gln Arg Gln Lys His Lys Glu Ala
    1445                1450                1455

Leu Ser Asn Lys Ala Ser Lys Lys Ile Cys Val Lys Asn Val Pro
    1460                1465                1470

Cys Asp Ser Glu His Met Arg Pro Ser Lys Leu Ala Val Gln Val
    1475                1480                1485

Glu Ser Cys Gly Lys Ser Asn Glu Lys His Ser Ser Gly Val Gln
    1490                1495                1500

Thr Ser Lys Glu Ser Leu Asn Gly Leu Thr Ser His Gly Lys Asn
    1505                1510                1515

Leu Lys Ile His His Ser Gln Glu Ser Lys Thr Tyr Asn Ile Leu
    1520                1525                1530

Arg Asn Val Lys Glu Lys Val Gly Gly Lys Gln Pro Asp Lys Ile
    1535                1540                1545

Trp Ile Asp Lys Thr Lys Leu Asp Lys Leu Thr Asn Ile Ser Asn
    1550                1555                1560

Glu Ala Gln Phe Ser Gln Met Pro Pro Gln Val Lys Asp Gln Lys
    1565                1570                1575

Lys Leu Tyr Leu Asn Arg Val Gly Phe Lys Cys Thr Glu Arg Glu
    1580                1585                1590

Ser Ile Ser Leu Thr Lys Leu Glu Ser Ser Pro Arg Lys Leu His
    1595                1600                1605

Lys Asp Lys Arg Gln Glu Asn Lys His Lys Thr Phe Leu Pro Val
    1610                1615                1620

Lys Gly Asn Thr Glu Lys Ser Asn Met Leu Glu Phe Lys Leu Cys
    1625                1630                1635

Pro Asp Ile Leu Leu Lys Asn Thr Asn Ser Val Glu Glu Arg Lys
    1640                1645                1650

Asp Val Lys Pro His Pro Arg Lys Glu Gln Ala Pro Leu Gln Val
    1655                1660                1665

Ser Gly Ile Lys Ser Thr Lys Glu Asp Trp Leu Lys Phe Val Ala
    1670                1675                1680

Thr Lys Lys Arg Thr Gln Lys Asp Ser Gln Glu Arg Asp Asn Val
    1685                1690                1695

Asn Ser Arg Leu Ser Lys Arg Ser Phe Ser Ala Asp Gly Phe Glu
    1700                1705                1710

Met Leu Gln Asn Pro Val Lys Asp Ser Lys Glu Met Phe Gln Thr
    1715                1720                1725

Tyr Lys Gln Met Tyr Leu Glu Lys Arg Ser Arg Ser Leu Gly Ser
    1730                1735                1740

Ser Pro Val Lys
```

1745

<210> SEQ ID NO 25
<211> LENGTH: 4644
<212> TYPE: DNA
<213> ORGANISM: Cricetulus griseus

<400> SEQUENCE: 25

| | | | | | |
|---|---|---|---|---|---|
| atgaattgga | atgcaaaacc | agagaatgct | gccccaaacc | caccatattc | taaaagccag | 60 |
| tcgtctcttt | tgcagcagtt | tttaatgcct | tccacaactt | ctcaaagttc | tttcagctgt | 120 |
| ctcccacata | accaagaagc | atgcatatat | cccactaatt | caattcagt | ttcacagcca | 180 |
| cttctgaacg | tcaggagttt | cataaatcct | ccgatctctg | tttctaatgt | gcataatagg | 240 |
| acagttgtgg | cctcacagac | ctcagtagaa | agagtcacat | atacaaatgt | taaaggagcc | 300 |
| caacaaccaa | accacaattt | gcaaacagtg | tcttctggag | ttgtgcaaaa | tgcctggatg | 360 |
| aattcaacaa | tgaggaattt | tatgccttct | cttacagagg | caaccatatc | tcataaacct | 420 |
| gatggtgggc | ctagtatgcc | atatatgcat | gcaccacaga | gtcatcttgt | cacatcagac | 480 |
| acctactctg | tgcaactaca | gatgactcct | tcaaactctg | taagaggccc | tgtaacttac | 540 |
| caaggaaatt | atcaaggaaa | tccgggactt | aaccactcga | tggcaggtga | gcttggctgg | 600 |
| gtacaatgtg | catccagtga | acttacttat | ccagattaca | gaccacctcc | aaagcaatat | 660 |
| ccttatttac | cacaaagctt | tgtgcaagac | acttctgttc | agaaacaaaa | ctttgtgtca | 720 |
| tctacatcat | tacaagttaa | aaataatcag | cttccacctt | ctacacagac | cttaccatca | 780 |
| aagcgccctg | tacctgtgtc | gtcatatcag | tatgctgcag | aaaccagcaa | aagactccct | 840 |
| cccccccctt | acagctgtag | atatggaagc | caacatgtgc | aaaattctca | gtctgtttct | 900 |
| agacacttgc | ctgtggaagt | tcctcagagt | tcagaaatgc | actcgtctga | aaaaaagaaa | 960 |
| gatgcttaca | agtctttca | acagcagtgg | cagagcacta | gtaaaaatgt | cagtacaata | 1020 |
| ggaaaattct | gtgagttgaa | aattaataca | aacagtctt | acaatgactc | tgctggctct | 1080 |
| tctggggatg | gtgttcatac | tcttgttcaa | ataatcaag | aagaaagaaa | gtattcttat | 1140 |
| aatccaagta | caaatcaaat | actagacaca | atgtcacaa | agaaaagct | ggtgagggat | 1200 |
| attaaatcac | tagtagaaat | taaaagaaa | ttttcagaac | ttgcaagaaa | aattaaaatc | 1260 |
| aacaaaaagc | ttttgatggc | agctggttgc | agtaaaacag | ctaatacttc | ttatactgaa | 1320 |
| ccaactcggc | attctgaatt | tcagcaaaa | gaaatgtctg | ctaaaaggga | caatcagtgc | 1380 |
| tccatggaat | gctagcaac | atgccttct | ctttggaaaa | accaacctcc | aaaaaccaca | 1440 |
| gaagaaaatg | tttcaaaacc | tttagaagaa | aaacaatata | atgcatcaag | aactagtaca | 1500 |
| acagcggttg | gcccttcaaa | tcccatgaat | gaagttcatg | tgaagaattt | ttgttcaggt | 1560 |
| gttagaaatt | ctcagaaaat | aaccacctcg | tcacaaacag | tcttgtcagt | tctcacacca | 1620 |
| gtttacgatt | cttcagatgt | agctgttgga | aaggaacag | agcttcagat | tgctgtggtt | 1680 |
| tcacctttaa | ttctttcaga | tgtcagtact | gtacctggga | aagagttagc | tcctgaagtc | 1740 |
| gtatctgaaa | ctgtatatcc | agttgtgaag | gaaggcagtg | tttgtagctt | acaaaaccag | 1800 |
| caggcagaaa | atgcaacagt | aactgctggt | ttgcccttg | atgttatcag | agcagtagca | 1860 |
| agtgctactg | tatcagctga | gctatcactg | cctgggcata | agaaaagca | gcacaaacca | 1920 |
| acacagagtg | atctagacat | cgctgatggc | agcctaggga | acactctccc | caggggtgct | 1980 |
| gaagctttgc | ctaaccctag | ggacagcacc | attgtgagtg | gcctatatt | acagattgaa | 2040 |
| agtatctgtt | ctcttgcaga | aggtgatgta | tcttacaatt | cccaaatagc | agagatattc | 2100 |

```
aactctgtac aaaatgagcc ccagaaacct tcacctgatc agcaagtaat taatagtcaa    2160
caagaagaac aagtagataa ggttgctgaa aataaagact taagtttct gaaagacaag     2220 tgtatgcagt gtacagatgt tcctcatgaa gtcactgaac agccagagcc actgcagcct    2280
ttagagacaa catctgatga gtatgttgaa gcaaacggag aaatcctaga ggaaagcagt    2340
aaggagaatc ctggtgaaaa agagatgact aaggacatat tgtgttcacc agctgctgtt    2400
cagcaagatc ctcaacctca ggaaattgac acagccagca gtaagtcagg acacagtttt    2460
tctacagtaa atgagattaa tgatgaaaat gaacctgtct catacctaca tgaccagctg    2520
ttagaacttc taaaagagtt tccttatggc attgaaacta ttgccaggcc tgaagtttat    2580
gtgggccaac aaaagacaca tgaaatctta gaaaatcaaa ctggtagtaa aactggtaat    2640
gtgtctgggg ataacacaga ccaaataaaa attacagtat taaactcaga acaaatcaaa    2700
gaattatttc ctgaagagga tcagccatgt gatgtagaca aattggcaga acccgagaat    2760
acaaaaatca ttgcagaagt aaagagcctg tgtgattcac aggtccccag agaagaaagt    2820
cacaaccctg gaatgttgga tctggagaaa gataaaatcc attgctgtgc cttgggctgg    2880
ctctcaatgg tttatgaagg tgtgccacag tgtcagtgca gttccatgga agagaaagag    2940
aaagaccagt gttctttgga aatctctaat tgcaaacaag gagagcaggc ctgcaatagt    3000
ggaatcacta tttttgaaat taatcctatt tctaataact caaaaagtcc tctgatccaa    3060
gaatctgaga aaggccattt ttctgacata catggtgaaa agataaaaac atctgaaaca    3120
aaaaacagca gctcaccaag ggtagaacag gaattaactg gtcatttttc aatgaaatgt    3180
taccagaaag ataaatctac aacaaaacag gatagctcac tgaaaacaga gcaaaaaata    3240
aaaaatcttt cttctaaatg tgacaaacca aatcccttaa aaagcagtaa ataccaacc     3300 cctgaaacat ttaatgtggt aacttccaac tctgataaaa atatgccagc attttctaaa    3360
caagattctc agggaagcct gcagaagaaa cacctattcc aagactcaga tccagtaaaa    3420
ggacatgtat ggcttttgcc aaataaagat ccacgcagga gaataccctt tttagtacag    3480
tcagtatcac cagaaaagaa aaagttaaaa ttcaaatcgg gtagctccaa actgaaatat    3540
tttgaaaaaa gaaaaatgga ccatttgctt atctcagatg tggaaataaa aagaagaaa    3600 tacgaaaaac aagagcagaa caaaaatgct ggaggcacac tcaaattatg tagtactctg    3660
actgaaccaa atgaaagagc ctgtgctaaa gaaaagatag tgacaaattc tgagccctca    3720
gactcaaagg gaagctcctc taagagtact agagttataa ctgtgcagga atatttacag    3780
cggaaaaaag acaaacatgt aataggaaat aatgcctcca aaaacatctg tgtagaaaat    3840
gtgccatgtg actctgaacc catgaagtcc agtaaacatt ctgcatcacc tagtttggga    3900
aaattaattg agggccaggg tgtcagtgca gagactttaa aagaagtaga acataattcc    3960
accagccatg gcaaaaatct caagacccac cgttctgagg agactaggcc atacagtgtg    4020
tcaaatagta agagaaatt ttataggaca catccagaca atcttacat tgataaagct    4080 aaattagaaa gattgaccag tatgagtagt aagtccagcc agctccaggt aaaggaaaaa    4140
aggaaacagt acctgaatcg agttgcattc aaatgcacag aacaggaaag catttgtctc    4200
accaaattgg acagtgcatc caagaagctt agtaaagaga agaaaagag tacagcatgt    4260 gcacccatga caaaagacta cacacacaag cccatgttgg agtttaaatt atgtccagat    4320
gtgctattga agaatacaag ctccattgac aaagggatg atccaaggcc tgggcctgag    4380
aaggagcgag cacctgtgca agtttcagga ataaaaacta caaagaagaa ctggtaaaa     4440
```

```
tgtatcccaa caaggacaaa gatgcccgaa tcaagtgaac aaacagatcg ggctgactca    4500
agactctcta agagaagctt cagtgcagat gaatttgaaa ctctacaaaa cccagtaaaa    4560
gactcaaatg tcatgttccg gactttcaaa agatgtacc tggagaagag aagcaggagc     4620
ctggggagca gtccagtgaa gtag                                            4644

<210> SEQ ID NO 26
<211> LENGTH: 112
<212> TYPE: DNA
<213> ORGANISM: Cricetulus griseus

<400> SEQUENCE: 26
tgctgggatt taaggggaaa gctttaataa aagatcttta tttgtatttc ttgcagattt     60
gtgacattca aaaccacaga ctatgcaaca ctactactaa accaggtcaa at            112

<210> SEQ ID NO 27
<211> LENGTH: 36
<212> TYPE: DNA
<213> ORGANISM: Cricetulus griseus

<400> SEQUENCE: 27
cttcgggata gagtggtttt gcttttacca ccagga                               36

<210> SEQ ID NO 28
<211> LENGTH: 221
<212> TYPE: PRT
<213> ORGANISM: Homo sapiens

<400> SEQUENCE: 28

Met Phe Gly Phe His Lys Pro Lys Met Tyr Arg Ser Ile Glu Gly Cys
1               5                   10                  15

Cys Ile Cys Arg Ala Lys Ser Ser Ser Ser Arg Phe Thr Asp Ser Lys
            20                  25                  30

Arg Tyr Glu Lys Asp Phe Gln Ser Cys Phe Gly Leu His Glu Thr Arg
        35                  40                  45

Ser Gly Asp Ile Cys Asn Ala Cys Val Leu Leu Val Lys Arg Trp Lys
    50                  55                  60

Lys Leu Pro Ala Gly Ser Lys Lys Asn Trp Asn His Val Val Asp Ala
65                  70                  75                  80

Arg Ala Gly Pro Ser Leu Lys Thr Thr Leu Lys Pro Lys Lys Val Lys
                85                  90                  95

Thr Leu Ser Gly Asn Arg Ile Lys Ser Asn Gln Ile Ser Lys Leu Gln
            100                 105                 110

Lys Glu Phe Lys Arg His Asn Ser Asp Ala His Ser Thr Thr Ser Ser
        115                 120                 125

Ala Ser Pro Ala Gln Ser Pro Cys Tyr Ser Asn Gln Ser Asp Asp Gly
    130                 135                 140

Ser Asp Thr Glu Met Ala Ser Gly Ser Asn Arg Thr Pro Val Phe Ser
145                 150                 155                 160

Phe Leu Asp Leu Thr Tyr Trp Lys Arg Gln Lys Ile Cys Cys Gly Ile
                165                 170                 175

Ile Tyr Lys Gly Arg Phe Gly Glu Val Leu Ile Asp Thr His Leu Phe
            180                 185                 190

Lys Pro Cys Cys Ser Asn Lys Lys Ala Ala Ala Glu Lys Pro Glu Glu
        195                 200                 205

Gln Gly Pro Glu Pro Leu Pro Ile Ser Thr Gln Glu Trp
    210                 215                 220
```

<210> SEQ ID NO 29
<211> LENGTH: 221
<212> TYPE: PRT
<213> ORGANISM: Mus musculus

<400> SEQUENCE: 29

Met Phe Gly Phe His Lys Pro Lys Met Tyr Arg Ser Ile Glu Gly Cys
1               5                   10                  15

Cys Ile Cys Arg Ala Lys Ser Ser Ser Arg Phe Thr Asp Ser Lys
            20                  25                  30

Arg Tyr Glu Lys Asp Phe Gln Ser Cys Phe Gly Leu His Glu Thr Arg
        35                  40                  45

Ser Gly Asp Ile Cys Asn Ala Cys Val Leu Leu Val Lys Arg Trp Lys
    50                  55                  60

Lys Leu Pro Ala Gly Ser Lys Lys Asn Trp Asn His Val Val Asp Ala
65                  70                  75                  80

Arg Ala Gly Pro Ser Leu Lys Thr Thr Leu Lys Pro Lys Lys Val Lys
                85                  90                  95

Thr Leu Ser Gly Asn Arg Met Lys Ser Asn Gln Ile Ser Lys Leu Gln
            100                 105                 110

Lys Glu Phe Lys Arg His Asn Ser Asp Ala His Ser Thr Thr Ser Ser
        115                 120                 125

Ala Ser Pro Ala Gln Ser Pro Cys Tyr Ser Asn Gln Ser Asp Glu Gly
    130                 135                 140

Ser Asp Thr Glu Met Ala Ser Ser Ser Asn Arg Thr Pro Val Phe Ser
145                 150                 155                 160

Phe Leu Asp Leu Thr Tyr Trp Lys Arg Gln Lys Ile Cys Cys Gly Ile
                165                 170                 175

Ile Tyr Lys Gly Arg Phe Gly Glu Val Leu Ile Asp Thr His Leu Phe
            180                 185                 190

Lys Pro Cys Cys Ser Ser Lys Lys Ala Ala Ala Glu Lys Pro Glu Glu
        195                 200                 205

Gln Gly Pro Ala Pro Leu Pro Ile Ser Thr Gln Glu Trp
    210                 215                 220

<210> SEQ ID NO 30
<211> LENGTH: 221
<212> TYPE: PRT
<213> ORGANISM: Cricetulus griseus

<400> SEQUENCE: 30

Met Phe Gly Phe His Lys Pro Lys Met Tyr Arg Ser Ile Glu Gly Cys
1               5                   10                  15

Cys Ile Cys Arg Ala Lys Ser Ser Ser Arg Phe Thr Asp Ser Lys
            20                  25                  30

Arg Tyr Glu Lys Asp Phe Gln Ser Cys Phe Gly Leu His Glu Thr Arg
        35                  40                  45

Ser Gly Asp Ile Cys Asn Ala Cys Val Leu Leu Val Lys Arg Trp Lys
    50                  55                  60

Lys Leu Pro Ala Gly Ser Lys Lys Asn Trp Asn His Val Ser His Ser
65                  70                  75                  80

Arg Ala Gly Pro Ser Leu Lys Thr Thr Leu Lys Pro Lys Lys Val Lys
                85                  90                  95

Thr Leu Ser Gly Asn Arg Met Lys Ser Asn Gln Ile Ser Lys Leu Gln
            100                 105                 110

```
Lys Glu Phe Lys Arg His Asn Ser Asp Ala His Ser Thr Thr Ser Ser
            115                 120                 125

Ala Ser Pro Ala Gln Ser Pro Cys Tyr Ser Asn Gln Ser Asp Asp Gly
        130                 135                 140

Ser Asp Thr Glu Met Ala Ser Ser Asn Arg Thr Pro Val Phe Ser
145                 150                 155                 160

Phe Leu Asp Leu Thr Tyr Trp Lys Arg Gln Lys Ile Cys Cys Gly Ile
                165                 170                 175

Ile Tyr Lys Gly Arg Phe Gly Glu Val Leu Ile Asp Thr His Leu Phe
            180                 185                 190

Lys Pro Cys Cys Ser Ser Lys Lys Ala Ala Pro Glu Lys Pro Glu Glu
        195                 200                 205

Gln Gly Pro Ala Pro Leu Pro Ile Ser Thr Gln Glu Trp
    210                 215                 220
```

<210> SEQ ID NO 31
<211> LENGTH: 1236
<212> TYPE: DNA
<213> ORGANISM: Cricetulus griseus

<400> SEQUENCE: 31

| | |
|---|---:|
| ctcagaagaa aagatgtttg gttttcacaa gccaaagatg taccgaagta tagagggctg | 60 |
| ctgtatctgc agagccaagt cctccagctc tcggttcacg acagtaaac gttatgaaaa | 120 |
| ggacttccag agctgttttg ggttgcacga gactcgctca ggagatatct gcaatgcctg | 180 |
| tgtgctgctt gtgaaaagat ggaagaagtt gccagcagga tcaaaaaaaa actggaatca | 240 |
| tgtgtcacac tcaagggcag gacccagtct aaagacaaca ttgaaaccaa agaaagtgaa | 300 |
| aactctatct ggaaacagga tgaaaagcaa ccagatcagt aaactgcaga aggagtttaa | 360 |
| acgccacaac tctgatgctc acagtaccac ctcaagtgcc tcgccagccc agtctccctg | 420 |
| ctacagtaac cagtcagatg gatggctcaga cacagagatg gcttccagct ctaacagaac | 480 |
| tccagttttt tccttcttag atcttaccta ctggaaaaga cagaaaatat gttgtgggat | 540 |
| catctataag ggccgttttg gggaagtcct catcgacacg catctcttca agccttgctg | 600 |
| cagcagtaag aaggcagctc ctgagaagcc tgaggaacag ggaccagcgc tctgcccat | 660 |
| ctctactcag gagtggtgac tgaggttcat gcagaaggga acaaagagca atttaaactt | 720 |
| tgaaaagacc acaaagcaac agactgaccc tcctattttt aacttggata cctgctattc | 780 |
| tgccaaaaga catttctag aatagttttt aatgggttac ccatccccc atccaacaaa | 840 |
| ctcggaagcc agttctagct tactgcaaga agagagtgta cataatattt aatatgctga | 900 |
| gtatttcata ggaaggctga atgctgctgt aaagtgctct ttaagtcttt ttttttttt | 960 |
| aatcccctct aatgaatgag attaggggg tttcagggga cagagatggg atttgttgtg | 1020 |
| tgataaacca tatgtagttt agtctttctg tggagaggca gtggttgggg catttaaat | 1080 |
| ggctggctac acttgttttc ccctcatggt aatttgtcat aactcagtag cacgacctgc | 1140 |
| ccctagaagt agttaaagat ttttaaatgc taaggcgttg ccaaggttct gatgattcag | 1200 |
| acctgtacta ctgattatta agcaggacag actgag | 1236 |

<210> SEQ ID NO 32
<211> LENGTH: 855
<212> TYPE: PRT
<213> ORGANISM: Cricetulus griseus

<400> SEQUENCE: 32

```
Met Gly Ser Asn Arg Gly Arg Lys Ala Gly Ser Ser Lys Asp Phe
1               5                   10                  15

Gly Ala Arg Leu Lys Tyr Ser Ser Leu Glu Asn Met Asn Gly Phe
                20                  25                  30

Glu Glu Gly Val Glu Phe Leu Pro Val Asn Asn Ala Lys Lys Val Glu
            35                  40                  45

Lys Arg Gly Pro Arg Arg Cys Val Val Leu Val Val Leu Leu Val Ser
        50                  55                  60

Phe Leu Phe Leu Ser Leu Val Ala Gly Phe Leu Val Trp His Phe Leu
65                  70                  75                  80

Tyr Ser Asn Val Arg Ile Gln Lys Val Phe Asn Gly His Leu Arg Val
                85                  90                  95

Thr Asn Glu Asn Phe Leu Asp Ala Tyr Glu Asn Ser Asn Ser Thr Glu
            100                 105                 110

Phe Lys Asp Leu Ala Asn Gln Val Lys Glu Ala Leu Lys Leu Leu Tyr
        115                 120                 125

Ser Glu Val Pro Val Leu Gly Pro Tyr His Lys Arg Ser Ala Val Thr
        130                 135                 140

Ala Phe Ser Glu Gly Ser Val Ile Ala Tyr Tyr Trp Ser Glu Phe Ser
145                 150                 155                 160

Ile Pro Pro His Leu Ala Glu Glu Val Asp Arg Ala Met Ala Val Glu
                165                 170                 175

Arg Val Val Thr Leu Pro Pro Arg Ala Arg Ala Leu Lys Ser Phe Val
            180                 185                 190

Leu Thr Ser Val Val Ala Phe Pro Thr Asp Pro Arg Leu Leu Gly Arg
        195                 200                 205

Thr Gln Asp Asn Ser Cys Asn Phe Ala Leu His Ala His Gly Gly Glu
        210                 215                 220

Val Met Arg Phe Thr Thr Pro Gly Phe Pro Asn Ser Pro Tyr Pro Ala
225                 230                 235                 240

His Ala Arg Cys Gln Trp Val Leu Arg Gly Asp Ala Asp Ser Val Leu
                245                 250                 255

Ser Leu Thr Phe Arg Ser Phe Asp Val Ala Pro Cys Asp Glu Leu Gly
            260                 265                 270

Asn Asp Leu Val Thr Val Tyr Asp Thr Leu Ser Pro Met Glu Pro His
        275                 280                 285

Ala Val Val Arg Leu Cys Gly Thr Tyr Pro Pro Ser Tyr Asn Leu Thr
        290                 295                 300

Phe Leu Ser Ser Gln Asn Val Phe Leu Val Thr Leu Ile Thr Asn Thr
305                 310                 315                 320

Asp Arg Arg His Pro Gly Phe Glu Ala Thr Phe Phe Gln Leu Pro Lys
                325                 330                 335

Met Arg Ser Cys Gly Gly Ser Leu Ser Glu Ala Gln Gly Leu Phe Ser
            340                 345                 350

Ser Pro Tyr Tyr Pro Gly His Tyr Pro Pro Asn Ile Asp Cys Thr Trp
        355                 360                 365

Asn Ile Lys Val Pro Asn Asn Arg Asn Val Lys Val Arg Phe Lys Leu
        370                 375                 380

Phe Tyr Leu Val Asp Pro Asn Ile Pro Leu Gly Thr Cys Pro Lys Asp
385                 390                 395                 400

Tyr Val Glu Ile Asn Gly Glu Arg Tyr Cys Gly Glu Lys Ser Gln Phe
                405                 410                 415
```

-continued

Val Val Ser Ser Asn Ser Ser Lys Ile Thr Val Arg Phe His Ser Asp
                420                 425                 430

His Ser Tyr Thr Asp Thr Gly Phe Leu Ala Glu Tyr Leu Ser Tyr Asp
            435                 440                 445

Ser Asn Asp Pro Cys Pro Gly Met Phe Met Cys Asn Thr Gly Arg Cys
        450                 455                 460

Ile Arg Lys Asp Leu Arg Cys Asp Gly Trp Ala Asp Cys Pro Asp Tyr
465                 470                 475                 480

Ser Asp Glu His Phe Cys Arg Cys Asn Thr Thr His Gln Phe Met Cys
                485                 490                 495

Lys Asn Lys Leu Cys Lys Pro Leu Phe Trp Val Cys Asp Asn Ile Asn
            500                 505                 510

Asp Cys Gly Asp Gly Ser Asp Glu Glu Gly Cys Ser Cys Pro Ala Glu
        515                 520                 525

Thr Phe Lys Cys Ser Asn Gly Lys Cys Leu Pro Gln Ser Gln Lys Cys
        530                 535                 540

Asp Gly Lys Asp Asn Cys Gly Asp Gly Ser Asp Glu Ala Ser Cys Asp
545                 550                 555                 560

Arg Val Lys Val Val Ser Cys Thr Lys Tyr Thr Tyr Arg Cys His Asn
                565                 570                 575

Gly Leu Cys Leu Ser Lys Gly Asn Pro Glu Cys Asp Gly Lys Lys Asp
            580                 585                 590

Cys Ser Asp Gly Ser Asp Glu Lys Asn Cys Asp Cys Gly Leu Arg Ser
        595                 600                 605

Phe Thr Lys Gln Ala Arg Val Val Gly Gly Thr Asn Ala Asp Glu Gly
        610                 615                 620

Glu Trp Pro Trp Gln Val Ser Leu His Ala Leu Gly Gln Gly His Leu
625                 630                 635                 640

Cys Gly Ala Ser Leu Ile Ser Pro Asn Trp Leu Val Ser Ala Ala His
                645                 650                 655

Cys Phe Met Asp Asp Arg Asn Phe Lys Tyr Ser Asp His Thr Lys Trp
            660                 665                 670

Thr Ala Phe Leu Gly Leu Leu Asp Gln Ser Lys Arg Ser Ser Thr Gly
        675                 680                 685

Val Gln Glu His Lys Leu Lys Arg Ile Ile Thr His Pro Leu Phe Asn
        690                 695                 700

Glu Ile Thr Phe Asp Tyr Asp Ile Ala Leu Leu Glu Leu Glu Lys Pro
705                 710                 715                 720

Ala Glu Tyr Ser Thr Val Val Arg Pro Ile Cys Leu Pro Asp Thr Thr
                725                 730                 735

His Val Phe Pro Ala Gly Lys Ala Ile Trp Val Thr Gly Trp Gly His
            740                 745                 750

Thr Gln Glu Gly Gly Thr Gly Ala Leu Ile Leu Gln Lys Gly Glu Ile
        755                 760                 765

Arg Val Ile Asn Gln Thr Thr Cys Glu Asp Leu Met Pro Gln Gln Ile
770                 775                 780

Thr Pro Arg Met Met Cys Val Gly Phe Leu Ser Gly Gly Val Asp Ser
785                 790                 795                 800

Cys Gln Gly Asp Ser Gly Gly Pro Leu Ser Ser Val Glu Thr Glu Gly
                805                 810                 815

Arg Ile Phe Gln Ala Gly Val Val Ser Trp Gly Glu Gly Cys Ala Gln
            820                 825                 830

Arg Asn Lys Pro Gly Val Tyr Thr Arg Leu Pro Ala Val Arg Asp Trp

```
                835                 840                 845
Ile Lys Glu Gln Thr Gly Val
            850                 855

<210> SEQ ID NO 33
<211> LENGTH: 855
<212> TYPE: PRT
<213> ORGANISM: Homo sapiens

<400> SEQUENCE: 33

Met Gly Ser Asp Arg Ala Arg Lys Gly Gly Gly Pro Lys Asp Phe
1               5                   10                  15

Gly Ala Gly Leu Lys Tyr Asn Ser Arg His Glu Lys Val Asn Gly Leu
                20                  25                  30

Glu Glu Gly Val Glu Phe Leu Pro Val Asn Asn Val Lys Lys Val Glu
            35                  40                  45

Lys His Gly Pro Gly Arg Trp Val Val Leu Ala Ala Val Leu Ile Gly
    50                  55                  60

Leu Leu Leu Val Leu Leu Gly Ile Gly Phe Leu Val Trp His Leu Gln
65                  70                  75                  80

Tyr Arg Asp Val Arg Val Gln Lys Val Phe Asn Gly Tyr Met Arg Ile
                85                  90                  95

Thr Asn Glu Asn Phe Val Asp Ala Tyr Glu Asn Ser Asn Ser Thr Glu
            100                 105                 110

Phe Val Ser Leu Ala Ser Lys Val Lys Asp Ala Leu Lys Leu Leu Tyr
        115                 120                 125

Ser Gly Val Pro Phe Leu Gly Pro Tyr His Lys Glu Ser Ala Val Thr
    130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
            180                 185                 190

Val Thr Ser Val Val Ala Phe Pro Thr Asp Ser Lys Thr Val Gln Arg
        195                 200                 205

Thr Gln Asp Asn Ser Cys Ser Phe Gly Leu His Ala Arg Gly Val Glu
    210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
            260                 265                 270

Ser Asp Leu Val Thr Val Tyr Asn Thr Leu Ser Pro Met Glu Pro His
        275                 280                 285

Ala Leu Val Gln Leu Cys Gly Thr Tyr Pro Pro Ser Tyr Asn Leu Thr
    290                 295                 300

Phe His Ser Ser Gln Asn Val Leu Leu Ile Thr Leu Ile Thr Asn Thr
305                 310                 315                 320

Glu Arg Arg His Pro Gly Phe Glu Ala Thr Phe Phe Gln Leu Pro Arg
                325                 330                 335

Met Ser Ser Cys Gly Gly Arg Leu Arg Lys Ala Gln Gly Thr Phe Asn
            340                 345                 350
```

```
Ser Pro Tyr Tyr Pro Gly His Tyr Pro Pro Asn Ile Asp Cys Thr Trp
    355                 360                 365

Asn Ile Glu Val Pro Asn Asn Gln His Val Lys Val Arg Phe Lys Phe
370                 375                 380

Phe Tyr Leu Leu Glu Pro Gly Val Pro Ala Gly Thr Cys Pro Lys Asp
385                 390                 395                 400

Tyr Val Glu Ile Asn Gly Glu Lys Tyr Cys Gly Glu Arg Ser Gln Phe
                405                 410                 415

Val Val Thr Ser Asn Ser Asn Lys Ile Thr Val Arg Phe His Ser Asp
            420                 425                 430

Gln Ser Tyr Thr Asp Thr Gly Phe Leu Ala Glu Tyr Leu Ser Tyr Asp
        435                 440                 445

Ser Ser Asp Pro Cys Pro Gly Gln Phe Thr Cys Arg Thr Gly Arg Cys
    450                 455                 460

Ile Arg Lys Glu Leu Arg Cys Asp Gly Trp Ala Asp Cys Thr Asp His
465                 470                 475                 480

Ser Asp Glu Leu Asn Cys Ser Cys Asp Ala Gly His Gln Phe Thr Cys
                485                 490                 495

Lys Asn Lys Phe Cys Lys Pro Leu Phe Trp Val Cys Asp Ser Val Asn
            500                 505                 510

Asp Cys Gly Asp Asn Ser Asp Glu Gln Gly Cys Ser Cys Pro Ala Gln
        515                 520                 525

Thr Phe Arg Cys Ser Asn Gly Lys Cys Leu Ser Lys Ser Gln Gln Cys
    530                 535                 540

Asn Gly Lys Asp Asp Cys Gly Asp Gly Ser Asp Glu Ala Ser Cys Pro
545                 550                 555                 560

Lys Val Asn Val Val Thr Cys Thr Lys His Thr Tyr Arg Cys Leu Asn
                565                 570                 575

Gly Leu Cys Leu Ser Lys Gly Asn Pro Glu Cys Asp Gly Lys Glu Asp
            580                 585                 590

Cys Ser Asp Gly Ser Asp Glu Lys Asp Cys Asp Cys Gly Leu Arg Ser
        595                 600                 605

Phe Thr Arg Gln Ala Arg Val Val Gly Gly Thr Asp Ala Asp Glu Gly
    610                 615                 620

Glu Trp Pro Trp Gln Val Ser Leu His Ala Leu Gly Gln Gly His Ile
625                 630                 635                 640

Cys Gly Ala Ser Leu Ile Ser Pro Asn Trp Leu Val Ser Ala Ala His
                645                 650                 655

Cys Tyr Ile Asp Asp Arg Gly Phe Arg Tyr Ser Asp Pro Thr Gln Trp
            660                 665                 670

Thr Ala Phe Leu Gly Leu His Asp Gln Ser Gln Arg Ser Ala Pro Gly
        675                 680                 685

Val Gln Glu Arg Arg Leu Lys Arg Ile Ile Ser His Pro Phe Phe Asn
    690                 695                 700

Asp Phe Thr Phe Asp Tyr Asp Ile Ala Leu Leu Glu Leu Glu Lys Pro
705                 710                 715                 720

Ala Glu Tyr Ser Ser Met Val Arg Pro Ile Cys Leu Pro Asp Ala Ser
                725                 730                 735

His Val Phe Pro Ala Gly Lys Ala Ile Trp Val Thr Gly Trp Gly His
            740                 745                 750

Thr Gln Tyr Gly Gly Thr Gly Ala Leu Ile Leu Gln Lys Gly Glu Ile
        755                 760                 765

Arg Val Ile Asn Gln Thr Thr Cys Glu Asn Leu Leu Pro Gln Gln Ile
```

```
                    770                 775                 780
Thr Pro Arg Met Met Cys Val Gly Phe Leu Ser Gly Val Asp Ser
785                 790                 795                 800

Cys Gln Gly Asp Ser Gly Pro Leu Ser Ser Val Glu Ala Asp Gly
                805                 810                 815

Arg Ile Phe Gln Ala Gly Val Val Ser Trp Gly Asp Gly Cys Ala Gln
                820                 825                 830

Arg Asn Lys Pro Gly Val Tyr Thr Arg Leu Pro Leu Phe Arg Asp Trp
                835                 840                 845

Ile Lys Glu Asn Thr Gly Val
                850                 855

<210> SEQ ID NO 34
<211> LENGTH: 855
<212> TYPE: PRT
<213> ORGANISM: Mus musculus

<400> SEQUENCE: 34

Met Gly Ser Asn Arg Gly Arg Lys Ala Gly Gly Ser Gln Asp Phe
1                 5                  10                  15

Gly Ala Gly Leu Lys Tyr Asn Ser Arg Leu Glu Asn Met Asn Gly Phe
                20                  25                  30

Glu Glu Gly Val Glu Phe Leu Pro Ala Asn Asn Ala Lys Lys Val Glu
                35                  40                  45

Lys Arg Gly Pro Arg Arg Trp Val Val Leu Val Ala Val Leu Phe Ser
50                  55                  60

Phe Leu Leu Leu Ser Leu Met Ala Gly Leu Leu Val Trp His Phe His
65                  70                  75                  80

Tyr Arg Asn Val Arg Val Gln Lys Val Phe Asn Gly His Leu Arg Ile
                85                  90                  95

Thr Asn Glu Ile Phe Leu Asp Ala Tyr Glu Asn Ser Thr Ser Thr Glu
                100                 105                 110

Phe Ile Ser Leu Ala Ser Gln Val Lys Glu Ala Leu Lys Leu Leu Tyr
                115                 120                 125

Asn Glu Val Pro Val Leu Gly Pro Tyr His Lys Lys Ser Ala Val Thr
                130                 135                 140

Ala Phe Ser Glu Gly Ser Val Ile Ala Tyr Tyr Trp Ser Glu Phe Ser
145                 150                 155                 160

Ile Pro Pro His Leu Ala Glu Glu Val Asp Arg Ala Met Ala Val Glu
                165                 170                 175

Arg Val Val Thr Leu Pro Pro Arg Ala Arg Ala Leu Lys Ser Phe Val
                180                 185                 190

Leu Thr Ser Val Val Ala Phe Pro Ile Asp Pro Arg Met Leu Gln Arg
                195                 200                 205

Thr Gln Asp Asn Ser Cys Ser Phe Ala Leu His Ala His Gly Ala Ala
                210                 215                 220

Val Thr Arg Phe Thr Thr Pro Gly Phe Pro Asn Ser Pro Tyr Pro Ala
225                 230                 235                 240

His Ala Arg Cys Gln Trp Val Leu Arg Gly Asp Ala Asp Ser Val Leu
                245                 250                 255

Ser Leu Thr Phe Arg Ser Phe Asp Val Ala Pro Cys Asp Glu His Gly
                260                 265                 270

Ser Asp Leu Val Thr Val Tyr Asp Ser Leu Ser Pro Met Glu Pro His
                275                 280                 285
```

```
Ala Val Val Arg Leu Cys Gly Thr Phe Ser Pro Ser Tyr Asn Leu Thr
    290             295                 300
Phe Leu Ser Ser Gln Asn Val Phe Leu Val Thr Leu Ile Thr Asn Thr
305             310                 315                     320
Asp Arg Arg His Pro Gly Phe Glu Ala Thr Phe Phe Gln Leu Pro Lys
                325                 330                 335
Met Ser Ser Cys Gly Gly Phe Leu Ser Asp Thr Gln Gly Thr Phe Ser
            340                 345                 350
Ser Pro Tyr Tyr Pro Gly His Tyr Pro Pro Asn Ile Asn Cys Thr Trp
        355                 360                 365
Asn Ile Lys Val Pro Asn Asn Arg Asn Val Lys Val Arg Phe Lys Leu
370                 375                 380
Phe Tyr Leu Val Asp Pro Asn Val Pro Val Gly Ser Cys Thr Lys Asp
385                 390                 395                 400
Tyr Val Glu Ile Asn Gly Glu Lys Tyr Cys Gly Glu Arg Ser Gln Phe
                405                 410                 415
Val Val Ser Ser Asn Ser Ser Lys Ile Thr Val His Phe His Ser Asp
            420                 425                 430
His Ser Tyr Thr Asp Thr Gly Phe Leu Ala Glu Tyr Leu Ser Tyr Asp
        435                 440                 445
Ser Asn Asp Pro Cys Pro Gly Met Phe Met Cys Lys Thr Gly Arg Cys
450                 455                 460
Ile Arg Lys Glu Leu Arg Cys Asp Gly Trp Ala Asp Cys Pro Asp Tyr
465                 470                 475                 480
Ser Asp Glu Arg Tyr Cys Arg Cys Asn Ala Thr His Gln Phe Thr Cys
                485                 490                 495
Lys Asn Gln Phe Cys Lys Pro Leu Phe Trp Val Cys Asp Ser Val Asn
            500                 505                 510
Asp Cys Gly Asp Gly Ser Asp Glu Glu Gly Cys Ser Cys Pro Ala Gly
        515                 520                 525
Ser Phe Lys Cys Ser Asn Gly Lys Cys Leu Pro Gln Ser Gln Lys Cys
530                 535                 540
Asn Gly Lys Asp Asn Cys Gly Asp Gly Ser Asp Glu Ala Ser Cys Asp
545                 550                 555                 560
Ser Val Asn Val Val Ser Cys Thr Lys Tyr Thr Tyr Arg Cys Gln Asn
                565                 570                 575
Gly Leu Cys Leu Ser Lys Gly Asn Pro Glu Cys Asp Gly Lys Thr Asp
            580                 585                 590
Cys Ser Asp Gly Ser Asp Glu Lys Asn Cys Asp Cys Gly Leu Arg Ser
        595                 600                 605
Phe Thr Lys Gln Ala Arg Val Val Gly Gly Thr Asn Ala Asp Glu Gly
610                 615                 620
Glu Trp Pro Trp Gln Val Ser Leu His Ala Leu Gly Gln Gly His Leu
625                 630                 635                 640
Cys Gly Ala Ser Leu Ile Ser Pro Asp Trp Leu Val Ser Ala Ala His
                645                 650                 655
Cys Phe Gln Asp Asp Lys Asn Phe Lys Tyr Ser Asp Tyr Thr Met Trp
            660                 665                 670
Thr Ala Phe Leu Gly Leu Leu Asp Gln Ser Lys Arg Ser Ala Ser Gly
        675                 680                 685
Val Gln Glu Leu Lys Leu Lys Arg Ile Ile Thr His Pro Ser Phe Asn
690                 695                 700
Asp Phe Thr Phe Asp Tyr Asp Ile Ala Leu Leu Glu Leu Glu Lys Ser
```

```
                705                 710                 715                 720
Val Glu Tyr Ser Thr Val Val Arg Pro Ile Cys Leu Pro Asp Ala Thr
                    725                 730                 735

His Val Phe Pro Ala Gly Lys Ala Ile Trp Val Thr Gly Trp Gly His
                740                 745                 750

Thr Lys Glu Gly Gly Thr Gly Ala Leu Ile Leu Gln Lys Gly Glu Ile
                755                 760                 765

Arg Val Ile Asn Gln Thr Thr Cys Glu Asp Leu Met Pro Gln Gln Ile
                770                 775                 780

Thr Pro Arg Met Met Cys Val Gly Phe Leu Ser Gly Gly Val Asp Ser
785                 790                 795                 800

Cys Gln Gly Asp Ser Gly Gly Pro Leu Ser Ser Ala Glu Lys Asp Gly
                    805                 810                 815

Arg Met Phe Gln Ala Gly Val Val Ser Trp Gly Glu Gly Cys Ala Gln
                820                 825                 830

Arg Asn Lys Pro Gly Val Tyr Thr Arg Leu Pro Val Val Arg Asp Trp
                835                 840                 845

Ile Lys Glu His Thr Gly Val
                850                 855

<210> SEQ ID NO 35
<211> LENGTH: 1521
<212> TYPE: PRT
<213> ORGANISM: Mus musculus

<400> SEQUENCE: 35

Met Asn Trp Asn Thr Lys Gln Glu Asn Val Pro Lys Pro Pro Pro Tyr
1               5                   10                  15

Ser Lys Thr Gln Ser Ser Ile Leu Gln His Phe Leu Met Thr Ser Thr
                20                  25                  30

Thr Ser Gln Ser Ser Phe Asn Tyr Ser Pro His Asn Gln Glu Ala Ser
            35                  40                  45

Gln Thr Ser Phe Asn Tyr Ser Leu His Asn Gln Glu Ala Cys Met Tyr
        50                  55                  60

Ser Gly Asn Ser Asn Ser Val Ser Gln Pro Leu Leu Ser Gly Arg Asn
65                  70                  75                  80

Tyr Ile Thr Pro Gln Thr Gln Ile Ser Val Ser Asn Met Pro Thr Arg
                85                  90                  95

Thr Ile Val Ala Ser Gln Ser Ser Met Glu Arg Val Val Ser Thr Asn
                100                 105                 110

Gly Lys Gly Pro Gln Gln Pro Asn His Asn Leu Gln Thr Val Ser Ser
                115                 120                 125

Gly Ile Met Gln Asn Val Trp Leu Pro Ser His Thr Glu Ala Thr Ile
            130                 135                 140

Ser His Asn Pro Asp Gly Gly Thr Asn Met Pro Tyr Met His Pro Pro
145                 150                 155                 160

Gln Asn Gln Leu Val Thr Ser Asp Thr Tyr Ser Met Gln Leu Gln Met
                    165                 170                 175

Ala Pro Leu His Ser Gly Lys Val Pro Met Thr His Gln Gly Ser Gln
                180                 185                 190

Gly Leu Asn His Phe Ile Pro Asp Gln Leu Val Asp Trp Thr Gln Tyr
            195                 200                 205

Thr Ser Asn Glu Leu Ser Tyr Pro Glu Tyr Arg Pro Pro Pro Lys Gln
        210                 215                 220
```

```
Tyr Ser Tyr Ile Leu Pro Ala Thr Thr Ser Leu Gln Val Lys Asn Asn
225                 230                 235                 240

Gln Leu Pro Thr Tyr Thr Gln Ser Leu Gln Ser Lys His Ser Val Pro
            245                 250                 255

Leu Ser Ser His Gln Tyr Ala Ala Glu Ala Ser Lys Arg Leu Ser Ala
        260                 265                 270

Leu Pro Tyr Ser Cys Arg Tyr Glu Asn Gln His Val Gln Asn Ala Gln
    275                 280                 285

Pro Val Ser Lys His Leu Pro Met Glu Val Pro Gln Ser Ser Glu Val
290                 295                 300

His Ser Ser Glu Lys Lys Lys Asp Thr Tyr Arg Gly Phe Lys Gln Gln
305                 310                 315                 320

Trp Gln Asn Pro Asn Glu Lys Val Ser Ile Gly Gln Phe Ser Glu Val
                325                 330                 335

Lys Ile Asn Ile Lys Gln Pro Tyr Ser Glu Ser Val Arg Pro Ser Gly
            340                 345                 350

Asp Gly Val Gln Ala Leu Val Gln Asn Gln Glu Lys Arg Lys Tyr
        355                 360                 365

Thr Tyr Asn Pro Asn Thr Asn Gln Val Ile Asp Thr Asn Ala Thr Lys
370                 375                 380

Glu Lys Leu Val Arg Asp Ile Lys Ser Leu Val Glu Ile Lys Lys Lys
385                 390                 395                 400

Phe Ser Glu Leu Ala Arg Lys Ile Lys Ile Asn Lys Ser Leu Leu Met
                405                 410                 415

Ala Ala Gly Cys Ser Lys Thr Ala Asn Thr Ser Tyr Thr Glu Pro Ile
            420                 425                 430

Gln His Ser Glu Phe Ser Ala Lys Glu Met Ser Ala Lys Asn Gly Asn
        435                 440                 445

Asp Cys Ser Met Glu Leu Leu Ala Thr Cys Leu Ser Leu Trp Lys Asn
    450                 455                 460

Gln Pro Ser Lys Thr Thr Glu Glu Asn Val Pro Lys Pro Leu Glu Glu
465                 470                 475                 480

Lys Gln Cys Asn Thr Ser Arg Ile Ser Thr Thr Val Val Gly Ser Ala
                485                 490                 495

Asn Pro Thr Asn Glu Val His Val Lys Ser Leu Cys Ser Gly Val Gly
            500                 505                 510

Asn Ser Gln Lys Met Met Ser Ser Gln Thr Val Leu Pro Val Leu
        515                 520                 525

Ile Pro Ser Cys Glu Ser Ser Gly Val Ala Val Gly Lys Gly Thr Glu
530                 535                 540

Leu Gln Ile Ala Val Val Ser Pro Leu Val Leu Ser Asp Thr Asn Thr
545                 550                 555                 560

Leu Pro Gly Lys Asp Ser Val Pro Glu Val Leu Pro Glu Thr Leu Tyr
                565                 570                 575

Pro Val Val Lys Glu Gly Ser Val Cys Ser Leu Gln Thr Gln Pro Thr
            580                 585                 590

Glu Thr Val Ala Leu Pro Phe Asp Val Ile Gly Ala Val Ala Ser Asn
        595                 600                 605

Asn Ile Ser Ala Glu Ile Pro Leu Pro Val Asp Lys Glu Lys Gln His
    610                 615                 620

Lys Pro Ile Gln Gly Asp Pro Asp Ile Ala Asp Ser Ser Leu Gly Lys
625                 630                 635                 640

His Ser Pro Leu Gly Thr Glu Val Leu Pro Lys Pro Met Asp Ser Thr
```

```
              645                 650                 655
Ile Val Ser Gly Pro Met Leu Gln Ile Glu Ser Ile Cys Ser Leu Ala
            660                 665                 670

Glu Gly Asp Val Ser Tyr Asn Ser Gln Ile Ala Glu Ile Phe Asn Ser
            675                 680                 685

Val Gln Thr Glu Pro Gln Lys Pro Ser Pro Asn Gln Val Ile Asp Ser
690                 695                 700

Gln Gln Glu Gln Val Tyr Asp Thr Thr Glu Asn Lys Asp Phe Ser Leu
705                 710                 715                 720

Gln Lys Asp Lys Cys Val Gln Cys Thr Asp Val Pro His Glu Val Pro
            725                 730                 735

Glu Gln Pro Glu Pro Leu Gln Pro Glu Glu Pro Ala Ser Ser Glu Tyr
            740                 745                 750

Val Glu Ala Asn Arg Glu Ala Thr Glu Glu Ser Cys Arg Glu Tyr Thr
            755                 760                 765

Gly Arg Lys Glu Ser Thr Ala Lys Asp Val Cys Leu Pro Ala Ala Ile
            770                 775                 780

Gln Gln Asp Pro His Pro Arg Glu Thr Asp Met Phe Ser Lys Ser Asp
785                 790                 795                 800

His Ser Leu Pro Ala Ile Asn Glu Ile Asn Asp Ser Glu Pro Ile
            805                 810                 815

Ser Tyr Leu His Asp Gln Leu Ser Glu Leu Leu Lys Glu Phe Pro Tyr
            820                 825                 830

Gly Ile Glu Thr Phe Asn Arg His Glu Val Ser Leu Asp Gln Gln Lys
            835                 840                 845

Thr His Lys Ile Val Glu Asn Gln Thr Gly Gly Lys Thr Ser Asn Val
            850                 855                 860

Ser Gly Asp Ser Thr Asp Gln Ile Lys Ile Thr Val Leu Asn Ser Glu
865                 870                 875                 880

Gln Ile Lys Glu Leu Phe Pro Glu Asp Gln Pro Cys Asp Lys Leu
            885                 890                 895

Ala Glu Pro Glu Asn Lys Glu Ile Val Ala Glu Val Lys Ser Pro Cys
            900                 905                 910

Asp Ser Gln Ile Pro Arg Glu Glu Ser His Asp Leu Gly Met Leu Asp
            915                 920                 925

Pro Glu Lys Asp Lys Ile His Cys Cys Ala Leu Gly Trp Leu Ser Met
            930                 935                 940

Val Tyr Glu Gly Val Pro Gln Cys His Cys Ser Ser Thr Glu Lys Lys
945                 950                 955                 960

Glu Lys Asp Gln Cys Leu Asp Ile Asn Ser Ser Lys Gln Gly Glu Gln
            965                 970                 975

Pro Cys Asn Ser Gly Ile Thr Ile Phe Glu Ile Asn Pro Val Ser Asn
            980                 985                 990

Asn Ser Lys Thr Pro Leu Thr Gln Ala Thr Glu Glu Gly His Phe Ser
            995                 1000                1005

Ala Val His Gly Glu Lys Thr Lys Ala Ser Lys Thr Lys Asp Asn
            1010                1015                1020

Arg Glu Gly Gln Glu Leu Ala Cys His Phe Ser Ala Lys Cys Tyr
            1025                1030                1035

Lys Lys Asp Lys Lys Gly Asn Phe Lys Ile Arg His Asp Thr Ser
            1040                1045                1050

Leu Lys Met Glu Gln Lys Leu Lys Asn Ile Ser Ser Lys Cys Asp
            1055                1060                1065
```

-continued

```
Ile Pro Asn Pro Ser Lys Cys Asn Lys Ile Ala Ala Pro Glu Ile
    1070            1075            1080

Leu His Val Thr Thr Ser Asn Ser Ala Lys Asn Met Pro Phe Ser
    1085            1090            1095

Lys Gln Ala Ser Gln Glu Ser Leu Gln Lys Lys His Thr Ser Gln
    1100            1105            1110

Asp Leu Gly Pro Val Lys Ala Pro Ile Glu Leu Ser Ser Asn Thr
    1115            1120            1125

Asp Pro Cys Arg Ser Asn Thr Ser Ser Val Gln Ser Val Ser Pro
    1130            1135            1140

Glu Lys Lys Lys Leu Lys Phe Lys Ala Gly Gly Ser Arg Leu Lys
    1145            1150            1155

Tyr Phe Glu Lys Arg Lys Thr Asp His Val Ile Pro Asp Val
    1160            1165            1170

Glu Ile Lys Lys Lys Tyr Glu Lys Gln Gln Asn Lys Asn
    1175            1180            1185

Ala Gly Asp Thr Leu Lys Leu Cys Ser Ile Leu Thr Glu Ser Asn
    1190            1195            1200

Glu Arg Ala Ser Val Gln Glu Lys Thr Val Pro Ser Pro Glu Ser
    1205            1210            1215

Ser Asp Pro Lys Gly Ser Ser Ser Lys Ser Thr Arg Val Ile Thr
    1220            1225            1230

Val Gln Glu Tyr Leu Gln Arg Gln Lys Asp Lys Gln Ile Thr Gly
    1235            1240            1245

Asn Asn Ala Ser Arg Asn Ile Cys Val Glu Thr Val Leu Cys Asp
    1250            1255            1260

Ser Gly His Thr Lys Thr Ser Lys His Ser Ala Ala Val Ser Trp
    1265            1270            1275

Gly Lys Leu Val Glu Gly Gln Ser Ile Ser Ala Glu Thr Ala Lys
    1280            1285            1290

Glu Leu Glu His Asn Ser Ser Ser His Gly Lys Asp Phe Lys Ile
    1295            1300            1305

His His Ser Glu Ala Ser Arg Thr His Ser Val Ser Asn Asn Asn
    1310            1315            1320

Lys Gly Lys Phe Asp Gly Lys Gln Pro Asp Lys Met Phe Lys Asn
    1325            1330            1335

Lys Thr Ser Met Asn Asn Glu Ser Asn Gln Met Pro Leu Gln Val
    1340            1345            1350

Lys Glu Gln Arg Lys Gln Tyr Leu Asn Arg Val Ala Phe Lys Cys
    1355            1360            1365

Thr Glu Arg Glu Ser Ile Cys Leu Thr Lys Leu Asp Ser Ala Ser
    1370            1375            1380

Lys Lys Leu Ser Ile Glu Lys Ser Gly Glu Tyr Thr Ser Lys
    1385            1390            1395

Thr Lys Asp Thr Asp Lys Pro Ser Met Leu Glu Phe Lys Leu Cys
    1400            1405            1410

Pro Asp Val Leu Leu Lys Asn Thr Ser Thr Val Asp Lys Gln Asp
    1415            1420            1425

Cys Pro Gly Pro Gly Pro Glu Lys Glu Gln Ala Pro Val Gln Val
    1430            1435            1440

Ser Gly Ile Lys Ser Thr Lys Glu Asp Trp Leu Lys Cys Ile Pro
    1445            1450            1455
```

-continued

```
Thr Arg Thr Lys Met Pro Glu Ser Ser Gln Arg Asp Ser Ala Asp
    1460            1465                1470

Ser Arg Leu Ser Lys Arg Ser Leu Ser Ala Asp Glu Phe Glu Ile
    1475            1480                1485

Leu Gln Asn Pro Val Lys Glu Ser Asn Ile Met Phe Arg Thr Tyr
    1490            1495                1500

Lys Lys Met Tyr Leu Glu Lys Arg Ser Arg Ser Leu Gly Ser Ser
    1505            1510                1515

Pro Val Lys
    1520

<210> SEQ ID NO 36
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 36

His His His His His His
1               5

<210> SEQ ID NO 37
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Asp Tyr Lys Asp Asp Asp Asp Lys
1               5

<210> SEQ ID NO 38
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ala Trp Arg His Pro Gln Phe Gly Gly
1               5

<210> SEQ ID NO 39
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Trp Ser His Pro Gln Phe Glu Lys
1               5
```

MAMMALIAN CELLS EXPRESSING CYTOMEGALOVIRUS ANTIGENS

FIELD OF THE INVENTION

This invention relates to host cells expressing cytomegalovirus (CMV) proteins suitable for vaccine uses.

BACKGROUND OF THE INVENTION

Cytomegalovirus is a genus of virus that belongs to the viral family known as Herpesviridae or herpesviruses. The species that infects humans is commonly known as human cytomegalovirus (HCMV) or human herpesvirus-5 (HHV-5). Within Herpesviridae, HCMV belongs to the Betaherpesvirinae subfamily, which also includes cytomegaloviruses from other mammals.

Although they may be found throughout the body, HCMV infections are frequently associated with the salivary glands. HCMV infects between 50% and 80% of adults in the United States (40% worldwide), as indicated by the presence of antibodies in much of the general population. HCMV infection is typically unnoticed in healthy people, but can be life-threatening for the immunocompromised, such as HIV-infected persons, organ transplant recipients, or new born infants. HCMV is the virus most frequently transmitted to a developing fetus. After infection, HCMV has an ability to remain latent within the body for the lifetime of the host, with occasional reactivations from latency. Given the severity and importance of this disease, obtaining an effective vaccine is considered a public health top priority (Sung, H., et al., (2010) Expert review of vaccines 9, 1303-1314; Schleiss, Expert Opin Ther Pat. April 2010; 20(4): 597-602).

The genomes of over 20 different HCMV strains have been sequenced, including those of both laboratory strains and clinical isolates. For example, the following strains of HCMV have been sequenced: Towne (GL239909366), AD169 (GI:219879600), Toledo (GL290564358) and Merlin (GI: 155573956). HCMV strains AD169, Towne and Merlin can be obtained from the American Type Culture Collection (ATCC VR538, ATCC VR977 and ATCC VR1590, respectively).

CMV contains an unknown number of membrane protein complexes. Of the approximately 30 known glycoproteins in the viral envelope, gH and gL have emerged as particularly interesting due to their presence in several different complexes: dimeric gH/gL, trimeric gH/gL/gO (also known as the gCIII complex), and the pentameric gH/gL/pUL128/pUL130/pUL131 (pUL131 is also referred to as "pUL131A", "pUL131a", or "UL131A"; pUL128, pUL130, and pUL131 subunits sometimes are also referred as UL128, UL130, UL131). CMV is thought to use the pentameric complexes to enter epithelial and endothelial cells by endocytosis and low-pH-dependent fusion but it is thought to enter fibroblasts by direct fusion at the plasma membrane in a process involving gH/gL or possibly gH/gL/gO. The gH/gL and/or gH/gL/gO complex(es) is/are sufficient for fibroblast infection, whereas the pentameric complex is required to infect endothelial and epithelial cells.

The pentameric complex is considered as a major target for CMV vaccination. Viral genes UL128, UL130 and UL131 are needed for endothelial entry (Hahn, Journal of Virology 2004; 78:10023-33). Fibroblast-adapted non-endothelial tropic strains contain mutations in at least one of these three genes. Towne strain, for example, contains a 2 base pair insertion causing a frame shift in UL130 gene, whereas AD169 contains a 1 base pair insertion in UL131 gene. Both Towne and AD169 could be adapted for growth in endothelial cells, and in both instances, the frame shift mutations in UL130 or UL131 genes were repaired.

U.S. Pat. No. 7,704,510 discloses that pUL131A is required for epithelial cell tropism. U.S. Pat. No. 7,704,510 also discloses that pUL131 and pUL130 form a complex with gH/gL, which is incorporated into virions. This complex is required to infect endothelial and epithelial cells but not fibroblasts. Anti-CD46 antibodies were found to inhibit HCMV infection of epithelial cells.

CMV vaccines tested in clinical trials include Towne vaccine, Towne-Toledo chimeras, an alpha virus replicon with gB as the antigen, gB/MF59 vaccine, a gB vaccine produced by GlaxoSmithKline, and a DNA vaccine using gB and pp65. pp65 is viral protein that is a potent inducer of CD8+ responses directed against CMV. These vaccines are all poor inducers of antibodies that block viral entry into endothelial/epithelial cells (Adler, S. P. (2013), British Medical Bulletin, 107, 57-68. doi:10.1093/bmb/Idt023).

It is generally believed that neutralizing antibodies against the pentameric complex (gH/gLpUL128/pUL130/pUL131) will be significantly more potent than neutralizing antibodies raised against CMV gB subunit, or gH/gL dimeric complex. Therefore, to develop an effective vaccine against CMV, there is an urgent need for production of large quantities (e.g., commercial scales) of CMV pentameric complex.

However, recombinant production of CMV pentameric complex remains challenging. All five subunits need to be expressed (preferably at a substantially equal amount, and preferably at a sustained period of time), fold correctly, and be properly assembled into a pentamer. In addition, there is also a need to avoid undesired assembly of contaminating complexes (such as gH/gL dimer, gH/gL tetramer (two copies of gH and two copies of gL), gH/gLpUL128/pUL130 tetramer, etc.).

Recombinant expression such a eukaryotic protein complex would require the identification of suitable constructs and suitable hosts, for the expression of sufficient amounts of properly folded proteins at a sustained period of time, which can then be properly assembled into protein complexes. Furthermore, the selection of a suitable expression host has a significant impact on protein yield and quality, as well as on actual costs of the production process.

SUMMARY OF THE INVENTION

Disclosed and exemplified herein are mammalian host cells, in particular CHO cells, in which the sequence(s) encoding CMV proteins gH, gL, pUL128, pUL130, pUL131 (or a complex-forming fragment thereof) are stably integrated into the genome. Such host cells provide a reliable source where gH/gL/pUL128/pUL130/pUL131 pentameric complex can recombinantly produced.

In one aspect, the invention provides a recombinant mammalian cell, such as a rodent cell (e.g., a CHO cell) comprising one or more polynucleotide sequences encoding cytomegalovirus (CMV) pentameric complex, wherein said pentameric complex comprises (i) gH or a complex-forming fragment thereof, (ii) gL or a complex-forming fragment thereof, (iii) pUL128 or a complex-forming fragment thereof, (iv) pUL130 or a complex-forming fragment thereof, and (v) pUL131 or a complex-forming fragment thereof, wherein said one or more polynucleotide sequences are integrated into the genomic DNA of said mammalian cell. Because the polynucleotide sequences are stably integrated into the genomic DNA of the cell, they can be transmitted to its progeny as part of the genomic sequences.

Such cells are often referred in the art as stable cell lines. Particularly, the cell does not comprise the CMV viral sequences that could result in production of infectious CMV virus. In certain embodiments, the mammalian cell is a CHO cell. When cultured in a suitable condition, said CMV pentameric complex is expressed by said host cell.

Suitable CHO cells include, e.g., any CHO cell lines available at American Type Culture Collection (ATCC) or European Collection of Cell Cultures (ECACC). Exemplary CHO cell lines include e.g., CHO-K1 cell, CHO-DUXB11, CHO-DG44, or CHO-S cells. For ease of selection of stably integrated clones, the host cells may be dihydrofolate reductase (DHFR)-deficient. Recombination protein expression in DHFR-deficient or DHFR-competent cell lines can also be screened by methotrexate (MTX) selection.

The host cell may have one or more additional modifications to further enhance the production of CMV pentameric complex. In certain embodiments, the expression level or activity of C12orf35 protein is reduced in the host cell, as compared to a control. In certain embodiments, the expression level or activity of FAM60A protein is reduced in the host cell, as compared to a control. In certain embodiments, the expression level or activity of matriptase is reduced in the host cell, as compared to a control. The modifications described herein may be used singularly or in any combination.

The recombinantly produced CMV pentameric complex may be soluble (e.g., lacking the transmembrane domain of gH). For ease of production, the recombinantly produced CMV pentameric complex may be secreted from the host cell into culturing medium.

The mammalian host cells described herein are particularly suitable for large-scale production, such as cultures that are at least 20 liters (e.g., 50 liters, 100 liters etc.) in size. In certain embodiments, the yield of CMV pentameric complex is at least 0.05 g/L, or at least 0.1 g/L.

DETAILED DESCRIPTION OF THE INVENTION

1. Overview

Figure 1:
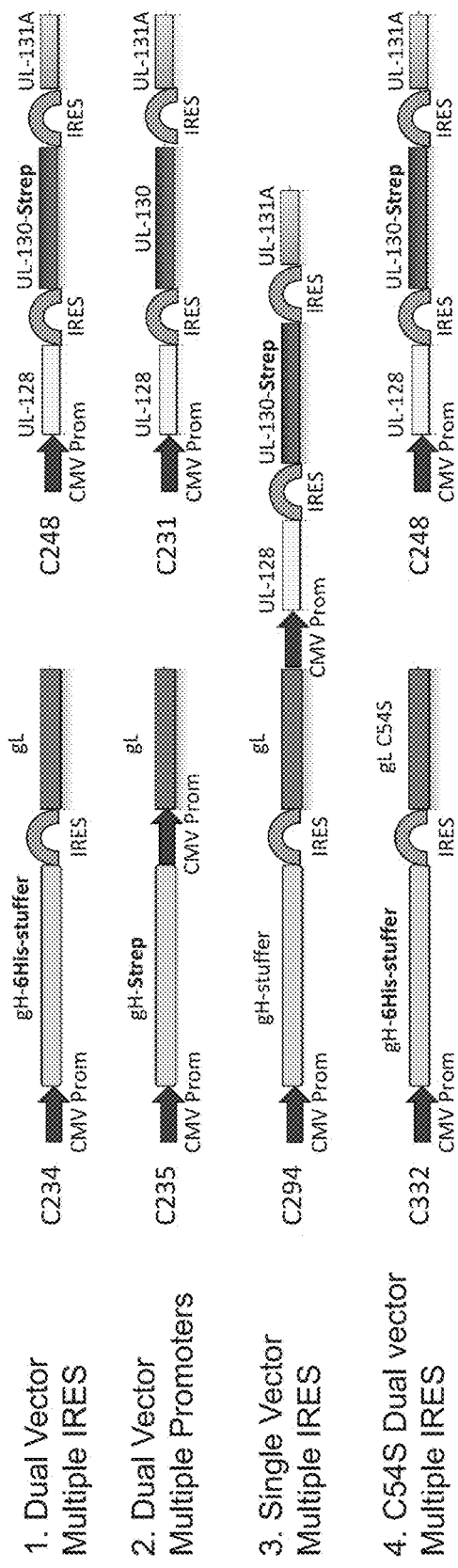
FIG. 1 illustrates various design strategies for co-expression of five components of pentamer.

One of the major targets for CMV vaccination is the pentameric complex (gH/gL/pUL128/pUL130/pUL131). To produce recombinant CMV pentamer at a commercial scale, there is a need to identify suitable constructs and suitable hosts, such that the five subunits of the pentamer can be expressed at sufficient amounts for a sustained period of time, and can be properly assembled into a pentameric complex. The CMV pentamer is a primary target of neutralizing antibodies against human CMV.

CMV pentamer have been recombinantly produced using HEK293 as host cells. See, WO2014/005959. However, HEK293 cell line is generally recognized in the art as one of the best host cell lines for transient gene expression. See, Meyer et al., PLoS One, 2013 Jul. 17; 8(7):e68674. doi: 10.1371/journal.pone.0068674. However, it would be difficult to maintain the expression of the pentamer for a sustained period of time in transiently transfected HEK293 cells. Further, in the examples disclosed in WO 2014/005959, the five subunits of the pentamer were introduced into HEK293 cells via five different plasmids. Under such configuration, it would be difficult to maintain the expression of each of the pentamer subunit at a substantially equal level. Uneven amount of the subunits may reduce the efficiency of pentamer assembly, especially given that these subunits already have a tendency to form contaminating complexes, such as gH/gL dimer, gH/gL tetramer (2 copies of gH and 2 copies of gL), gH/gLpUL128/pUL130 tetramer. Further, the plasmid encoding gH was selected by neomycin, the four plasmids encoding gL, pUL128, pUL130, and pUL131, respectively, were all selected by kanamycin. Therefore, because all four plasmids were selected by kanamycin, loss of a single plasmid in a host cell could not be easily detected, but loss of a single plasmid would prevent the assembly of pentamer.

As disclosed and exemplified herein, the inventors overcame the difficulties of recombinant production of CMV pentamer by using Chinese Hamster Ovary (CHO) cells. In these CHO cells, sequences encoding gH, gL, pUL128, pUL130, pUL131 (or a complex-forming fragment thereof) are stably integrated into the genome of the CHO cells. By integrating pentamer-coding sequences into the genome of the CHO cell, the inventors achieved stable genomic expression of recombinant pentamer, with a high efficiency and genomic stability. As exemplified in the Examples section, it was discovered that, as compared to transiently transfected HEK293 cells, the CHO stable lines consistently achieved 100 fold higher yield, making these CHO cell lines particularly suitable for commercial production of CMV pentamer. The stable integration also allows easy manipulation of large scale cell culture, in comparison to transiently transfected HEK cells with five exogenous plasmids. In fact, the top clones produced pentamer with yield as high as 0.1 g/L to 0.5 g/L.

Further improvements of host cells for CMV pentamer production are also provided herein. In particular, three modified host cells are exemplified: (i) host cells in which expression level or activity of C12orf35 protein is reduced, as compared to a control; (ii) host cells in which expression level or activity of FAM60A protein is reduced, as compared to a control; (iii) host cells in which expression level or activity of matriptase is reduced, as compared to a control. It was discovered that reduction of the expression level or activity of C12orf35 protein or FAM60A protein results in a significant increase in the expression level of a recombinant protein. It was also discovered that reduction of the expression level or activity of matriptase significantly decreases the proteolytic degradation ("clipping") of a recombinant protein. These modifications may be used singularly or in any combination.

Accordingly, provided herein are mammalian host cells, in particular CHO cells, in which the polynucleotide sequence(s) encoding CMV pentameric complex comprising gH, gL, pUL128, pUL130, pUL131 (or a complex-forming fragment thereof) are stably integrated into the genomic DNA. When cultured in a suitable condition, said CMV pentameric complex is expressed by said host cells.

Also provided herein is a cytomegalovirus (CMV) pentameric complex produced by the mammalian cells described herein.

Also provided herein is a process of producing cytomegalovirus (CMV) pentameric complex, wherein said pentameric complex comprises: gH or a complex-forming fragment thereof, gL or a complex-forming fragment thereof, pUL128 or a complex-forming fragment thereof, pUL130 or a complex-forming fragment thereof, and pUL131 or a complex-forming fragment thereof, comprising: (i) culturing the mammalian cell as described herein under a suitable condition, thereby expressing said pentameric complex; and harvesting said pentameric complex from the culture. The pentameric complex may be further comprising purified. Also provided herein is a cytomegalovirus (CMV) pentameric complex produced by this process.

Also provided herein is a composition comprising the pentameric complex described herein. The composition may comprise a purified CMV pentameric complex that is suitable for in vivo administration. For example, the pentameric complex in such a composition may have a purity of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, by mass. The composition may further comprise an adjuvant, such as an aluminum salt, or MF59.

Also provided herein is a composition for use in inducing an immune response against CMV. Use of the composition described herein for inducing an immune response against CMV, and use of the composition described herein in the manufacture of a medicament for inducing an immune response against CMV, are also provided.

2. CMV Pentameric Complexes and Coding Sequences

A. CMV Pentameric Complexes

In one aspect, the invention provides a mammalian host cell that expresses CMV pentameric complex, wherein said pentameric complex comprises (i) gH or a complex-forming fragment thereof, (ii) gL or a complex-forming fragment thereof, (iii) pUL128 or a complex-forming fragment thereof, (iv) pUL130 or a complex-forming fragment thereof, and (v) pUL131 or a complex-forming fragment thereof. The polynucleotide sequences encoding CMV pentameric complex are integrated into the genomic DNA of the host cell, and, when cultured in a suitable condition, said CMV pentameric complex is expressed by said host cell.

In certain embodiments, said pentameric complex is soluble. Soluble pentameric complex can be obtained, e.g., by using a fragment of gH in wherein the transmembrane domain of the gH subunit is deleted, as described in detail below.

In certain embodiments, said pentameric complex is secreted from the host cell. It has been reported that the presence of all five subunits, gH, gL, pUL128, pUL131, and pUL131, is sufficient for the assembly of the pentameric complex in ER before it is export to the Golgi apparatus. See, Ryckman et al., J Virol. January 2008; 82(1): 60-70. Alternatively or in addition, an appropriate signal peptide may be used in one or more of the five subunits (e.g., by making a fusion protein with a secretory signal). Signal sequences (and expression cassette) for producing secretory proteins are known in the art. In general, leader peptides are 5-30 amino acids long, and are typically present at the N-terminus of a newly synthesized protein. The core of the signal peptide generally contains a long stretch of hydrophobic amino acids that has a tendency to form a single alpha-helix. In addition, many signal peptides begin with a short positively charged stretch of amino acids, which may help to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein.

Human CMV glycoprotein H (gH), encoded by the UL75 gene, is a virion glycoprotein that is essential for infectivity and which is conserved among members of the alpha-, beta- and gamma-herpesviruses. It can form a stable complex with gL, and the formation of this complex facilitates the cell surface expression of gH. Based on the crystal structures of HSV-2 and EBV gH/gL complexes, the gL subunit and N-terminal residues of gH form a globular domain at one end of the structure (the "head"), which is implicated in interactions with gB and activation of membrane fusion. The C-terminal domain of gH, proximal to the viral membrane (the "tail"), is also implicated in membrane fusion. gH displays determinants that are recognized by the host factor TLR2, and it directly interacts with a heterodimer formed between the host factors TLR2 and TLR1. TLR2 mediates NF-κB activation and inflammatory cytokine responses from cells.

The gH from CMV strain Merlin is shown as SEQ ID NO: 1 (GI:52139248, 742 amino acid residues). The gH from CMV strain Towne is shown as SEQ ID NO: 2 (GI:138314, also 742 amino acid residues). gH from Towne has been characterized as having: (i) six N-glycosylation sites (at residues 55, 62, 67, 192, 641 and 700); (ii) a hydrophobic signal sequence at its N-terminus (amino acid residues 1-23); (iii) an ectodomain (residues 24-717) that projects out of the cell into the extracellular space; (iv) a hydrophobic transmembrane (TM) domain (residues 718-736); and (v) a C-terminal cytoplasmic domain (residues 737-742). SEQ ID NO: 2 shares 99% and 96% amino acid sequence identity with SEQ ID NO: 1, and the gH from CMV strain AD169 (GI:138313, SEQ ID NO: 3), respectively.

Typically, the N-terminal signal sequence of full-length gH protein is cleaved by a host cell signal peptidase to produce a mature gH protein. As such, the gH protein expressed by the host cell described herein may lack the N-terminal signal sequence (e.g., gH is encoded by a nucleotide sequence that lacks the coding sequence for the N-terminal signal sequence).

Also encompassed in the invention are complex-forming fragments of gH, such as a gH fragment that lacks the transmembrane (TM) domain (e.g., residues 718-736 of SEQ ID NO:2), the C-terminal domain (e.g., residues 737-742 of SEQ ID NO:2), the N-terminal signal sequence (e.g., residues 1-23 of SEQ ID NO:2), or a combination thereof. A complex-forming fragment of gH can be any part or portion of the gH protein that retain the ability to form a complex with another CMV protein. In certain embodiments, a complex-forming fragment of gH forms part of the pentameric gH/gL/pUL128/pUL130/pUL131 complex. For example, expression of the full-length gH sequence may hinder purification of soluble pentameric complex because the TM domain of gH is hydrophobic. Instead, the pentameric complex may comprise a gH fragment with at least a portion of the TM domain of gH deleted.

For example, a gH fragment comprising the N-terminal signal sequence and the ectodomain of gH, but not the TM domain, can be used. A suitable gH fragment may also comprise the a portion of the ectodomain of gH (e.g., at least about 70%, at least about 80%, at least about 85%, at least about 90%, at least about 95%, at least about 96%, at least about 97%, at least about 98%, or at least about 99% of the ectodomain sequence of gH), but none, or only a small portion of the TM domain. Alternatively, the gH fragment described herein may lack between 1 and 20 amino acid residues (e.g. 1, 2, 3, 4, 5, 6, 7, 8, 9, 10, 11, 12, 13, 14, 15, 16, 17, 18, 19 or 20 amino acid residues, or lack 1-20 residues, 1-15 residues, 1-10 residues, 2-20 residues, 2-15 residues, 2-10 residues, 5-20 residues, 5-15 residues, or 5-10 residues) at the N-terminus and/or C-terminus of the full-length ectodomain. Residues at C-terminal domains are believed to be not necessary for immunogenicity. One example of suitable gH fragment described herein is shown as SEQ ID NO: 4, which corresponds to amino acid residues 1-715 of SEQ ID NO: 1. Another example of gH fragment described herein is shown as SEQ ID NO: 5, which lacks the N-terminal signal sequence, TM domain and C-terminal domain of gH, and corresponds to amino acid residues 24-715 of SEQ ID NO: 1. Another example of gH fragment described comprises the entire N-terminal signal sequence and the ectodomain, but lacks the C-terminal domain.

The ectodomain of gH corresponds to the extracellular domain of gH. The location and length of the ectodomain of a gH (or a homologue or a variant thereof) can be predicted based on pairwise alignment of its sequence to SEQ ID NOs: 1, 2, 3, 4, or 5, for example by aligning the amino acid sequence of a gH to SEQ ID NO: 1, and identifying the sequence that aligns to residues 24-717 of SEQ ID NO: 1. Similarly, the locations of the signal sequence, the TM domain, and the C-terminal domain can be predicted by aligning the amino acid sequence of a gH to SEQ ID NOs: 1, 2, 3, 4, or 5, and identifying the sequences that align to the corresponding regions (e.g., residues 1-23 (signal sequence), 718-736 (TM) and 737-742 (C-terminal domain) of SEQ ID NO: 1, respectively). Alternatively, the location and length of the ectodomain, the signal sequence, the TM domain, and the C-terminal domain can be predicted based on computational analysis of the hydrophobicity along the length of a given gH sequence. The signal sequence and the TM domain have the highest levels of hydrophobicity and these two regions flank the ectodomain, which is less hydrophobic.

A suitable complex-forming fragment of gH can also be obtained or determined by standard assays known in the art, such as co-immunoprecipitation assay, cross-linking, or co-localization by fluorescent staining, etc. SDS-PAGE or western blot can also be used (e.g., by showing all five subunits are present in a gel electrophoresis). In certain embodiments, the complex-forming fragment of gH (i) forms part of the pentameric gH/gL/pUL128/pUL130/pUL131 complex; (ii) comprises at least one epitope from SEQ ID NO: 1, SEQ ID NO: 2, SEQ ID NO: 3, SEQ ID NO: 4, or SEQ ID NO: 5; and/or (iii) can elicit antibodies in vivo which immunologically cross react with a CMV virion.

Other suitable gH proteins can be gH variants that have various degrees of identity to SEQ ID NOs: 1, 2, 3, 4, or 5, such as at least 60%, 70%, 80%, 85%, 90%, 91%, 92%, 93%, 94%, 95%, 96%, 97%, 98% or 99% identical to the sequence recited in SEQ ID NO: 1, SEQ ID NO: 2, SEQ ID NO: 3, SEQ ID NO: 4, or SEQ ID NO: 5. In certain embodiments, the gH variant proteins: (i) form part of the pentameric gH/gL/pUL128/pUL130/pUL131 complex; (ii) comprise at least one epitope from SEQ ID NO: 1, SEQ ID NO: 2, SEQ ID NO: 3, SEQ ID NO: 4, or SEQ ID NO: 5; and/or (iii) can elicit antibodies in vivo which immunologically cross react with a CMV virion.

Human CMV glycoprotein L (gL) is encoded by the UL115 gene. gL is thought to be essential for viral replication and all known functional properties of gL are directly associated with its dimerization with gH. The gL/gH complex is required for the fusion of viral and plasma membranes leading to virus entry into the host cell. gL from CMV strain Merlin (GI:39842115, SEQ ID NO: 6) and CMV strain Towne (GI:239909463, SEQ ID NO: 7) have been reported to be 278 amino acids in length. gL from HCMV strain AD169 (GI:2506510, SEQ ID NO: 8) has been reported to be 278 amino acids in length, with a signal sequence at its N-terminus (amino acid residues 1-35), two N-glycosylation sites (at residues 74 and 114), and lacking a TM domain. The N-terminal signal sequence in SEQ ID NO: 6 is predicted to comprise amino acid residues 1-30. SEQ ID NO: 7 shares 98% amino acid sequence identity with SEQ ID NO: 6. Sequencing of the full-length gL gene from 22 to 39 clinical isolates, as well as laboratory strains AD169, Towne and Toledo revealed less than 2% variation in the amino acid sequences among the isolates.

Typically, the N-terminal signal sequence of full-length gL protein is cleaved by a host cell signal peptidase to produce a mature gL protein. As such, the gL protein expressed by the host cell described herein may lack the N-terminal signal sequence (e.g., gL is encoded by a nucleotide sequence that lacks the coding sequence for the N-terminal signal sequence). An example of a gL lacking signal sequence is SEQ ID NO: 9, which comprises amino acid residues 31-278 of SEQ ID NO: 6, and lacks an N-terminal signal sequence of SEQ ID NO: 6. Signal sequence of other gL proteins can be determined by sequence alignment or sequence analysis tools as described above.

Also encompassed in the invention are complex-forming fragments of gL. A complex-forming fragment of gL can be any part or portion of the gL protein that retain the ability to form a complex with another CMV protein. In certain embodiments, a complex-forming fragment of gL forms part of the pentameric gH/gL/pUL128/pUL130/pUL131 complex.

A suitable complex-forming fragment of gL can be obtained or determined by standard assays known in the art, such as co-immunoprecipitation assay, cross-linking, or co-localization by fluorescent staining, etc. SDS-PAGE or western blot can also be used (e.g., by showing all five subunits are present in a gel electrophoresis). In certain embodiments, the complex-forming fragment of gL (i) forms part of the pentameric gH/gL/pUL128/pUL130/pUL131 complex; (ii) comprises at least one epitope from SEQ ID NO: 6, SEQ ID NO: 7, SEQ ID NO: 8, or SEQ ID NO: 9; and/or (iii) can elicit antibodies in vivo which immunologically cross react with a CMV virion.

Other suitable gL proteins can be gL variants (and fragments of variants) that have various degrees of identity to SEQ ID NOs: 6, 7, 8, or 9, such as at least 60%, 70%, 80%, 85%, 90%, 91%, 92%, 93%, 94%, 95%, 96%, 97%, 98% or 99% identical to the sequence recited in SEQ ID NO: 6, SEQ ID NO: 7, SEQ ID NO: 8, or SEQ ID NO: 9. In certain embodiments, the gL variant proteins: (i) form part of the pentameric gH/gL/pUL128/pUL130/pUL131 complex; (ii) comprise at least one epitope from SEQ ID NO: 6, SEQ ID NO: 7, SEQ ID NO: 8, or SEQ ID NO: 9; and/or (iii) can elicit antibodies in vivo which immunologically cross react with a CMV virion.

The pUL128 from human CMV strain Merlin has been reported (GI:39842124, SEQ ID NO: 10) to have 130 amino acid residues, and with a 1 nucleotide substitution causing premature termination. The pUL128 from human CMV strains Towne (GI:39841882, SEQ ID NO: 11) and AD169 (GI:59803078, SEQ ID NO: 12) have been reported to have 171 amino acid residues. SEQ ID NOs: 10 and 12 share over 99% sequence identity over the full-length of SEQ ID NO:

10; however, due to the premature termination of translation SEQ ID NO: 10 does not have the C-terminal 41 amino acid residues of SEQ ID NO: 12 (about 75% sequence identity over the full-length of SEQ ID NO: 12).

pUL128 is predicted to have an N-terminal signal sequence, which is located at residues 1-27 of SEQ ID NO: 10, but it is predicted to lack a TM domain. N-terminal signal sequence of full-length pUL128 protein can be cleaved by a host cell signal peptidase to produce a mature pUL128 protein. As such, the pUL128 protein expressed by the host cell described herein may lack the N-terminal signal sequence (e.g., pUL128 is encoded by a nucleotide sequence that lacks the coding sequence for the N-terminal signal sequence). An example of a mature pUL128 protein is SEQ ID NO: 13, which lacks an N-terminal signal sequence and corresponds to amino acid residues 28-171 of SEQ ID NO: 11. SEQ ID NO: 13 also matches to amino acid residues 28-171 of SEQ ID NO: 12.

Also encompassed in the invention are complex-forming fragments of pUL128. A complex-forming fragment of pUL128 can be any part or portion of the pUL128 protein that retains the ability to form a complex with another CMV protein. In certain embodiments, a complex-forming fragment of pUL128 forms part of the pentameric gH/gL/pUL128/pUL130/pUL131 complex.

A suitable complex-forming fragment of pUL128 can be obtained or determined by standard assays known in the art, such as co-immunoprecipitation assay, cross-linking, or co-localization by fluorescent staining, etc. SDS-PAGE or western blot can also be used (e.g., by showing all five subunits are present in a gel electrophoresis). In certain embodiments, the complex-forming fragment of pUL128 (i) forms part of the pentameric gH/gL/pUL128/pUL130/pUL131 complex; (ii) comprises at least one epitope from SEQ ID NO: 10, SEQ ID NO: 11, SEQ ID NO: 12, or SEQ ID NO: 13; and/or (iii) can elicit antibodies in vivo which immunologically cross react with a CMV virion.

Other suitable pUL128 proteins can be pUL128 variants (and fragments of variants) that have various degrees of identity to SEQ ID NOs: 10, 11, 12, or 13, such as at least 60%, 70%, 80%, 85%, 90%, 91%, 92%, 93%, 94%, 95%, 96%, 97%, 98% or 99% identical to the sequence recited in SEQ ID NO: 10, SEQ ID NO: 11, SEQ ID NO: 12, or SEQ ID NO: 13. In certain embodiments, the pUL128 variant proteins: (i) form part of the pentameric gH/gL/pUL128/pUL130/pUL131 complex; (ii) comprise at least one epitope from SEQ ID NO: 10, SEQ ID NO: 11, SEQ ID NO: 12, or SEQ ID NO: 13; and/or (iii) can elicit antibodies in vivo which immunologically cross react with a CMV virion.

UL130 is the central and the largest (214 codons) gene of the UL131A-128 locus. Conceptual translation of the gene predicts a long (25 amino acids) N-terminal signal sequence that precedes a hydrophilic protein, with two potential N-linked glycosylation sites (Asn85 and Asn118) within a putative chemokine domain (amino acids 46 to 120), and an additional N-glycosylation site (Asn201) close to the end of a unique C-terminal region. pUL130 is predicted to lack a TM domain. It has been reported to be a luminal glycoprotein that is inefficiently secreted from infected cells but is incorporated into the virion envelope as a Golgi-matured form. The sequences of pUL130 from human CMV strain Merlin and Towne are publicly available (GI:39842125, SEQ ID NO: 14, 214 amino acid residues; and GI:239909473, SEQ ID NO: 15, 229 amino acid residues, respectively). SEQ ID NO: 15 has been reported to contain a frameshift mutation in the C-terminal region of pUL130, and it shares 94% identity to the HCMV SEQ ID NO: 14 over the full-length of SEQ ID NO: 14.

The N-terminal signal sequence of full-length pUL130 protein can be cleaved by a host cell signal peptidase to produce a mature pUL130 protein. As such, the pUL130 protein expressed by the host cell described herein may lack the N-terminal signal sequence (e.g., pUL130 is encoded by a nucleotide sequence that lacks the coding sequence for the N-terminal signal sequence). An example of a mature pUL130 protein is SEQ ID NO: 16, which lacks an N-terminal signal sequence, and corresponds to amino acid residues 26-214 of SEQ ID NO: 14.

Also encompassed in the invention are complex-forming fragments of pUL130. A complex-forming fragment of pUL130 can be any part or portion of the pUL130 protein that retains the ability to form a complex with another CMV protein. In certain embodiments, a complex-forming fragment of pUL130 forms part of the pentameric gH/gL/pUL128/pUL130/pUL131 complex.

A suitable complex-forming fragment of pUL30 can be obtained or determined by standard assays known in the art, such as co-immunoprecipitation assay, cross-linking, or co-localization by fluorescent staining, etc. SDS-PAGE or western blot can also be used (e.g., by showing all five subunits are present in a gel electrophoresis). In certain embodiments, the complex-forming fragment of pUL130 (i) forms part of the pentameric gH/gL/pUL128/pUL130/pUL131 complex; (ii) comprises at least one epitope from SEQ ID NO: 14, SEQ ID NO: 15, or SEQ ID NO: 16; and/or (iii) can elicit antibodies in vivo which immunologically cross react with a CMV virion.

Other suitable pUL130 proteins can be pUL130 variants (and fragments of variants) that have various degrees of identity to SEQ ID NOs: 14, 15, or 16, such as at least 60%, 70%, 80%, 85%, 90%, 91%, 92%, 93%, 94%, 95%, 96%, 97%, 98% or 99% identical to the sequence recited in SEQ ID NO: 14, SEQ ID NO: 15, or SEQ ID NO: 16. In certain embodiments, the pUL130 variant proteins: (i) form part of the pentameric gH/gL/pUL128/pUL130/pUL131 complex; (ii) comprise at least one epitope from SEQ ID NO: 14, SEQ ID NO: 15, or SEQ ID NO: 16; and/or (iii) can elicit antibodies in vivo which immunologically cross react with a CMV virion.

pUL131A function is required for human CMV replication not only in endothelial cells but also in epithelial cells. pUL131A from human CMV strains Merlin (GI:39842126, SEQ ID NO: 17, 129 amino acids) and Towne (GI: 239909474, SEQ ID NO: 18, 129 amino acids) and AD169 (GI:219879712, SEQ ID NO: 19, 76 amino acids) have been reported. pUL131A is predicted to contain an N-terminal signal sequence, which is located at residues 1-18 of SEQ ID NO: 18, and to lack a TM domain. pUL131A from strain AD169 has been reported to contain a 1-base-pair insertion, which causes a frame-shift. SEQ ID NO: 17 is 96% identical to SEQ ID NO: 19 over the N-terminal 28 amino acids, but it is only 36% identical to SEQ ID NO: 19 over the full-length of SEQ ID NO: 17, due to the frame-shift in the AD169 UL131A gene.

The N-terminal signal sequence of full-length pUL131 protein can be cleaved by a host cell signal peptidase to produce a mature pUL131 protein. As such, the pUL131 protein expressed by the host cell described herein may lack the N-terminal signal sequence (e.g., pUL131 is encoded by a nucleotide sequence that lacks the coding sequence for the N-terminal signal sequence). An example of a mature pUL130 protein is SEQ ID NO: 20, which lacks an N-terminal signal sequence and corresponds to amino acid residues 19-129 of SEQ ID NO: 17. SEQ ID NO: 35 also corresponds to amino acid residues 19-129 of SEQ ID NO: 18.

Also encompassed in the invention are complex-forming fragments of pUL131. A complex-forming fragment of pUL131 can be any part or portion of the pUL131 protein that retains the ability to form a complex with another CMV protein. In certain embodiments, a complex-forming fragment of pUL131 forms part of the pentameric gH/gL/pUL128/pUL130/pUL131 complex.

A suitable complex-forming fragment of pUL31 can be obtained or determined by standard assays known in the art, such as co-immunoprecipitation assay, cross-linking, or co-localization by fluorescent staining, etc. SDS-PAGE or western blot can also be used (e.g., by showing all five subunits are present in a gel electrophoresis). In certain embodiments, the complex-forming fragment of pUL131 (i) forms part of the pentameric gH/gL/pUL128/pUL130/pUL131 complex; (ii) comprises at least one epitope from SEQ ID NO: 17, SEQ ID NO: 18, SEQ ID NO: 19, or SEQ ID NO: 20; and/or (iii) can elicit antibodies in vivo which immunologically cross react with a CMV virion.

Other suitable pUL131 proteins can be pUL131 variants (and fragments of variants) that have various degrees of identity to SEQ ID NOs: 17, 18, 19, or 20, such as at least 60%, 70%, 80%, 85%, 90%, 91%, 92%, 93%, 94%, 95%, 96%, 97%, 98% or 99% identical to the sequence recited in SEQ ID NO: 17, SEQ ID NO: 18, SEQ ID NO: 19, or SEQ ID NO: 20. In certain embodiments, the pUL131 variant proteins: (i) form part of the pentameric gH/gL/pUL128/pUL130/pUL131 complex; (ii) comprise at least one epitope from SEQ ID NO: 17, SEQ ID NO: 18, SEQ ID NO: 19, or SEQ ID NO: 20; and/or (iii) can elicit antibodies in vivo which immunologically cross react with a CMV virion.

In certain embodiments, the gH, gL, pUL128, pUL130, pUL131 (or a fragment thereof) described herein may contain additional amino acid residues, such as N-terminal or C-terminal extensions. Such extensions may include one or more tags, which can facilitate detection (e.g. an epitope tag for detection by monoclonal antibodies) and/or purification (e.g. a polyhistidine-tag to allow purification on a nickel-chelating resin) of the proteins. Examples of affinity-purification tags include, e.g., His tag (hexahistidine (SEQ ID NO: 36), binds to metal ion), maltose-binding protein (MBP) (binds to amylose), glutathione-S-transferase (GST) (binds to glutathione), FLAG tag (Asp-Tyr-Lys-Asp-Asp-Asp-Asp-Lys (SEQ ID NO: 37), binds to an anti-flag antibody), Strep tag (Ala-Trp-Arg-His-Pro-Gln-Phe-Gly-Gly (SEQ ID NO: 38), or Trp-Ser-His-Pro-Gln-Phe-Glu-Lys (SEQ ID NO: 39), bind to streptavidin or a derivative thereof).

In a certain embodiment, cleavable linkers may be used. This allows for the tag to be separated from the purified complex, for example by the addition of an agent capable of cleaving the linker. A number of different cleavable linkers are known to those of skill in the art. Such linkers may be cleaved for example, by irradiation of a photolabile bond or acid-catalyzed hydrolysis. There are also polypeptide linkers which incorporate a protease recognition site and which can be cleaved by the addition of a suitable protease enzyme.

In other embodiments, it may be more desirable to have gH, gL, pUL128, pUL130, pUL131 (or a fragment thereof) proteins that do not comprises an exogenous tag sequence, for example, for clinical safety or efficacy reasons.

Although gH, gL, pUL130 proteins are sometimes referred to as glycoproteins, this nomenclature should not be taken to mean that these proteins must be glycosylated when used with the invention. Whilst specific strains have been referred to above, it should be understood that CMV proteins gH, gL, pUL128, pUL130, pUL131 (or fragments thereof) from different CMV strains may be used. By way of non-limiting example, other CMV strain may include Towne, Toledo, AD169, Merlin, TB20, and VR1814 strains.

B. Nucleic Acid Encoding CMV Proteins and Complexes

Also provided herein are nucleic acids encoding the CMV proteins and complexes for genomic integration, and subsequent expression of CMV pentamer.

One or more nucleic acid constructs encoding the CMV proteins and complexes described herein can be used for genomic integration. For example, a single nucleic acid construct encoding all five subunits, gH, gL, pUL128, pUL130, pUL131 (or fragments thereof), can be introduced to a host cell. Alternatively, the coding sequences for the five subunits (or fragments thereof) can be carried by two or more nucleic acid constructs, which are then introduced into host cell simultaneously or sequentially.

For example, in one exemplary embodiment the invention provides a single nucleic acid construct encoding: the ectodomain of gH, gL, pUL128, pUL130, and pUL131. In another exemplary embodiment, the invention provides two nucleic acid constructs encoding: the ectodomain of gH, gL, pUL128, pUL130, and pUL131. See, FIG. 1. In both examples, successful genomic integration was achieved.

The nucleic acid construct may comprise genomic DNA that comprises one or more introns, or cDNA. Some genes are expressed more efficiently when introns are present. Native genomic sequence encoding pUL128 comprises two introns, native genomic sequence encoding pUL131 comprises one exons, whereas the native genomic sequence encoding pUL130 does not comprise any introns. Native genomic sequence encoding pUL128 comprises three exons, native genomic sequence encoding pUL131 comprises two exons, and native genomic sequence encoding pUL130 comprises one exon. Particularly the nucleic acid sequence is suitable for the expression of exogenous polypeptides in said mammalian cell.

Also provided herein are vectors that comprise coding sequences for gH, gL, pUL128, pUL130, and/or pUL131 (or a fragment thereof). Exemplary vectors include plasmids that are able to replicate autonomously or to be replicated in a mammalian cell. Typical expression vectors contain suitable promoters, enhancers, and terminators that are useful for regulation of the expression of the coding sequence(s) in the expression construct. The vectors may also comprise selection markers to provide a phenotypic trait for selection of transformed host cells (such as conferring resistance to antibiotics such as ampicillin or neomycin).

Suitable promoters include, e.g., CMV promoter, adenovirus, EF1α, GAPDH metallothionine promoter, SV-40 early promoter, SV-40 later promoter, murine mammary tumor virus promoter, Rous sarcoma virus promoter, polyhedrin promoter, etc. Promoters can be constitutive or inducible. One or more vectors may be used (e.g., one vector encoding all five subunits or fragments thereof, or two or more vectors together encoding the five subunits or fragments thereof); see, e.g., FIG. 1.

When the host cell is a CHO cell, the promoter, enhancer, or terminator is active in CHO cells. One frequently used promoter is the promoter for human cytomegalovirus (hCMV) immediate early (IE) gene. The promoter of this gene directs high levels of transgene expression in a wide variety of cell types. The activity of this promoter depends on a series of 17, 18, 19, and 21 bp imperfect repeats, some of which bind transcription factors of the NF-κB cAMP responsive binding protein (CREB) and the nuclear factor-1 families.

A strong promoter is one which causes mRNAs to be initiated at high frequency equal to or higher than that of hCMV core promoter/enhancer fragment (described in U.S. Pat. No. 5,168,062) in a CHO cell. Such promoter may be a cell-type dependent strong promoter, as are described in U.S. Pat. No. 5,589,392, or a ubiquitously active strong promoter. Exemplary constitutively active viral promoters include, e.g., early and late promoters of the SV40 virus, the immediate early promoter of the human cytomegalovirus (hCMV) or of murine cytomegalovirus (mCMV), the thymidine kinase promoter (TK) of Herpes Simplex virus, or the Rous Sarcoma Virus long terminal repeat promoter (RS-LTR). Other examples include, e.g., hCMV-MIE promoter as defined by the 2.1 kb Pst I fragment described in U.S. Pat. No. 5,385,839 and/or EP-323 997-A1 or a functional part thereof having promoter activity.

Internal ribosome entry site (IRES) and 2A peptide sequences may also be used. IRES and 2A peptide provides alternative approaches for co-expression of multiple sequences. IRES is a nucleotide sequence that allows for translation initiation in the middle of a messenger RNA (mRNA) sequence as part of the greater process of protein synthesis. Usually, in eukaryotes, translation can be initiated only at the 5' end of the mRNA molecule. IRES elements allow expression of multiple genes in one transcript. IRES-based polycistronic vectors, which express multiple proteins from one transcript, can reduce the escape of non-expressing clones from selection.

The 2A peptide allows translation of multiple proteins in a single open reading frame into a polyprotein that is subsequently cleaved into individual proteins through a ribosome-skipping mechanism. 2A peptide can provide more balanced expression of multiple protein products.

Exemplary IRES sequences include, e.g., EV71 IRES, EMCV IRES, HCV IRES.

For genomic integration, the integration can be site-specific or random. Site-specific recombination can be achieved by introducing homologous sequence(s) into the nucleic acid constructs described herein. Such homologous sequence substantially matches the endogenous sequence at a specific target site in the host genome. Alternatively, random integration may be used. Sometimes, the expression level of a protein may vary depending upon the integration site. Therefore, it may be desirable to select a number of clones according to recombinant protein expression level to identify a clone that achieves the desired level of expression.

3. Host Cells

In another aspect, the invention provides host cells in which the pentamer-coding sequences are stably integrated into the genome of the host cells, and, when cultured under a suitable condition, express the CMV pentamer as disclosed herein. In certain embodiments, the host cell is a mammalian cell. In certain embodiment, the host cell is a rodent cell.

Examples of rodent cell lines include e.g., baby hamster kidney (BHK) (e.g., BHK21, BH TK), mouse Sertoli (TM4), buffalo rat liver (BRL 3A), mouse mammary tumor (MMT), rat hepatoma (HTC), mouse myeloma (NS0), murine hybridoma (Sp2/0), mouse thymoma (EL4), Chinese Hamster Ovary (CHO) and CHO cell derivatives, murine embryonic (NIH/3T3, 3T3 Li), rat myocardial (H9c2), mouse myoblast (C2C12), and mouse kidney (miMCD-3).

In one embodiment, the rodent cell is a CHO cell. Suitable CHO cells include, e.g., DUXB11 and DG44 lines. These two cell lines are deficient in dihydrofolate reductase (DHFR) activity, and hence dependent upon an exogenous source of nucleotide precursors for growth. The DHFR deficiency is a readily manipulated phenotype suitable to select for genome integration and stable expression of exogenous DNA. Genomic integration is accomplished by transfecting the cells with expression cassettes for the gene of interest and a DHFR gene. Post-transfection, cells are placed in selection media lacking nucleotide precursors.

Recombination protein expression in DHFR-deficient cell lines can be further enhanced by adding methotrexate (MTX) to the cultures, such that a high copy number of the introduced expression vector can be selected. MTX is a competitive inhibitor of the DHFR enzyme. Applying this additional selection pressure on top of the absence of nucleotide precursors enables the selection and isolation of the minor population of cells that have undergone a spontaneous amplification of the integrated expression vector containing the DHFR selectable marker and, in most cases, the gene of interest. The presence of multiple gene copies helps to achieve high level of expression of exogenous proteins. Alternatively, MTX selection can be carried out independent of DHFR-deficiency (i.e., use MTX to select a host cell that is originally DHFR-competent), as exemplified in the Examples disclosed herein.

Another suitable CHO cell line is the wild-type CHO-K1 cell line, and its derivative CHO-K1SV.

One commonly used selection method for CHO-K1 cell lines are glutamine synthetase (GS) selection. Absent an exogenous source of glutamine, cell survival is dependent on the GS enzyme to produce glutamine. With host cell lines such as murine myeloma-derived NS/0 cells and CHO cells, which have relatively low endogenous GS enzymatic activity, the method allows a simple selection scheme when using a GS selectable marker in the expression vector and glutamine-free selection media. Similar to the DHFR/MTX system, the GS competitive inhibitor methionine sulphoximine (MSX) can be added to the media to apply additional pressure and select for CHO cells that are driving high levels of expression from the integrated vector.

CHO-K1 cells, or any other commonly used CHO cells, can also be selected based on DHFR-deficiency as described above. For example, a CHO-K1 cell, or any other type of CHO cell, can have DHFR-deficiency, such as a deletion wherein at least one copy of the genomic sequence of the dihydrofolate reductase (DHFR) gene, or at least 30% (e.g., at least 40%, at least 50%, at least 60%, at least 70%, at least 80%, at least 90%, or 100%) of coding sequence of said DHFR gene, is deleted. Other ways to introduce DHFR-deficiency include creating mutations in the endogenous DHFR gene. The cell lines can be further enhanced by adding methotrexate (MTX) to the cultures as described above.

CHO-K1 cells, or any other commonly used CHO cells, can also be selected based on MTX, with or without DHFR-deficiency. In the examples provided herein, the CHO cells were selected based on MTX, without DHFR deficiency (i.e., the original CHO cell used for genomic integration is DHFR-competent). In such a system, typically, the number of copies of exogenous sequences (e.g., the sequences encoding CMV proteins) is generally low. It is estimated that the cell lines in the Examples described herein have about 1-10 copies of exogenous sequences encoding the CMV proteins, at a very limited number of integration sites (e.g., 1-2 integration sites). In general, when a DFHR-deficient cell line is used, the number of copies of exogenous sequences is typically much higher, sometimes as high as a few hundred copies. Both methods are expected to be suitable for producing CHO cell lines disclosed herein, although when the copy number is high, the host cell may lose one or more copies of exogenous sequences during the passaging and/or expansion of the cell line.

Other CHO cell strains suitable for the invention described herein include, e.g., CHO-ICAM-1 cells, and CHO-hIFNγ cells. These genetically modified cells permit stable insertion of recombinant DNA into a specific gene or expression region of the cells, amplification of the inserted DNA, and selection of cells exhibiting high level expression of the recombinant protein.

Exemplary CHO cell lines available at European Collection of Cell Cultures (ECACC) are listed in Table 1. Any CHO cells listed in Table 1 may be used.

Other commercially available CHO cell lines include, e.g., FreeStyle™ CHO-S Cells and Flp-In™-CHO Cell Line from Life Technologies.

Methods for expressing recombinant proteins in CHO cells in general have been disclosed. See, e.g., in U.S. Pat. Nos. 4,816,567 and 5,981,214.

In addition to CHO cells, other mammalian cells may also be used as hosts. Exemplary rodent cells include BHK21 cells, NS0 cells, Sp2/0 cells, EL4 cells, NIH/3T3 cells, 3T3-L1 cells, ES-D3 cells, H9c2 cells, C2C12 cells, YB2/0, mimcd 3 cells, etc. Exemplary human cells include: SH-SY5Y cells, IM 32 cells, LAN cells, MCFIOA cells, 293T cells, SK-BR3 cells, huvec cells, huasmc cells, HKB-1 cells, hmsc cells, U293 cells, HE 293 cells, PERC6® cells, Jurkai cells, HT-29 cells, Incap.FGC cells, A549 cell, MDA MB453 cells, hepg2 cells, THP-1 cells, bxpc-3 cells, Capan-1 cells, DU145 cells, and PC-3 cells.

TABLE 1

| Cell Line Name | Keywords |
| --- | --- |
| CHO | Hamster Chinese ovary |
| CHO (PROTEIN FREE) | Hamster Chinese ovary |
| CHO-CHRM1 | Human cholinergic receptor muscarinic M1, CHRM1, G Protein Coupled Receptor, GPCR, Transfected, InSCREENeX SCREENflexTM, CHO-K1 Host. |
| CHO-CHRM2 | Human cholinergic receptor muscarinic M2, CHRM2, G Protein Coupled Receptor, GPCR, Transfected, InSCREENeX SCREENflexTM, CHO-K1 Host. |
| CHO-CHRM5 | Human cholinergic receptor muscarinic M5, CHRM5, G Protein Coupled Receptor, GPCR, Transfected, InSCREENeX SCREENflexTM, CHO-K1 Host. |
| CHO-CNR1 | Human cannabinoid receptor I, CNR1 Gene ID 1268, G Protein Coupled Receptor, GPCR, Transfected, InSCREENeX SCREENflexTM, CHO-K1 Host. |
| CHO-FFAR2 | Human free fatty acid receptor 2, FFAR2, G Protein Coupled Receptor, GPCR, Transfected, InSCREENeX SCREENflexTM, CHO-K1 Host. |
| CHO-GPR120 | Human receptor GPR120 (orphan), GPR120, G Protein Coupled Receptor, GPCR, Transfected, InSCREENeX SCREENflexTM, CHO-K1 Host. |
| CHO-K1 | Hamster Chinese ovary |
| CHO-K1-AC-free | Hamster Chinese Ovary, serum-free |
| CHO-K1/SF | Hamster Chinese ovary (MEM adapted) |
| CHO-NPY1R | Human neuropeptide Y receptor, NPY1R, Gene ID 4886, G Protein Coupled Receptor, GPCR, Transfected, InSCREENeX SCREENflexTM, CHO-K1 Host. |
| CHO-OPRL1 | Human opiate receptor-like 1, OPRL1, G Protein Coupled Receptor, GPCR, Transfected, InSCREENeX SCREENflexTM, CHO-K1 Host. |
| CHO-SSTR1 | Human Somatostatin Receptor 1, SSTR1 G Protein Coupled Receptor, GPCR, Transfected, InSCREENeX SCREENflexTM, CHO-K1 Host. |
| CHO/dhFr- | Hamster Chinese ovary |
| CHO/dhFr-AC-free | Hamster Chinese Ovary, serum-free |
| RR-CHOKI | Hamster Chinese ovary |
| T02J-10/10 (CHO-GCGR (GCGR)) | Human glucagon receptor, GCGR, G Protein Coupled Receptor, GPCR, Transfected, InSCREENeX SCREENflex ™, CHO-K1 Host. |

Various CHO cell lines are also available from American Type Culture Collection (ATCC), such as CHO cell lines hCBE11 (ATCC® PTA-3357™), E77.4 (ATCC® PTA-3765™), hLT-B: R-hG1 CHO #14 (ATCC® CRL-11965™), MOR-CHO-MORAb-003-RCB (ATCC® PTA-7552™), AQ.C2 clone 11B (ATCC® PTA-3274™), AQ.C2 clone 11B (ATCC® PTA-3274™), hsAQC2 in CHO-DG44 (ATCC® PTA-3356™), xrs5 (ATCC® CRL-2348™), CHO-K1 (ATCC® CCL-61™), Lec1 [originally named Pro-5WgaRI3C] (ATCC® CRL-1735™), Pro-5 (ATCC® CRL-1781™), ACY1-E (ATCC® 65421™), ACY1-E (ATCC® 65420™), pgsE-606 (ATCC® CRL-2246™), CHO-CD36 (ATCC® CRL-2092™), pgsC-605 (ATCC® CRL-2245™), MC2/3 (ATCC® CRL-2143™), CHO-ICAM-1 (ATCC® CRL-2093™), and pgsB-618 (ATCC® CRL-2241™). Any one of these CHO cell lines may be used.

For example, cell line PERC6®, mouse myeloma NS0 cell, baby hamster kidney (BHK) cell, and the human embryonic kidney cell line (HEK293) received regulatory approval for recombinant protein production.

Examples of non-human primate cell lines useful in methods provided herein include the cell lines monkey kidney (CVI-76), African green monkey kidney (VERO-76), green monkey fibroblast (COS-1), and monkey kidney (CVI) cells transformed by SV40 (COS-7). Additional mammalian cell lines are known to those of ordinary skill in the art and are catalogued at the American Type Culture Collection catalog (Manassas, Va.).

In some embodiments, the host cells are suitable for growth in suspension cultures. Suspension-competent host cells are generally monodisperse or grow in loose aggregates without substantial aggregation. Suspension-competent host cells include cells that are suitable for suspension culture without adaptation or manipulation (e.g., hematopoietic cells, lymphoid cells) and cells that have been made suspension-competent by modification or adaptation of attachment-dependent cells (e.g., epithelial cells, fibroblasts).

In some embodiments, the host cell is an attachment dependent cell which is grown and maintained in adherent culture. Examples of human adherent cell lines useful in methods provided herein include the cell lines human neuroblastoma (SH-SY5 Y, IMR32, and LANS), human cervical carcinoma (HeLa), human breast epithelial (MCFIOA), human embryonic kidney (293T), and human breast carcinoma (SK-BR3).

C12orf35 Genes and C12orf35 Proteins

In certain embodiments, the host cell is a cell in which the expression level or activity of C12orf35 protein is reduced, as compared to a control. In certain embodiment, such cell is a CHO cell. U.S. Provisional Patent Application No. 61/919,313, filed Dec. 20, 2013, and incorporated herein by reference, provides a detailed description of mammalian cells wherein the expression level or activity of C12orf35 protein is reduced as compared to a control.

A variety of controls may be used. Expression level or activity of the C12orf35 protein from a corresponding wild type cell can be used as a control. Alternatively, a control may be a pre-determined level or a threshold level that can be identified in literature or database.

Human C12orf35 gene refers to the nucleotide sequence encoding chromosome 12 open reading frame 35. The encoded C12orf35 protein is uncharacterized. *Cricetulus griseus* (Chinese hamster) homolog of human C12orf35 gene, named Kiaa1551, is believed be located in chromosome 8. *Mus musculus* homolog of human C12orf35 gene is believed be located in chromosome 6. The gene ID for CHO C12orf35 gene is published as GenBank gene ID No. 100762086; and for human C12orf35 gene is published as GenBank gene ID No. 55196. Information about C12orf35 gene in *Cricetulus griseus*, the coding sequence and the predicted C12orf35 protein is also available at GenBank by accession number NCBI: XM_003512865.

The C12orf35 gene is endogenously expressed in eukaryotic cells such as e.g. mammalian species such as human, mouse and hamster. The predicted protein encoded by the C12orf35 gene is a large protein exceeding 1500 residues. The sequence listing shows exemplary amino acid sequences or putative amino acid sequences of the protein encoded by the endogenous C12orf35 gene of different mammalian species such as hamster (SEQ ID NO: 21 and 22), human (SEQ ID NO: 23 and 24), and mouse (SEQ ID NO: 35). The CDS (Coding DNA Sequence) of C12orf35 from Chinese hamster is shown as SEQ ID NO: 25. Furthermore, a section of the 5'UTR (see SEQ ID NO: 26) and of the 3'UTR (see SEQ ID NO: 27) of the C12orf35 mRNA from Chinese hamster was sequenced.

In human, C12orf35 gene is also referred to as KIAA1551. Gene C12orf35 is also referred to as C12orf35like or C12orf35 homolog in hamster or 2810474O19Rik in mouse. Different names can be assigned in different species for the protein or the gene and non-limiting alternative names (aliases) are also listed above in Table 2. For simplicity, in this disclosure, homologs and orthologs from different species are all referred to as "C12orf35 gene" or "C12orf35 protein."

Against this scientific background, it is surprising and unexpected that when the expression level or activity of C12orf35 protein is reduced as compared to a control (e.g., by deleting C12orf35 gene, or by introducing mutations), the yield of recombinant protein is significantly improved. As such, mammalian host cells (e.g., CHO cells) with reduced expression level or activity of C12orf35 protein are particularly suitable for recombinant production of pentameric complex.

Reducing the expression level or activity of a C12orf35 protein may be achieved by various means. For example, the expression level or activity of a C12orf35 protein may be reduced by gene knock-out, gene mutation, gene deletion, gene silencing or a combination of any of the forgoing. Gene knockout is a genetic technique by which a gene is made inoperative by disrupting its function. For example, a nucleic acid can be inserted into the coding sequence, thereby disrupting the gene function. Furthermore, the full-length C12orf35 gene (or a fragment thereof) can be deleted, whereby the expression of functional C12orf35 protein is substantially eliminated. For example, the deletion can be at least 30%, at least 40%, at least 50%, at least 55%, at least 60%, at least 65%, at least 70%, at least 75%, at least 80%, at least 85%, at least 90%, at least 95%, or 100% of the coding sequence of the C12orf35 gene. Another option is to introduce one or more mutations into the coding sequence, which renders a non- or a less functional C12orf35 protein. For example, one or more frameshift mutations can be introduced, resulting in a non- or less-functional C12orf35 protein. Alternatively or additionally, one or more stop codons can be introduced into the coding sequence so that a truncated, non- or less functional protein is obtained. Other options include but are not limited to one or more mutations in the promoter, in the 5'- and/or 3' UTR or other regulatory elements, e.g. by introducing a promoter deletion or by introducing a construct between the promoter and the transcription start. Methods for gene disruption to suppress or eliminate expression of the target gene are also well-known to the skilled person.

Since each cell has two copies of C12orf35 gene in its genome, in certain embodiments, at least one copy of the genomic sequence of the C12orf35 gene, or at least 50% of coding sequence of said C12orf35 gene, is deleted. In certain embodiments, both copies of the genomic sequences of the C12orf35 gene (or at least 50% of coding sequence of said C12orf35 gene from each copy) are deleted.

In certain embodiments, the deleted sequence comprises a portion of the telomeric region of chromosome 8 of a CHO cell. A telomeric region is a region of repetitive nucleotide sequences at each end of a chromatid, which protects the end of the chromosome from deterioration or from fusion with neighboring chromosomes. In certain embodiments, at least 30%, at least 40%, at least 50%, at least 55%, at least 60%, at least 65%, at least 70%, at least 75%, at least 80%, at least 85%, at least 90%, at least 95%, or 100% of the nucleotide sequence of the telomeric region of chromosome 8 of a CHO cell is deleted.

In certain embodiments, the deleted sequence further comprises deletion of a gene selected from the group consisting of: Bicd1, Amn1, methyltransferase-like protein 20, Dennd5b, FAM60A, Caprin2, Ipo8, RPS4Y2, and a combination thereof.

In certain embodiments, the deletion of the C12orf35 gene (or a fragment thereof) is due to a chromosome breakage. Chromosome breakage can be induced e.g. by treating the eukaryotic cells with a toxic agent that promotes chromosome breakage, such as e.g. MTX, aphidicolin or hygromycin. Other options for inducing chromosome breakages include but are not limited to radiation, irradiation, mutagens, cancerogenic substances and bleomycin. Chromosome breakages may also occur spontaneously during transfection e.g. electroporation. Methods for inducing chromosome breakage are also known to the skilled person and thus, do not need any detailed description here. After inducing chromosome breakage, eukaryotic cells having the desired breakpoint (which results in a deletion of C12orf35 gene, or a fragment thereof) can be identified e.g. be analyzing the DNA or by using the method according to the fifth aspect of the present disclosure. For example, the expression profile of the treated cells can be analyzed to determine whether the C12orf35 gene or genes located centromeric of gene C12orf35 are expressed, whether the expression is reduced or whether the genes are not expressed. For example, in the case of mouse or hamster cells it can be analyzed whether the C12orf35 gene is expressed and alternatively or in addition thereto, it can be analyzed whether one or more genes selected from the group consisting of methyltransferase-like protein 20, Dennd5b, FAM60A, Caprin2, Ipo8, Tmtc1 or genes that are located telomeric of the aforementioned genes (wherein telomeric in this respect means into the direction of the telomeric end) are expressed by the cell and/or whether the expression is reduced or substantially eliminated.

Reduction of expression level of C12orf35 protein may be achieved by post-transcriptional gene silencing, e.g. by antisense nucleic acid molecules, or molecules that mediate RNA interference. Non-limiting examples include siRNA, shRNA, miRNA, antisense oligonucleotides, etc., all of which are well known in the art.

Expression level of C12orf35 protein can be assessed by art-known methods, e.g., by measuring the level of mRNA encoding C12orf35 protein, or C12orf35 protein itself. Such methods include, for example northern blot, FACS, ImageStream, western blot, qPCR, RT-PCR, qRT-PCR, ELISA, Luminex, Multiplex, etc.

In certain embodiments, the expression level or activity of the C12orf35 protein is reduced by at least 3 fold, at least 5 fold, at least 10 fold, at least 20 fold, at least 30 fold, at least 40 fold, at least 50 fold, at least 60 fold, at least 70 fold, at least 75 fold, at least 80 fold, at least 90 fold, at least 100 fold, as compared to a control.

FAM60A Genes and FAM60A Proteins

In certain embodiments, the host cell is a cell in which the expression level or activity of FAM60A protein is reduced, as compared to a control. In certain embodiment, such cell is a CHO cell. U.S. Provisional Patent Application No. 61/919,340, filed Dec. 20, 2013, and incorporated herein by reference, provides a detailed description of mammalian cells wherein the expression level or activity of FAM60A protein is reduced.

A variety of controls may be used as discussed above. Expression level or activity of the FAM60A protein from a corresponding wild type cell can be used as a control. Alternatively, a control may be a pre-determined level or a threshold level that can be identified in literature or database.

FAM60A protein is a sub-unit of the SIN3-histone deacetylase (HDAC) complex (SIN3/HDAC complex) that functions in transcriptional repression (Munoz et al., 2012, THE Journal of Biological Chemistry VOL. 287, NO. 39, pp. 32346-32353; Smith et al., 2012, Mol Cell Proteomics 11 (12): 1815-1828). Histone deacetylases (HDAC) catalyze the removal of acetyl groups from histones. Acetylation of histones on lysines is a major mechanism for modulating chromatin conformation. Histone acetylation promotes a relaxed, transcriptionally active chromatin state whereas deacetylation catalyzed by histone deacetylases (HDACs) favor a silent, inactive state. Database analysis revealed the presence of at least one FAM60A ortholog in most metazoans, but not in nematodes. The FAM60A gene is conserved in metazoans and can be found in all vertebrate and most invertebrate genomes that have been completely sequenced. Sequence similarity research of FAM60A homologs indicates that predominantly, there is only a single representative member of this family in the genome. There are only few exceptions. According to the Smith et al, 2012, the FAM60A protein has a unique sequence lacking any known protein domains. Moreover, it was described by Smith et al 2012, that it does not exhibit any sequence homology to other known proteins in the human proteome. Sequence comparison between FAM60A proteins from different species showed that the FAM60A protein generally comprises three regions: (1) an N-terminus comprising highly conserved segments in all metazoans (2) a middle region which is highly conserved across vertebrates whereas in invertebrates it consists of a non-conserved spacer of a variable length (3) a C-terminus comprising highly conserved segments in all metazoans. Thus, highest conservation was observed in the FAM60A N- and C-terminal regions.

Studies indicate that FAM60A protein associates with SIN3/HDAC complexes in various eukaryotic cell types such as in particular mammalian cells. However, to date, functional information about FAM60A protein is limited. Recent functional studies (see Smith et al, 2012) indicate that FAM60A protein may repress gene expression and regulates a specific subset of genes. Smith et al 2012 report a role of FAM60A protein in the regulation of the TGF-beta signaling pathway, which plays a pivotal role in processes like cancer progression, metastasis, cell migration and immune surveillance. There are findings indicating that FAM60A protein acts as a transcriptional repressor of components of the TGF-beta signaling pathway whereas this FAM60A protein function seems to be permitted via its role in the SIN3-HDAC complex. Depletion of FAM60A protein in different cancer cell lines using siRNA against FAM60A coding sequence resulted in a change of normal cancer cell morphology. Furthermore, it was found that FAM60A protein levels do periodically change within the course of the cell cycle in U20S cells (Munoz et al, 2012). FAM60A knock-down experiments using FAM60A siRNA in U20S human bone osteosarcoma cells revealed that FAM60A protein restrains cyclin D1 gene expression.

Against this scientific background, it was surprising to find that reducing the expression or activity of FAM60A protein in a mammalian cell increases the stability of expression of recombinant proteins, without negatively affecting other characteristics of the cell that are important for recombinant expression. This correlation between the effects of protein FAM60A and the expression stability during prolonged culturing of the cells was unexpected. As such, mammalian host cells (e.g., CHO cells) with reduced expression level or activity of FAM60A protein are particularly suitable for recombinant production of pentameric complex.

The FAM60A gene is endogenously expressed in metazoan and hence in mammalian species such as human, mouse, rat and hamster, and the amino acid sequence of FAM60A is highly conserved in mammalian species as well as in vertebrates. Different names can be assigned in different species for the protein or the gene and non-limiting alternative names (aliases) are also listed above in Table 2 (below). For simplicity, in this disclosure, homologs and orthologs from different species are all referred to as "FAM60A gene" or "FAM60A protein."

The sequence listing shows exemplary amino acid sequences of known and/or predicted FAM60A proteins of different vertebrate species, namely *Homo sapiens* (SEQ ID NO: 28), *Mus musculus* (SEQ ID NO: 29), *Cricetulus griseus* (SEQ ID NO: 30). The predicted FAM60A cDNA of *Cricetulus griseus* is shown in SEQ ID NO: 31 (coding sequence from 14-679; see also NCBI Reference Sequence: XM_003505482.1). The FAM60A protein has not been described in detail in the literature. Thus, it was surprising that the expression stability of a recombinant host cell can be improved, if the genome of the host cell is altered such that the expression level or activity of endogenous protein FAM60A is reduced, as compared to a control. It was unexpected that FAM60A protein influences the expression stability of a recombinant product of interest.

Sequences of the FAM60A gene encoding the FAM60A protein have been reported in *Homo sapiens* (NCBI Gene-ID: 58516); *Rattus norvegicus* (NCBI Gene-ID: 686611); *Mus musculus* (NCBI Gene-ID: 56306); *Bos Taurus* (NCBI Gene-ID: 538649) and others. Transcript variants may exist in a species-dependent manner and in different numbers (e.g. the human FAM60A gene expresses three putative transcript isoforms which differ in the UTRs but encode the same protein).

Reducing the expression level or activity of a FAM60A protein may be achieved by various means. For example, the expression level or activity of a FAM60A protein may be reduced by gene knock-out, gene mutation, gene deletion, gene silencing or a combination of any of the forgoing. Gene knockout is a genetic technique by which a gene is made inoperative by disrupting its function. For example, a nucleic acid can be inserted into the coding sequence, thereby disrupting the gene function. Furthermore, the full-length FAM60A gene (or a fragment thereof) can be deleted, whereby the expression of functional FAM60A protein is substantially eliminated. For example, the deletion can be at least 30%, at least 40%, at least 50%, at least 55%, at least 60%, at least 65%, at least 70%, at least 75%, at least 80%, at least 85%, at least 90%, at least 95%, or 100% of the coding sequence of the FAM60A gene. Another option is to introduce one or more mutations into the coding sequence, which renders a non- or a less functional FAM60A protein. For example, one or more frameshift mutations can be introduced, resulting in a non- or less-functional FAM60A protein. Alternatively or additionally, one or more stop codons can be introduced into the coding sequence so that a truncated, non- or less functional protein is obtained. Other options include but are not limited to one or more mutations in the promoter, in the 5'- and/or 3' UTR or other regulatory elements, e.g. by introducing a promoter deletion or by introducing a construct between the promoter and the transcription start. Methods for gene disruption to suppress or eliminate expression of the target gene are also well-known to the skilled person.

Since each cell has two copies of FAM60A gene in its genome, in certain embodiments, at least one copy of the genomic sequence of the FAM60A gene, or at least 50% of coding sequence of said FAM60A gene, is deleted. In certain embodiments, both copies of the genomic sequences of the FAM60A gene (or at least 50% of coding sequence of said FAM60A gene from each copy) are deleted.

In certain embodiments, the deleted sequence comprises a portion of the telomeric region of chromosome 8 of a CHO cell. A telomeric region is a region of repetitive nucleotide sequences at each end of a chromatid, which protects the end of the chromosome from deterioration or from fusion with neighboring chromosomes. In certain embodiments, at least 30%, at least 40%, at least 50%, at least 55%, at least 60%, at least 65%, at least 70%, at least 75%, at least 80%, at least 85%, at least 90%, at least 95%, or 100% of the nucleotide sequence of the telomeric region of chromosome 8 of a CHO cell is deleted.

In certain embodiments, the deleted sequence further comprises a deletion of gene selected from the group consisting of: Caprin2 and Ipo8, and a combination thereof.

In certain embodiments, the deletion of the FAM60A gene is due to a chromosome breakage. Chromosome breakage can be induced by methods described above. After inducing chromosome breakage, cells having the desired breakpoint (which results in a deletion of gene FAM60A) can be identified e.g. be analyzing the DNA or by using the method according to the fifth aspect of the present disclosure. For example, the expression profile of the treated cells can be analyzed to determine whether the FAM60A gene or genes located centromeric of gene FAM60A are expressed, whether the expression is reduced or whether the genes are not expressed. For example, in case of mouse or hamster cells it can be analyzed whether the FAM60A gene is expressed and alternatively or in addition thereto, it can be analyzed whether one or more genes selected from the group consisting of Bicd1, C12orf35, methyltransferase-like protein 20, Dennd5b, Caprin2, Ipo8, Tmtc1 or genes that are located telomeric of the aforementioned genes (wherein telomeric in this respect means into the direction of the telomeric end) are expressed by the cell and/or whether the expression is reduced or substantially eliminated.

Reduction of expression level of FAM60A protein may achieve by post-transcriptional gene silencing, e.g. by antisense nucleic acid molecules, or molecules that mediate RNA interference. Non-limiting examples include siRNA, shRNA, miRNA, antisense oligonucleotides, etc., all of which are well known in the art.

Expression level of FAM60A protein can be assessed by art-known methods, e.g., by measuring the level of mRNA encoding FAM60A protein, or FAM60A protein itself. Such methods include, for example northern blot, FACS, ImageStream, western blot, qPCR, RT-PCR, qRT-PCR, ELISA, Luminex, Multiplex, etc.

In certain embodiments, the expression level or activity of the FAM60A protein is reduced by at least 3 fold, at least 5 fold, at least 10 fold, at least 20 fold, at least 30 fold, at least 40 fold, at least 50 fold, at least 60 fold, at least 70 fold, at least 75 fold, at least 80 fold, at least 90 fold, at least 100 fold, as compared to a control.

Matriptase Genes and Matriptases

In certain embodiments, the host cell is a cell in which the expression level or activity of matriptase is reduced, as compared to a control. In certain embodiment, such cell is a CHO cell. U.S. Provisional Patent application No. 61/985,589, filed Apr. 29, 2014 and incorporated herein by reference, and U.S. Provisional Patent Application No. 61/994,310, filed May 16, 2014 and incorporated herein by reference, provides a detailed description of mammalian cells wherein the expression level or activity of matriptase is reduced.

A variety of controls may be used as discussed above. Expression level or activity of the matriptase from a corresponding wild type cell can be used as a control. Alternatively, a control may be a pre-determined level or a threshold level that can be identified in literature or database.

Matriptase was first described in 1993 as a new gelatinolytic activity in cultured breast cancer cells. Matriptase belongs to the family of type II transmembrane serine proteases (TTSPs). Orthologs of matriptase are present in different vertebrate species, including mammalian species, and were identified for example in human, chimpanzee, dog, mouse, rat, chicken, zebrafish, spotted green pufferfish and tiger pufferfish which suggests a conserved evolutionary function. Matriptase is listed in the IUBMB Enzyme nomenclature as EC 3.4.21.109. Matriptase is also known as membrane-type serine protease 1 (MT-SP1) and suppressor of tumorigenicity-14 (ST14) (see Chen et al, The Transmembrane Serine Protease Matriptase: Implications for Cellular Biology and Human Diseases J Med Sci 2012; 32 (3): 097-108). It is an integral membrane protein with a single-span transmembrane domain close to the cytoplasmatic N-Terminus. The extracellular part consists of a stem region (including a single SEA, 2 CUB and 4 LDLRA domains) and the C-terminal serine protease domain that is structurally highly similar to other TTSPs and includes a conserved histidine/aspartic acid/serine (HDS) catalytic triad essential for catalytic activity (see e.g. List et al, Matriptase: Potent Proteolysis on the cell Surface; Mol Med 12 (1-3) 1-7, January-March 2006 and Chen et al, The Transmembrane Serine Protease Matriptase: Implications for Cellular Biology and Human Diseases J Med Sci 2012; 32 (3): 097-108). Matriptase is described as being expressed in the epithelia in many organ systems such as skin, breast, lung, epidermis, cornea, salivary gland, oral and nasal cavities, thyroid, thymus, esophagus, trachea, bronchioles, alveoli, stomach, pancreas, gallbladder, duodenum, small intestine, colon, rectum, kidney, adrenals, urinary bladder, ureter, seminal vesicles, epididymis, prostate, ovaries, uterus and vagina (see List et al, 2006 and Chen et al, 2012). Matriptase is synthesized as an inactive zymogen and is converted to its active form via a complicated process. Details regarding the activation process which involves endoproteolytic cleavages are described for the human matriptase in List et al 2006 and Chen et al 2012. Matriptase is bound to the membrane as type II transmembrane protein with the catalytic domain orientated into the extracellular space. Furthermore, it is described in the literature that a significant shedding of matriptase, respectively its extracellular part, occurs in vivo (see List et al, 2006 and Chen et al 2012). It is described in the literature that matriptase is shed in form of a complex, e.g. complexed to the Kunitz-type serine protease inhibitor HAI-1. Different studies suggest that in human cells the specific inhibitor HAI-1 facilitates the transport of the matriptase to the cell membrane as it was shown that removal or even single point mutations in HAI-1 lead to an accumulation of the matriptase in the Golgi compartment. In the literature, several different endogenous inhibitors of matriptase besides HAI-1 have been described such as HAI-2, antithrombin, alpha-1 antitrypsin and alpha-2-antiplasmin. Furthermore, also other inhibitors of matriptase have been described (see e.g. Chen et al, 2012). It is described in the literature that matriptase may play numerous roles in normal physiology such as skin barrier function, epithelial integrity, hair follicle development, and thymus homeostasis, and in human pathologies, such as osteoarthritis, atheroscleorisis, and tumor progression, invasion, and metastasis.

Against this scientific background which is unrelated to the recombinant production of a protein, the present finding that matriptase is a protease involved in clipping of recombinantly produced protein that are secreted by the host cells into the cell culture medium was highly surprising. Considering the large number and variety of proteases expressed in vertebrate cells, such as in particular mammalian cells, it was even more surprising that reducing the expression level or activity of this protein can significantly reduce clipping of the secreted polypeptide of interest in the cell culture medium. These advantageous effects are not seen with other, even closely related proteases. As such, mammalian host cells (e.g., CHO cells) with reduced expression level or activity of matriptase are particularly suitable for recombinant production of pentameric complex.

The sequence listing shows exemplary amino acid sequences of matriptase from different vertebrate species such as hamster (SEQ ID NO: 32-NCBI reference sequence: XP_003495890), human (SEQ ID NO: 33-NCBI reference sequence: NP_068813), mouse (SEQ ID NO: 34-NCBI Reference sequence: NP_035306).

The nucleotide sequences encoding matriptase from different mammalian species have also been reported. See, e.g. Chinese hamster (NCBI Gene-ID: 100755225); *Homo sapiens* (NCBI Gene-ID: 6768); *Mus musculus* (NCBI Gene-ID: 19143); *Rattus norvegicus* (NCBI Gene-ID: 114093); *Pan Troglodytes* (NCBI Gene-ID: 100188950) and others. Synonyms for some of the matriptase gene are listed in Table 3, commonly used is "ST14" or "St14."

As shown Table 3, matriptase is also referred to as "suppressor of tumorigenicity 14 protein" (e.g. for human) and "suppressor of tumorigenicity 14 protein homolog" (e.g. in mouse and Chinese hamster). For simplicity, in this disclosure, homologs and orthologs from different species are all referred to as "matriptase gene" or "matriptase" (protein).

Also described herein are functional variants of a matriptase (variants that have substantially the same catalytic activities as a wild type matriptase). For example, a matriptase variant can comprise a sequence that is at least 50%, at least 60%, at least 70%, at least 75%, at least 80%, at least 85%, at least 90%, at least 95%, at least 96%, at least 97%, at least 98% or at least 99% identical to any one of sequences of SEQ ID NOs: 32-34, and has the same, or substantially the same catalytic activities as a wild type matriptase protein. The catalytic activity of a matriptase variant can be assessed, e.g., by the chemical reaction to cleave various synthetic substrates with Arg or Lys at the P1 position and prefer small side-chain amino acids, such as Ala and Gly, at the P2 position (see, EC 3.4.21.109).

Also described herein are functional fragments of a matriptase (fragments that have substantially the same catalytic activities of a full-length matriptase). A functional fragment of a matriptase can be a subset of contiguous amino acid of the full-length matriptase disclosed herein, and has the same, or substantially the same catalytic activities as the full length protein sequence. The catalytic activity of a matriptase fragment can be assessed, e.g., by the chemical reaction to cleave various synthetic substrates with Arg or Lys at the P1 position and prefer small side-chain amino acids, such as Ala and Gly, at the P2 position (see, EC 3.4.21.109).

Reducing the expression level or activity of a matriptase may be achieved by various means. For example, the expression level or activity of a matriptase may be reduced by gene knock-out, gene mutation, gene deletion, gene silencing or a combination of any of the forgoing. Gene knockout is a genetic technique by which a gene is made inoperative by disrupting its function. For example, a nucleic acid can be inserted into the coding sequence, thereby disrupting the gene function. Furthermore, the full-length matriptase gene (or a fragment thereof) can be deleted, whereby the expression of functional matriptase is substantially eliminated. For example, the deletion can be at least 30%, at least 40%, at least 50%, at least 55%, at least 60%, at least 65%, at least 70%, at least 75%, at least 80%, at least 85%, at least 90%, at least 95%, or 100% of the coding sequence of the matriptase gene. Another option is to introduce one or more mutations into the coding sequence, which renders a non- or a less functional matriptase. For example, one or more frameshift mutations can be introduced, resulting in a non- or less-functional matriptase. Alternatively or additionally, one or more stop codons can be introduced into the coding sequence so that a truncated, non- or less functional protein is obtained. Other options include but are not limited to one or more mutations in the promoter, in the 5'- and/or 3' UTR or other regulatory elements, e.g. by introducing a promoter deletion or by introducing a construct between the promoter and the transcription start. Methods for gene disruption to suppress or eliminate expression of the target gene are also well-known to the skilled person.

Since each cell has two copies of matriptase gene in its genome, in certain embodiments, at least one copy of the genomic sequence of the matriptase gene, or at least 50% of coding sequence of said matriptase gene, or a functional fragment of said matriptase gene, is deleted. In certain embodiments, both copies of the genomic sequences of the matriptase gene (or at least 50% of coding sequence of said matriptase gene, or a functional fragment of said matriptase gene, from each copy) are deleted.

In certain embodiments, the host cell comprises a mutation in exon 2 in of the matriptase gene. Exon 2 is particularly suitable as a target to alter matriptase activity because there exist several different functional splicing variants. Thus, exons close to the N-terminus of matriptase such as e.g. exon 1, exon 2 and exon 3, are advantageous for introducing one or more mutations, in particular one or more frameshift mutations. A frameshift mutation in one of these exons most likely leads to a stop codon early in the sequence. Mutations may also be introduced in one of the subsequent exons, e.g. selected from exons 4 to 19.

In certain embodiments, the matriptase comprises as a mutation in the catalytic domain. The catalytic domain is the region of an enzyme that interacts with its substrate to cause the enzymatic reaction. One or more mutations can be introduced into this domain so that the catalytic activity of the protein is reduced as compared to a control. The catalytic domain comprises sequences encoded by exons 16, 17, 18 and 19. Mutations may be a deletion, an insertion, a substitution, or a combination thereof. The mutations can cause a frameshift mutation, a specific point mutation, a stop codon mutation, or a recombination thereof, in the sequence encoding the catalytic domain. Catalytic inactive mutants of matriptase such as e.g. G827R-matriptase or S805A-matriptase have also been described in the literature (see Désilets et al, The Journal of Biological Chemistry Vol. 283, No. 16, pp. 10535-10542, 2008). Furthermore, the crystal structure of the catalytic domain of a recombinant matriptase is known. From this structure and sequence data the skilled person can derive further specific targets for mutations to impair the catalytic function of the matriptase.

Reduction of expression level of matriptase may be achieved by post-transcriptional gene silencing, e.g. by antisense nucleic acid molecules, or molecules that mediate RNA interference. Non-limiting examples include siRNA, shRNA, miRNA, antisense oligonucleotides, etc., all of which are well known in the art.

Expression level of matriptase can be assessed by art-known methods, e.g., by measuring the level of mRNA encoding matriptase, or matriptase itself. Such methods include, for example northern blot, FACS, ImageStream, western blot, qPCR, RT-PCR, qRT-PCR, ELISA, Luminex, Multiplex, etc. The activity of matriptase can be assessed, e.g., according to its enzymatic activity.

In certain embodiments, the expression level or activity of the matriptase is reduced by at least 3 fold, at least 5 fold, at least 10 fold, at least 20 fold, at least 30 fold, at least 40 fold, at least 50 fold, at least 60 fold, at least 70 fold, at least 75 fold, at least 80 fold, at least 90 fold, at least 100 fold, as compared to a control.

TABLE 2

Abbreviations and alternative names (aliases) of products encoded by genes located in chromosome 8 of Chinese hamster or chromosome 6 of mouse.

| Abbreviation | In public annotation of Chinese hamster, the gene product is annotated as | In public annotation of mouse the gene product is annotated as | Aliases (see www.genecards.org) |
|---|---|---|---|
| Ccdc91 | Coiled-coil domain-containing protein 91 | Coiled-coil domain containing 91 | Coiled-Coil Domain Containing 91<br>P56<br>GGA-Binding Partner<br>P56 Accessory Protein<br>DKFZp779L1558<br>FLJ11088<br>Coiled-Coil Domain-Containing Protein 91<br>GGA Binding Partner<br>GGABP |
| Far2 | Fatty acyl CoA reductase 1 isoform 1 | Fatty acyl CoA reductase 2 | Fatty Acyl CoA Reductase 2<br>MLSTD1<br>SDR10E2<br>Male Sterility Domain-Containing Protein 1<br>EC 1.2.1.N2<br>FLJ10462<br>Male Sterility Domain Containing 1<br>Fatty Acyl-CoA Reductase 2<br>Short Chain |

TABLE 2-continued

Abbreviations and alternative names (aliases) of products encoded by genes located in chromosome 8 of Chinese hamster or chromosome 6 of mouse.

| Abbreviation | In public annotation of Chinese hamster, the gene product is annotated as | In public annotation of mouse the gene product is annotated as | Aliases (see www.genecards.org) |
|---|---|---|---|
| Ergic2 | Endoplasmic reticulum-Golgi intermediate compartment protein 2 | ERGIC and golgi 2 | Dehydrogenase/Reductase Family 10E, Member 2<br>ERGIC And Golgi 2<br>PTX1<br>Erv41<br>Cd002<br>CD14 Protein<br>Endoplasmic Reticulum-Golgi Intermediate Compartment Protein 2<br>ERV41<br>CDA14 |
| RPS4Y2 | 40S ribosomal protein S4, X isoform like | Ribosomal protein S4, Y linked 2 | Ribosomal Protein S4, Y-Linked 2<br>RPS4Y2P<br>Ribosomal Protein S4, Y-Linked 2 Pseudogene<br>40S Ribosomal Protein S4, Y<br>40S Ribosomal Protein S4, Y Isoform 2 |
| Tmtc1 | Transmembrane and TPR repeat-containing protein 1 | Transmembrane and tetratricopeptide repeat containing 1 | Transmembrane And Tetratricopeptide Repeat Containing 1<br>OLF<br>ARG99<br>FLJ31400<br>FLJ41625<br>TMTC1A<br>Transmembrane And Tetratricopeptide Repeat Containing 1A<br>Transmembrane And TPR Repeat-Containing Protein 1 |
| Zfp 1 | Zinc finger HIT domain-containing protein1 | | ZFP1 Zinc Finger Protein<br>ZNF475<br>Zinc Finger Protein 475<br>FLJ34243<br>Zinc Finger Protein 1<br>Zinc Finger Protein 1 Homolog (Mouse)<br>Zfp-1<br>Zinc Finger Protein 1 Homolog |
| IPO8 | Importin-8-like | Importin-8 | Importin 8<br>RANBP8<br>RAN Binding Protein 8<br>Ran-Binding Protein 8<br>IMP8<br>Imp8<br>Importin-8<br>RanBP8 |
| Caprin2 | Caprin-2-like protein | Caprin family member 2 | Caprin Family Member 2<br>C1QDC1<br>EEG1<br>RNG140<br>Caprin-2<br>Cytoplasmic Activation/Proliferation-Associated Protein 2<br>Gastric Cancer Multidrug Resistance-Associated Protein<br>C1q Domain-Containing Protein 1<br>RNA Granule Protein 140<br>FLJ11391<br>FLJ22569<br>C1q Domain Containing 1<br>EEG-1<br>KIAA1873<br>Protein EEG-1 |
| FAM60A | Protein FAM60A-like | Family with sequence similarity 60, member A | Family With Sequence Similarity 60, Member A<br>C12orf14<br>TERA<br>Tera Protein Homolog<br>Chromosome 12 Open Reading Frame 14<br>Protein FAM60A |

TABLE 2-continued

Abbreviations and alternative names (aliases) of products encoded by genes located in chromosome 8 of Chinese hamster or chromosome 6 of mouse.

| Abbreviation | In public annotation of Chinese hamster, the gene product is annotated as | In public annotation of mouse the gene product is annotated as | Aliases (see www.genecards.org) |
|---|---|---|---|
| Dennd5b | Denn domain-containing protein 5B-like | DENN/MADD domain containing 5B | DENN/MADD Domain Containing 5B<br>Rab6IP1-Like Protein<br>MGC24039<br>DENN Domain-Containing Protein 5B |
| METTL20 | Methyltransferase-like protein 20 | 4833442J19Rik | METTL20<br>C12orf72<br>DKFZp451L235<br>MGC50559<br>Chromosome 12 Open Reading Frame 72<br>Methyltransferase-Like Protein 20<br>EC 2.1.1. |
| AMN1 | Putative protein AMN1 like protein<br><br>Opioid growth factor receptor-like protein | Antagonist of mitotic exit network 1<br><br>Opioid growth factor receptor-like protein | Antagonist Of Mitotic Exit Network 1 Homolog (*S. Cerevisiae*)<br>Protein AMN1 Homolog |
| C12orf35 | Uncharacterized protein C12orf35 homolog | likely orthologue of *H. sapiens* chromosome 12 open reading frame 35 (C12orf35); 2810474O19Rik | KIAA1551,<br>C12orf35<br>FLJ10652,<br>FLJ20696<br>Chromosome 12 Open Reading Frame 35<br>Uncharacterized Protein C12orf35<br>Uncharacterized Protein KIAA1551 |
| Bicd 1 | Putative protein bicaudal D | Bicaudal D homolog 1 | Bicaudal D Homolog 1 (*Drosophila*)<br>Bic-D 1<br>Bicaudal D (*Drosophila*) Homolog 1<br>BICD<br>Cytoskeleton-Like Bicaudal D Protein Homolog 1<br>Protein Bicaudal D Homolog 1 |

TABLE 3

Exemplary alternative names of matriptase gene and/or the encoded protein product matriptase used in the literature (alphabetical order)

Breast cancer 80 kDa protease
CAP3
Channel-activating protease 3
EC 3.4.21.109
Epithin
HAI
Matriptase
Matriptase-1
Membrane-type serine protease 1
MT-SP1; MTSP1
Prostamin
PRSS14 g.p. (*Homo sapiens*), PRSS14
Serine endopeptidase SNC19
Serine protease 14
Serine protease TADG-15; TADG-15; TADG15
SNC19
ST14 (official gene name in humans according to HGNC)
St14
Suppression of tumorigenicity-14 Protein; suppression of tumorigenicity 14 (colon carcinoma, matriptase, epithin)
Suppressor of tumorigenicity 14 protein
Suppressor of tumorigenicity 14 protein homolog (mouse)
TMPRSS14
Tumor associated differentially expressed gene 15 protein A suitable host cell can have any combinations of modifications described herein, e.g., a cell in which both the expression level or activity of C12orf35 protein is reduced in said cell, as compared to a control, and the expression level or activity of FAM60A protein is reduced in said cell, as compared to a control. Other combinations include, e.g., reduction of C12orf35 protein expression level or activity, and reduction of matriptase expression level or activity; reduction of FAM60A protein expression level or activity, and reduction of matriptase expression level or activity; reduction of C12orf35 protein expression level or activity, reduction of FAM60A protein expression level or activity, and reduction of matriptase expression level or activity; reduction of C12orf35 protein expression level or activity, and inclusion of dihydrofolate reductase (DHFR) sequence as a selection marker, etc.

The host cells described herein are suitable for large scale culture. For example, the cell cultures can be 10 L, 30 L, 50 L, 100 L, 150 L, 200 L, 300 L, 500 L, 1000 L, 2000 L, 3000 L, 4000 L, 5000 L, 10,000 L or larger. In some embodiments, the cell culture size can range from 10 L to 5000 L, from 10 L to 10,000 L, from 10 l, to 20,000 L, from 10 l, to 50,000 L, from 40 l, to 50,000 L, from 100 L to 50,000 L, from 500 L to 50,000 L, from 1000 L to 50,000 L, from 2000 L to 50,000 L, from 3000 l, to 50,000 L, from 4000 L to 50,000 L, from 4500 L to 50,000 L, from 1000 L to 10,000 L, from 1000 L to 20,000 L, from 1000 L to 25,000 L, from 1000 L to 30,000 L, from 15 L to 2000 L, from 40 L to 1000 L, from 100 L to 500 L, from 200 L to 400 L, or any integer there between.

Media components for cell culture are known in the art, and may include, e.g., buffer, amino acid content, vitamin content, salt content, mineral content, serum content, carbon source content, lipid content, nucleic acid content, hormone content, trace element content, ammonia content, co-factor content, indicator content, small molecule content, hydrolysate content and enzyme modulator content.

4. Purification of Pentameric Complex from the Cell Culture

The pentameric complex produced in accordance with the methods described herein can be harvested from host cells, and purified using any suitable methods. Suitable methods include precipitation and various types of chromatography, such as hydrophobic interaction, ion exchange, affinity, chelation, and size exclusion, all of which are known in the art. Suitable purification schemes can be created using two or more of these or other suitable methods. If desired, one or more of the subunit of the pentameric complex can comprise a "tag" that facilitates purification, such as an epitope tag or a HIS tag, Strep tag. Such tagged polypeptides can conveniently be purified, for example from conditioned media, by chelating chromatography or affinity chromatography. Optionally, the tag sequence may be cleaved post-purification.

For example, WO2014/005959 discloses exemplary methods of purifying pentameric complex by affinity chromatography.

In certain embodiments, one or more subunits of the pentameric complex comprise a tag for affinity purification. Examples of affinity-purification tags include, e.g., His tag (binds to metal ion), an antibody (binds to protein A or protein G), maltose-binding protein (MBP) (binds to amylose), glutathione-S-transferase (GST) (binds to glutathione), FLAG tag (Asp-Tyr-Lys-Asp-Asp-Asp-Asp-Lys (SEQ ID NO: 37)) (binds to an anti-flag antibody), Strep tag (binds to streptavidin or a derivative thereof).

The structure of gH/gL/pUL128/pUL130/pUL131 pentameric complex is unknown. However, if the affinity-purification tag is attached to a site that interferes with the formation of pentameric complex, or a site that is buried within the complex, affinity-purification would not be successful. The following sites are believed to be suitable for attaching an affinity-purification tag, as the tag does not appear to interfere with formation of pentameric complex, and appears to be expose at the surface of an assembled pentamer: (i) C-terminal region of pUL130, (ii) N-terminal region of pUL130, (iii) C-terminal region of pUL131, (iv) N-terminal region of pUL131, (v) C-terminal region of pUL128, (vi) N-terminal region of pUL128, or a combination thereof In certain embodiments, the pentameric complex does not comprise a purification tag.

Another suitable method is ion-exchange chromatography. Examples of materials useful in the ion exchange chromatography include DEAE-cellulose, QAE-cellulose, DEAE-cephalose, QAE-cephalose, DEAE-Toyopearl, QAE-Toyopearl, Mono Q, Mono S, Q sepharose, SP sepharose, etc. In one exemplary embodiment, the method uses Mono S column. In another exemplary embodiment, the method uses Mono Q column.

In certain embodiments, the yield of CMV pentameric complex is at least about 0.01 g/L, at least about 0.02 g/L, at least about 0.03 g/L, at least about 0.05 g/L, at least about 0.06 g/L, at least about 0.07 g/L, at least about 0.08 g/L, at least about 0.09 g/L, at least about 0.1 g/L, at least about 0.15 g/L, at least about 0.20 g/L, at least about 0.25 g/L, at least about 0.3 g/L, at least about 0.35 g/L, at least about 0.4 g/L, at least about 0.45 g/L, at least about 0.5 g/L, at least about 0.55 g/L, at least about 0.6 g/L, at least about 0.65 g/L, at least about 0.7 g/L, at least about 0.75 g/L, at least about 0.8 g/L, at least about 0.85 g/L, at least about 0.9 g/L, at least about 0.95 g/L, or at least about 1.0 g/L.

5. Definitions

The term "complex-forming fragment" of a CMV protein (such as gH, gL, pUL128, pUL130, or pUL131) refers to any part or portion of the protein that retains the ability to form a complex with another CMV protein. Such complexes include, e.g., gH/gL/pUL128/pUL130/pUL131 pentameric complex. Fragments that retain the ability to form the pentameric complex are also referred to as "pentamer-forming fragments."

A "large scale culture" refers to a culture that is at least about 10 liters in size, (e.g., a volume of at least about 10 L, at least about 20 L, at least about 30 L, at least about 40 L, at least about 50 L, at least about 60 L, at least about 70 L, at least about 80 L, at least about 90 L, at least about 100 L, at least about 150 L, at least about 200 L, at least about 250 L, at least about 300 L, at least about 400 L, at least about 500 L, at least about 600 L, at least about 700 L, at least about 800 L, at least about 900 L, at least about 1000 L, at least about 2000 L, at least about 3000 L, at least about 4000 L, at least about 5000 L, at least about 6000 L, at least about 10,000 L, at least about 15,000 L, at least about 20,000 L, at least about 25,000 L, at least about 30,000 L, at least about 35,000 L, at least about 40,000 L, at least about 45,000 L, at least about 50,000 L, at least about 55,000 L, at least about 60,000 L, at least about 65,000 L, at least about 70,000 L, at least about 75,000 L, at least about 80,000 L, at least about 85,000 L, at least about 90,000 L, at least about 95,000 L, at least about 100,000 L, etc.).

A "soluble" pentameric complex refers to gH/gL/pUL128/pUL130/pUL131 complex wherein the gH subunit does not comprise the transmembrane domain.

Throughout the specification, including the claims, where the context permits, the term "comprising" and variants thereof such as "comprises" or "comprising" are to be interpreted as including the stated integer or integers without necessarily excluding any other integers.

Sequence identity is calculated according to the percentage of residue matches between two polynucleotide sequences, or nucleotide matches between two polynucleotide sequences, aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity may be measured over the length of an entire defined sequence, or may be measured over a shorter length, for example, over the length of a fragment taken from a larger, defined sequence, for instance, a fragment of at least 45, at least 60, at least 90, at least 120, at least 150, at least 210 or at least 450 contiguous residues or nucleotides. If the length is not specified, the sequence identity is calculated across the full-length of the shorter of the two sequences.

This invention is further illustrated by the following examples which should not be construed as limiting.

EXAMPLES

This example is related to producing CMV pentameric protein complex by CHO cell lines in which the coding sequences of the pentamer subunits were stably integrated into the chromosome. The cell lines are also referred as CHO stable cell lines.

As shown in this example, these stable CHO cell lines produced functional CMV pentamer, with all five subunits assembled in the natural conformation. The yield is high, thereby enabling the production of pentameric complex in a large commercial scale. These cell lines are particularly suitable for large scale manufacturing of CMV vaccines using pentamer.

As shown in this example, nucleotide sequences encoding gH ectodomain, gL, pUL128, pUL130 and pUL131 were cloned into single or double expression vectors, with subgenomic promoters and IRES to drive the expression of individual component (FIG. 1). Specifically, coding sequences for gH ectodomain, full-length gL, pUL128, pUL130 and pUL131 were codon optimized for mammalian culture expression, synthesized and cloned into single expression vector (with Neo and DHFR selection) driven by CMV promoter (for gH and UL128) and EV71 IRES (for gL, UL130, UL131) for expression; or dual expression vectors, one with Neo and DHFR selection for gH driven by CMV promoter, and gL driven by CMV promoter or EV71 IRES, and one with Hyg and Frα selection for UL128 driven by CMV promoter, UL130 and UL131 driven by EV71 IRES (FIG. 1). Affinity purification tags such as His tag and/or Strep tag were introduced to C-terminus of gH ectodomain and/or UL130 to facilitate purification. Stop codon and transmembrane domain of gH was also introduced at C-terminus of gH ectodomain to facilitate FACS subcloning (FIG. 1).

The expression plasmid or plasmids were transfected into a panel of CHO host cells, including (i) CHOC8TD, (ii) CHOHPT3 and (iii) CHOC8TD matriptase KO cell lines.

CHOC8TD is derived from a CHO K1 cell line and further modified by deleting telomeric region of chromosome, so this cell line has the following characteristics: (i) chromosome 8 telomere deleted; (ii) high productivity and good cell growth; and (iii) potential problems of high proteolytic degradation. CHOHPT3 is a CHO K1 cell line showing reduced proteolytic activity, so this cell line has the following characteristics: (i) lower proteolytic degradation than CHOC8TD, and (ii) lower growth, productivity and cloning efficiency than CHOC8TD. CHOC8TD metriptase KO was derived from CHOC8TD, with matriptase knocked out, so this cell line has the following characteristics: (i) Matriptase (serine protease) knocked out; and (ii) less proteolytic degradation.

The expression plasmid or plasmids comprising coding sequences for gH, gL, UL128, UL130 and UL131 were transfected in all three host cells with AMAXA nucleofection. For single vector strategy, the transfected cells were selected by G418 and MTX sequentially. For dual vector strategy, the transfected cells were selected by Hyg then MTX sequentially.

Figure 2:
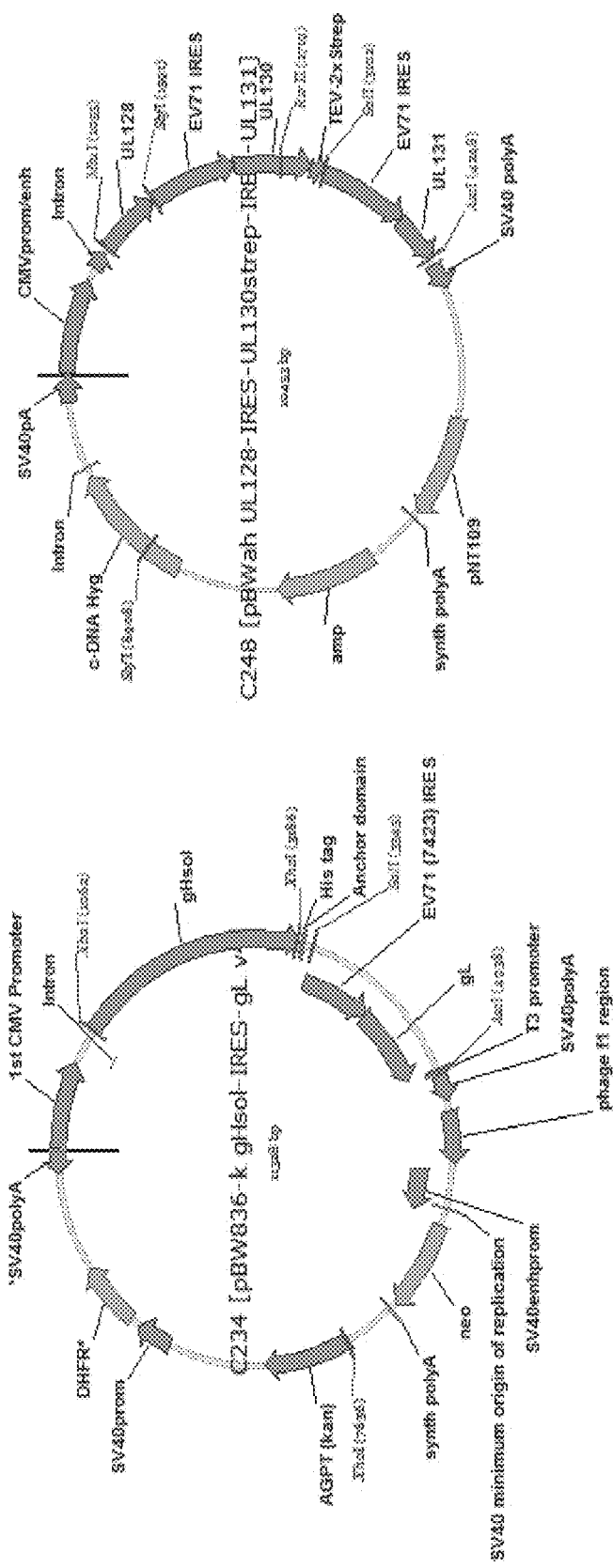
FIG. 2 shows the plasmid maps of the expression vectors used for transfection of CHO cells.

The surviving cell pools were batch cultured to produce pentamer protein to evaluation protein for yield with indirect ELISA, gH/gL contamination and gL degradation with western and SDS-PAGE. Based on pentamer yield and cell growth, the CHO transfect pool with Vector Strategy 2 (FIG. 1), using CHOC8TD host cells, were selected for single cell cloning (expression plasmids shown in FIG. 2). The selected clones show high yield and less gH/gL contamination.

Figure 3:
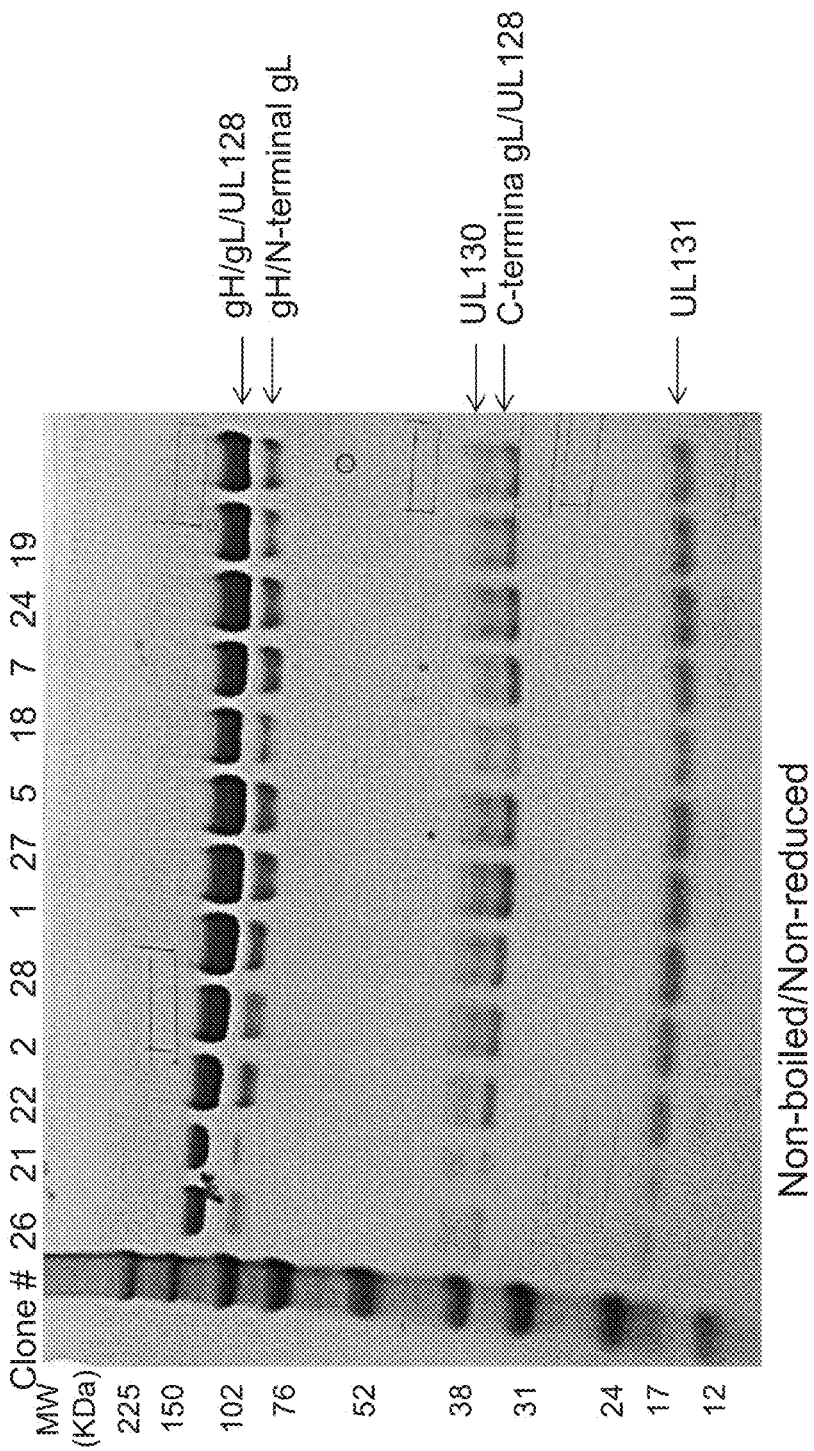
FIG. 3 shows SDS-PAGE analysis of purified pentamer produced with top 12 clones.

Single clones were sorted with FACS using pentamer-specific mAb (~200). The top 30 clones were first selected based on pentamer titer evaluated with indirect ELISA and further down-selected to top 12 clones. Fed-batch culture followed with Strep affinity purification showed that the top 12 can produce pentamer with yield >300 mg/L and high purity (FIG. 3). In fact, the top clones produced pentamer with yield from about 0.3 g/L to about 0.5 g/L. The purified protein complex was evaluated for binding with a panel of mAb against pentamer, and was shown to present all the key epitopes.

Figure 4:
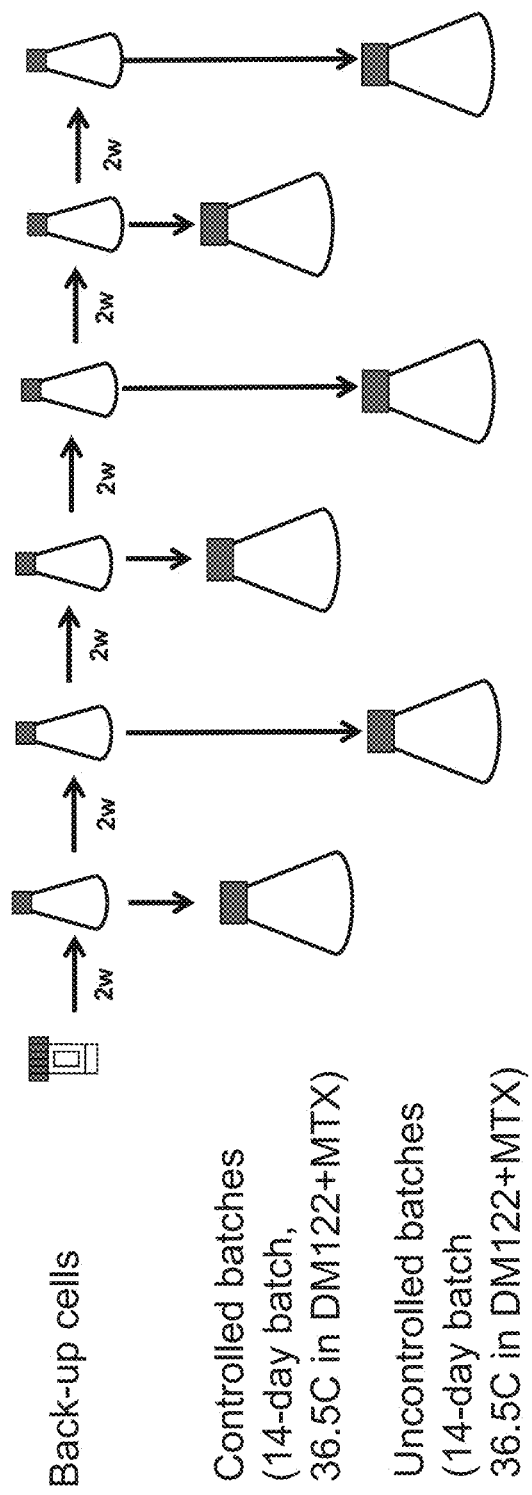
FIG. 4 illustrates the experimental designs used for studying the stability of top 12 clones.

The top 12 clones were further evaluated through 14-week stability studies (FIG. 4). The controlled and uncontrolled batches were evaluated for cell growth and pentamer titer and Clone VF7 was selected.

Figure 5:
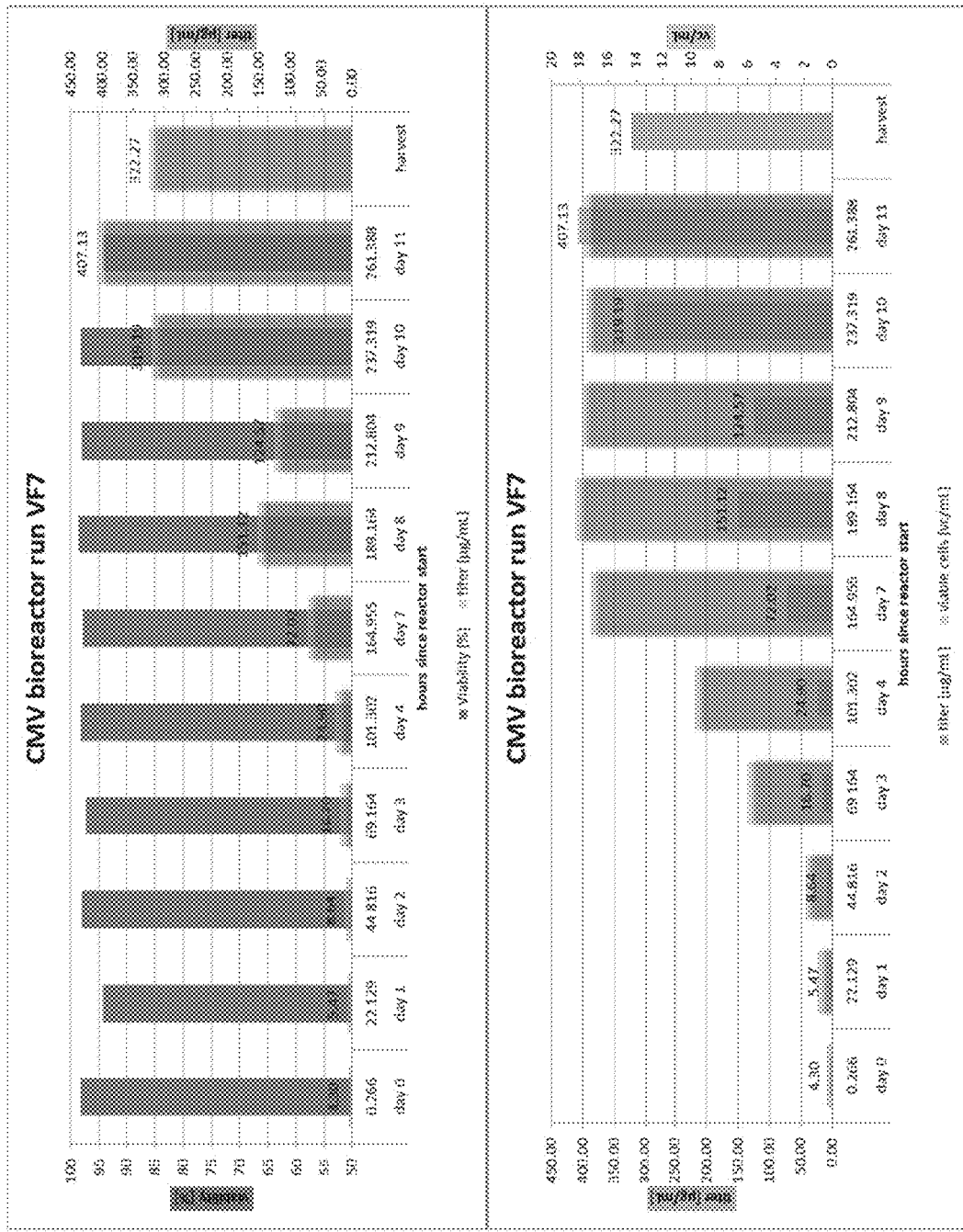
FIG. 5 shows the yield of pentamer produced by top clone VF7.

Bioreactor production of pentamer with the top clone VF7 was also assessed. This clone produced >100 mg/L purified pentamer (FIG. 5).

As exemplified herein, stable CHO cells can be used to express pentamer. This is in contrast to transient expression by HEK293 cells. CHO stable cell lines of the invention can produce pentamer protein consistently with 100 fold higher yield.

The ability to produce stable CHO cell lines in which coding sequences of all five subunits of pentamer are integrated into chromosome, as exemplified herein, is quite remarkable. There always exist uncertainties as to whether a stable cell line can be generated, even for a single protein. For example, when a coding sequence for human IGF-1 was introduced into CHO cells to generate a stable line, it was discovered that the resulting IGF-1/CHO cell lines showed cell growth inhibition and low titers. This maximum titer measurement was about 8 ug/ml which corresponds to 100 mg/L of an antibody titer (based on molar mass). In comparison, the average titer measurements of a recombinant antibody in bioreactor process are around 3 g/L. One cause of the low titer of IGF-1 was reduced cell growth and low cell viability of IGF-1 expressing cells. During an antibody expression process, CHO-K1 derivative cell cells grow up to $2 \times 10^7$ cells/ml and the cell viability is over 97% during the first 230-260 h cultivation time. In contrast CHO-K1 derivative cells expressing IGF-1 grew only up to $0.5 \times 10^7$ cells/ml and the cell viability had already dropped to under 97% after two days. For additional details, see, U.S. Provisional application No. 61/738,466, filed Dec. 18, 2012 and PCT application publication No. WO/2014/097113, filed Dec. 16, 2013.

Therefore, the inventors faced significant additional difficulties because the coding sequences for all five CMV pentamer subunits must be stably integrated into the CHO cell genome. The inventors overcame these difficulties, as evidenced by the selected clones showing high yields, with recombinantly produced pentamer in its natural conformation and with all key epitopes.

The various features and embodiments of the present invention, referred to in individual sections above apply, as appropriate, to other sections, mutatis mutandis. Consequently features specified in one section may be combined with features specified in other sections, as appropriate.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and GenBank sequences cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

Particular embodiments of the invention include:

1. A recombinant mammalian cell, comprising: one or more polynucleotide sequences encoding cytomegalovirus (CMV) pentameric complex, wherein said pentameric complex comprises: gH or a complex-forming fragment thereof, gL or a complex-forming fragment thereof, pUL128 or a complex-forming fragment thereof, pUL130 or a complex-forming fragment thereof, and pUL131 or a complex-forming fragment thereof; wherein said one or more polynucleotide sequences are integrated into the genomic DNA of said mammalian cell.
2. The mammalian cell of embodiment 1, wherein said mammalian cell is a Chinese Hamster Ovary (CHO) cell.
3. The mammalian cell of embodiment 2, wherein said CHO cell is a CHO-K1 cell, CHO-DUXB11, or CHO-DG44 cell.
4. The mammalian cell of any one of embodiments 1-3, wherein the expression level or activity of C12orf35 protein is reduced in said cell, as compared to a control.
5. The mammalian cell of embodiment 4, wherein at least one copy of the genomic sequence of the C12orf35 gene, or at least 50% of coding sequence of said C12orf35 gene, is deleted.
6. The mammalian cell of embodiment 5, wherein both copies of the genomic sequences of the C12orf35 gene, or at least 50% of coding sequence of said C12orf35 gene from each copy, are deleted.
7. The mammalian cell of embodiment 4 or 5, wherein at least one copy of the telomeric region of chromosome 8 of a CHO cell that comprises the C12orf35 gene is deleted.
8. The mammalian cell of embodiment 7, wherein said telomeric region further comprises a gene selected from the group consisting of: Bicd1, Amn1, methyltransferase-like protein 20, Dennd5b, FAM60A, Caprin2, Ipo8, RPS4Y2, and a combination thereof.
9. The mammalian cell of any one of embodiments 4-8, wherein said C12orf35 protein comprises a sequence that is at least 80% identical to any one of the sequences selected from the group consisting of SEQ ID NOs: 21, 22, 23, 24 and 35.
10. The mammalian cell of any one of embodiments 4-9, wherein said C12orf35 gene comprises a sequence that is at least 80% identical to SEQ ID NO: 25.
11. The mammalian cell of embodiment 4, wherein said cell comprises a mutation in the promoter, 5'UTR, or 3'UTR of said C12orf35 gene.
12. The mammalian cell of embodiment 4, wherein said C12orf35 protein comprises as a mutation that reduces its activity, as compared to a control.
13. The mammalian cell of any one of embodiments 1-12, wherein the expression level or activity of FAM60A protein is reduced in said cell, as compared to a control.
14. The mammalian cell of embodiment 13, wherein at least one copy of the genomic sequence of the FAM60A gene, or at least 50% of coding sequence of said FAM60A gene, is deleted.
15. The mammalian cell of embodiment 14, wherein both copies of the genomic sequences of the FAM60A gene, or at least 50% of coding sequence of said FAM60A gene from each copy, are deleted.
16. The mammalian cell of embodiment 13 or 14, wherein said deleted sequence comprises a portion of the telomeric region of chromosome 8 of a CHO cell.
17. The mammalian cell of embodiment 16, wherein said deleted sequence further comprises a gene selected from the group consisting of: Caprin2 and Ipo8, and a combination thereof.
18. The mammalian cell of any one of embodiments 13-17, wherein said FAM60A protein comprises a sequence that is at least 80% identical to any one of the sequences selected from the group consisting of SEQ ID NOs: 28, 29, and 30.
19. The mammalian cell of any one of embodiments 13-18, wherein said FAM60A gene comprises a sequence that is at least 80% identical to SEQ ID NO: 31.
20. The mammalian cell of embodiment 13, wherein said cell comprises a mutation in the promoter, 5'UTR, or 3'UTR of said FAM60A gene.
21. The mammalian cell of embodiment 13, wherein said FAM60A protein comprises as a mutation that reduces its activity, as compared to a control.
22. The mammalian cell of any one of embodiments 1-21, wherein the expression level or activity of matriptase is reduced in said cell, as compared to a control.
23. The mammalian cell of embodiment 22, wherein at least one copy of the genomic sequence of the matriptase gene, or at least 50% of coding sequence of said matriptase gene, is deleted.
24. The mammalian cell of embodiment 23, wherein both copies of the genomic sequences of the matriptase gene, or at least 50% of coding sequence of said matriptase gene from each copy, are deleted.
25. The mammalian cell of any one of embodiments 22-25, wherein said matriptase comprises a sequence that is at least 80% identical to any one of the sequences selected from the group consisting of SEQ ID NOs: 32, 33, and 34.
26. The mammalian cell of embodiment 22, wherein said cell comprises a mutation in exon 2 of the matriptase gene.
27. The mammalian cell of embodiment 22, wherein said cell comprises a mutation in the promoter, 5'UTR, or 3'UTR of the matriptase gene.
28. The mammalian cell of embodiment 22, wherein said matriptase comprises as a mutation that reduces its activity, as compared to a control.
29. The mammalian cell of embodiment 28, wherein said matriptase comprises as a mutation in the catalytic domain.
30. The mammalian cell of any one of embodiments 1-29, wherein the endogenous dihydrofolate reductase (DHFR) of said mammalian cell is deficient.
31. The mammalian cell of any one of embodiments 1-29, wherein the endogenous dihydrofolate reductase (DHFR) of said mammalian cell is competent.
32. The mammalian cell of any one of embodiments 1-31, wherein said complex-forming fragment of gH does not comprise the signal sequence of a full-length gH protein.

33. The mammalian cell of any one of embodiments 1-32, wherein said complex-forming fragment of gH does not comprise the transmembrane domain of a full-length gH protein.

34. The mammalian cell of any one of embodiments 1-33, wherein said complex-forming fragment of gH comprises the ectodomain of a full-length gH protein.

35. The mammalian cell of any one of embodiments 1-34, wherein said gH comprises a sequence selected from the group consisting of SEQ ID NOs: 1, 2, 3, 4, and 5.

36. The mammalian cell of any one of embodiments 1-35, wherein said complex-forming fragment of gH (i) forms part of the pentameric gH/gL/pUL128/pUL130/pUL131 complex; and (ii) comprises at least one epitope from SEQ ID NO: 1, SEQ ID NO: 2, SEQ ID NO: 3, SEQ ID NO: 4, or SEQ ID NO: 5.

37. The mammalian cell of any one of embodiments 1-36, wherein said complex-forming fragment of gL does not comprises the signal sequence of a full-length gL protein.

38. The mammalian cell of any one of embodiments 1-37, wherein said gL comprises a sequence selected from the group consisting of SEQ ID NOs: 6, 7, 8, and 9.

39. The mammalian cell of any one of embodiments 1-38, wherein said complex-forming fragment of gL (i) forms part of the pentameric gH/gL/pUL128/pUL130/pUL131 complex; and (ii) comprises at least one epitope from SEQ ID NO: 6, SEQ ID NO: 7, SEQ ID NO: 8, or SEQ ID NO: 9.

40. The mammalian cell of any one of embodiments 1-39, wherein said complex-forming fragment of pUL128 does not comprises the signal sequence of a full-length pUL128 protein.

41. The mammalian cell of any one of embodiments 1-40, wherein said pUL128 comprises a sequence selected from the group consisting of SEQ ID NOs: 10, 11, 12 and 13.

42. The mammalian cell of any one of embodiments 1-41, wherein said complex-forming fragment of pUL128 (i) forms part of the pentameric gH/gL/pUL128/pUL130/pUL131 complex; and (ii) comprises at least one epitope from SEQ ID NO: 10, SEQ ID NO: 11, SEQ ID NO: 12, or SEQ ID NO: 13.

43. The mammalian cell of any one of embodiments 1-42, wherein said complex-forming fragment of pUL130 does not comprises the signal sequence of a full-length pUL130 protein.

44. The mammalian cell of any one of embodiments 1-43, wherein said pUL130 comprises a sequence selected from the group consisting of SEQ ID NOs: 14, 15, and 16.

45. The mammalian cell of any one of embodiments 1-44, wherein said complex-forming fragment of pUL130 (i) forms part of the pentameric gH/gL/pUL128/pUL130/pUL131 complex; and (ii) comprises at least one epitope from SEQ ID NO: 14, SEQ ID NO: 15, or SEQ ID NO: 16.

46. The mammalian cell of any one of embodiments 1-45, wherein said complex-forming fragment of pUL131 does not comprises the signal sequence of a full-length pUL131 protein.

47. The mammalian cell of any one of embodiments 1-46, wherein said pUL131 comprises a sequence selected from the group consisting of SEQ ID NOs: 17, 18, 19, and 20.

48. The mammalian cell of any one of embodiments 1-47, wherein said complex-forming fragment of pUL131 (i) forms part of the pentameric gH/gL/pUL128/pUL130/pUL131 complex; and (ii) comprises at least one epitope from SEQ ID NO: 17, SEQ ID NO: 18, SEQ ID NO: 19, or SEQ ID NO: 20.

49. The mammalian cell of any one of embodiments 1-48, wherein said pentameric complex is soluble.

50. The mammalian cell of any one of embodiments 1-49, wherein said pentameric complex is secreted from the host cell.

51. A large scale culture comprising the mammalian cell of any one of embodiments 1-50, wherein said culture is at least 20 liter in size.

52. A large scale culture comprising the mammalian cell of any one of embodiments 1-51, wherein said culture is at least 50 liter in size.

53. The large scale culture of 51 or 52, wherein the yield of CMV pentameric complex is at least 0.05 g/L.

54. The large scale culture of 51 or 52, wherein the yield of CMV pentameric complex is at least 0.1 g/L.

55. A cytomegalovirus (CMV) pentameric complex produced by the mammalian cell of any one of embodiments 1-50, or the large scale culture of any one of embodiments 51-54.

56. A composition comprising the pentameric complex of embodiment 55.

57. A process of producing cytomegalovirus (CMV) pentameric complex, wherein said pentameric complex comprises: gH or a complex-forming fragment thereof, gL or a complex-forming fragment thereof, pUL128 or a complex-forming fragment thereof, pUL130 or a complex-forming fragment thereof, and pUL131 or a complex-forming fragment thereof, comprising:
   (i) culturing the mammalian cell of any one of embodiments 1-50 under a suitable condition, thereby expressing said pentameric complex; and
   (ii) harvesting said pentameric complex from the culture.

58. The process of embodiment 57, further comprising purifying said pentameric complex.

59. A cytomegalovirus (CMV) pentameric complex produced by the process of embodiment 57 or 58.

60. A composition comprising the pentameric complex of embodiment 59.

61. The composition of embodiment 56 or 60, wherein said pentameric complex has a purity of at least 95%, by mass.

62. The composition of embodiment 61, further comprising an adjuvant, such as an aluminum salt, or MF59.

63. The composition of embodiment 61 or 62, for use in inducing an immune response against CMV.

64. The cytomegalovirus (CMV) pentameric complex of embodiment 55, wherein said pentameric complex is immunogenic.

65. The cytomegalovirus (CMV) pentameric complex of embodiment 64, wherein antibodies to said pentameric complex are neutralizing antibodies.

What is claimed is:

1. A recombinant CHO cell, comprising:
a polynucleotide sequence encoding cytomegalovirus (CMV) pentameric complex, wherein said pentameric complex comprises: gH or a complex-forming fragment thereof, gL or a complex-forming fragment thereof, pUL128 or a complex-forming fragment thereof, pUL130 or a complex-forming fragment thereof, and pUL131 or a complex-forming fragment thereof;
wherein said one or more polynucleotide sequences are integrated into the genomic DNA of said CHO cell; and
wherein (i) the expression level or activity of C12orf35 protein is reduced in said cell as compared to a control, (ii) a telomeric region of chromosome 8 of said cell is deleted, (iii) the expression level or activity of FAM60A protein is reduced in said cell as compared to a control, (iv) the expression level or activity of matriptase is reduced in said cell as compared to a control, or (v) a combination of (i) to (iv).

2. The CHO cell of claim 1, wherein said CHO cell is a CHO-K1 cell, CHO-DUXB11, CHO-DG44 cell, or CHO-S cell.

3. The CHO cell of claim 1, wherein the expression level or activity of C12orf35 protein is reduced in said cell as compared to a control.

4. The CHO cell of claim 3, wherein at least one copy of the genomic sequence of the C12orf35 gene, or at least 50% of coding sequence of said C12orf35 gene, is deleted.

5. The CHO cell of claim 1, wherein a telomeric region of chromosome 8 of said cell is deleted.

6. The CHO cell of claim 1, wherein the expression level or activity of FAM60A protein is reduced in said cell as compared to a control.

7. The CHO cell of claim 6, wherein at least one copy of the genomic sequence of the FAM60A gene, or at least 50% of coding sequence of said FAM60A gene, is deleted.

8. The CHO cell of claim 1, wherein the expression level or activity of matriptase is reduced in said cell as compared to a control.

9. The CHO cell of claim 8, wherein said cell comprises a mutation in exon 2 of the matriptase gene.

10. The CHO cell of claim 8, wherein said expression level or activity of matriptase is reduced by gene knock-out.

11. The CHO cell of claim 1, wherein (i) the expression level or activity of C12orf35 protein is reduced in said cell as compared to a control, (ii) a telomeric region of chromosome 8 of said cell is deleted, (iii) the expression level or activity of FAM60A protein is reduced in said cell as compared to a control, and (iv) the expression level or activity of matriptase is reduced in said cell as compared to a control.

12. The CHO cell of claim 1, wherein said pentameric complex is soluble.

13. The CHO cell of claim 1, wherein said pentameric complex is secreted from the host cell.

14. A large scale culture comprising the CHO cell of claim 1, wherein said culture is at least 20 liter in size.

15. The large scale culture of 14, wherein the yield of said pentameric complex is at least 0.05 g/L.

16. A process of producing cytomegalovirus (CMV) pentameric complex, wherein said pentameric complex comprises: gH or a complex-forming fragment thereof, gL or a complex-forming fragment thereof, pUL128 or a complex-forming fragment thereof, pUL130 or a complex-forming fragment thereof, and pUL131 or a complex-forming fragment thereof, comprising:
(i) culturing the CHO cell of claim 1 under a suitable condition, thereby expressing said pentameric complex; and
(ii) harvesting said pentameric complex from the culture.

17. The process of claim 16, further comprising purifying said pentameric complex.

18. The CHO cell of claim 1, wherein (i) the expression level or activity of C12orf35 protein is reduced in said cell as compared to a control, (ii) a telomeric region of chromosome 8 of said cell is deleted, and (iii) the expression level or activity of FAM60A protein is reduced in said cell as compared to a control.

* * * * *